(12) United States Patent
Miyasaka et al.

(10) Patent No.: US 7,184,930 B2
(45) Date of Patent: Feb. 27, 2007

(54) METHOD AND DEVICE FOR MONITORING STATUS OF MECHANICAL EQUIPMENT AND ABNORMALITY DIAGNOSING DEVICE

(75) Inventors: Takanori Miyasaka, Kanagawa (JP); Hirotoshi Aramaki, Kanagawa (JP); Yasushi Mutou, Kanagawa (JP); Juntaro Sahara, Kanagawa (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 10/526,031

(22) PCT Filed: Aug. 29, 2003

(86) PCT No.: PCT/JP03/11114

§ 371 (c)(1),
(2), (4) Date: Feb. 28, 2005

(87) PCT Pub. No.: WO2004/027370

PCT Pub. Date: Apr. 1, 2004

(65) Prior Publication Data

US 2006/0167659 A1    Jul. 27, 2006

(30) Foreign Application Priority Data

| Aug. 30, 2002 | (JP) | .............. 2002-252877 |
| Nov. 21, 2002 | (JP) | .............. 2002-338423 |
| Dec. 20, 2002 | (JP) | .............. 2002-370800 |
| Jan. 17, 2003 | (JP) | .............. 2003-010131 |
| Feb. 25, 2003 | (JP) | .............. 2003-048309 |
| Jun. 26, 2003 | (JP) | .............. 2003-182996 |
| Aug. 28, 2003 | (JP) | .............. 2003-304700 |

(51) Int. Cl.
*G06F 11/00* (2006.01)

(52) U.S. Cl. ............... 702/183; 702/35; 702/34; 384/448; 384/445; 73/602; 246/169 A; 295/38; 295/36.1

(58) Field of Classification Search ............ 702/35, 702/34, 183; 384/448, 445, 91, 8, 7; 73/602; 246/169, 169 A; 295/35, 38, 36.1
See application file for complete search history.

(56) References Cited

U.S. PATENT DOCUMENTS 5,356,098 A * 10/1994 Post .................. 246/169 A (Continued)

FOREIGN PATENT DOCUMENTS

JP        47-9446 A        5/1972

(Continued)

OTHER PUBLICATIONS

ULB SMA, 'A Lab View mini-expert to identify bearing defects automatically', 1999, ULB Web Publication, pp. 1-21.*

(Continued)

*Primary Examiner*—Marc S. Hoff
*Assistant Examiner*—Elias Desta
(74) *Attorney, Agent, or Firm*—Sughrue Mion, PLLC

(57) ABSTRACT

An abnormality diagnosis system for diagnosing a presence or absence of an abnormality of a bearing unit for a railway vehicle axle, comprises a sensing/processing portion for outputting a signal generated from the bearing unit as an electric signal, a calculating/processing portion for making an abnormality diagnosis of the bearing unit based on an output of the sensing/processing portion, a result outputting portion for outputting a decision result of the calculating/processing portion, and a controlling/processing portion for feeding back a control signal to a control system of the railway vehicle based on the decision result.

45 Claims, 51 Drawing Sheets

U.S. PATENT DOCUMENTS

| | | |
|---|---|---|
| 6,199,018 B1 * | 3/2001 | Quist et al. .................... 702/34 |
| 6,484,109 B1 * | 11/2002 | Lofall ......................... 702/56 |
| 2002/0056398 A1 | 5/2002 | Batchtiger et al. |
| 2002/0083779 A1 * | 7/2002 | Narita et al. ........... 73/862.191 |
| 2005/0259903 A1 * | 11/2005 | Takizawa et al. ........... 384/448 |

FOREIGN PATENT DOCUMENTS

| | | |
|---|---|---|
| JP | 55-101705 A | 8/1980 |
| JP | 61-164138 A | 7/1986 |
| JP | 62-093620 A | 4/1987 |
| JP | 62-270820 A | 11/1987 |
| JP | 2-204696 A | 8/1990 |
| JP | 2-205727 A | 8/1990 |
| JP | 2-240536 A | 9/1990 |
| JP | 3-152436 A | 6/1991 |
| JP | 6-42983 A | 2/1994 |
| JP | 6-200929 A | 7/1994 |
| JP | 7-209143 A | 8/1995 |
| JP | 10-274558 A | 10/1998 |
| JP | 2000-133474 A | 5/2000 |
| JP | 2000-146762 A | 5/2000 |
| JP | 2000-289618 A | 10/2000 |
| JP | 2001-21453 A | 1/2001 |
| JP | 2001-500597 A | 1/2001 |
| JP | 2001-356808 A | 12/2001 |
| JP | 2002-71519 A | 3/2002 |
| JP | 2002-292928 A | 10/2002 |
| JP | 2002-295464 A | 10/2002 |
| WO | WO 98/11356 A1 | 3/1998 |

OTHER PUBLICATIONS

"Rolling Bearing", (Cat. No. 1101e, pp. B340-B351), issued by Nipon Seiko K.K.

* cited by examiner

FIG. 4

| FLAW OF A ROLLING BEARING | FREQUENCY AFTER AN ENVELOPING PROCESS |
|---|---|
| INNER RING (Si) | $Zfi = \dfrac{fr}{2}\left(1 + \dfrac{Da}{dm}\cos\alpha\right)Z$  [Hz] |
| OUTER RING (So) | $Zfc = \dfrac{fr}{2}\left(1 - \dfrac{Da}{dm}\cos\alpha\right)Z$  [Hz] |
| ROLLING ELEMENT (Sb) | $2fb = fr\left(1 - \dfrac{Da^2}{dm^2}\cos^2\alpha\right)$  [Hz] |
| RETAINER (Sc) | $fc = \dfrac{fr}{2}\left(1 - \dfrac{Da}{dm}\cos\alpha\right)$  [Hz] | fr: INNER RING ROTATION SPEED [Hz]
fc: RETAINER ROTATION SPEED [Hz]
fb: ROLLING ELEMENT ROTATION SPEED [Hz]
dm: PITCH CIRCLE DIAMETER [mm]
Z: NUMBER OF ROLLING ELEMENTS
fi: fr-fc
Da: ROLLING ELEMENT DIAMETER [mm]
$\alpha$: CONTACT ANGLE [DEGREE]

TIME-VARIANT WAVEFORM

FFT SPECTRUM $\delta_1(=Y_1-Y_0)>0$ – (1)
$\delta_2(=Y_2-Y_1)<0$ – (2)
WHERE A $(X_0,Y_0)$, B $(X_1,Y_1)$, C $(X_2,Y_2)$.
WHEN (1), (2) ARE SATISFIED AND
$dy/dx=(Y_1-Y_0)/(X_1-X_0)>1$
OR
$dy/dx=(Y_2-Y_1)/(X_2-X_1)<-1$
IS SATISFIED, $Y_1$ IS DECIDED AS A PEAK.

COLLATE ONLY THE PRIMARY, SECONDARY, QUATERNARY COMPONENTS (FLAW OF THE OUTER RING)

A RELATIONSHIP BETWEEN A SIZE OF
FLAKING AND A LEVEL DIFFERENCE

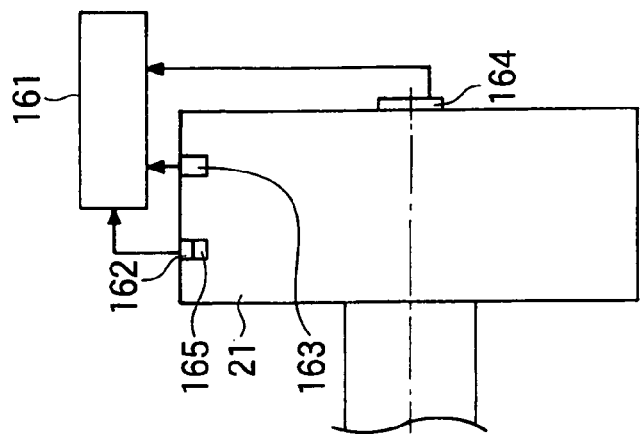
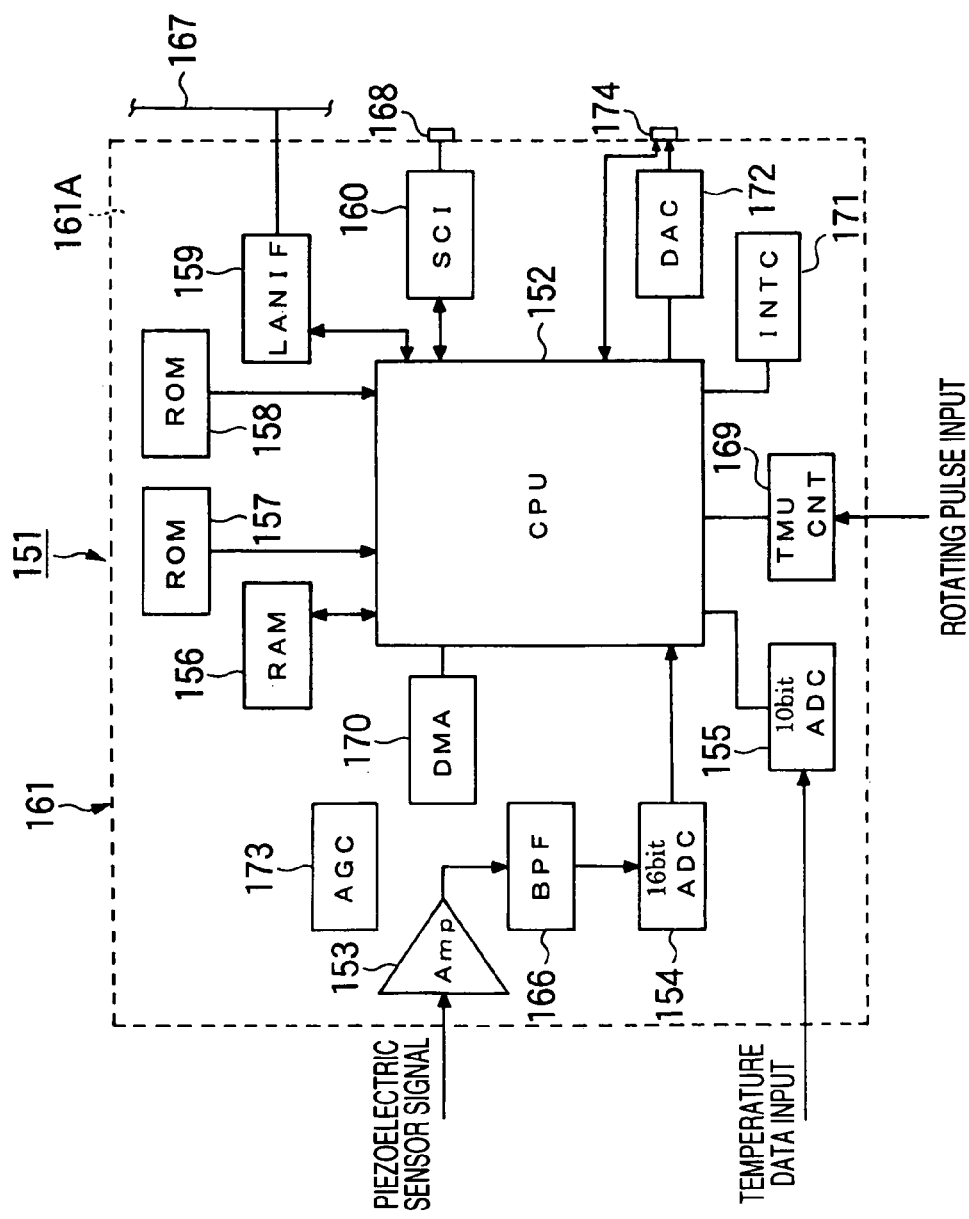
FIG. 34(a)
FIG. 34(b)

METHOD AND DEVICE FOR MONITORING STATUS OF MECHANICAL EQUIPMENT AND ABNORMALITY DIAGNOSING DEVICE

TECHNICAL FIELD

The present invention relates to a machinery facility condition monitoring method and system and an abnormality diagnosis system and, more particularly, a machinery facility condition monitoring method and system and an abnormality diagnosis system capable of monitoring conditions such as an abnormality, and so forth in a machinery facility such as a railway vehicle facility, a machine tool, a windmill, a reduction gear, an electric motor, or the like including at least one of a rotating body and a sliding member such as a rolling bearing, a sliding bearing, a ball screw, a linear guide, a linear ball bearing, and the like without decomposition of the machinery facility.

BACKGROUND ART

In the prior art, in order to prevent generation of the failure due to the wear or the failure of the rotating body or the sliding member, a thorough overhaul and a visual inspection are applied periodically to the machinery facility such as the railway vehicle facility, the machine tool, the windmill, or the like In the thorough overhaul and the visual inspection, the rotating body or the sliding member is removed from the machinery facility and decomposed after the facility is operated for a predetermined period, and then the skilled expert who handling the inspection checks a degree of the wear, the presence or absence of the flaw, or the like of respective constituent parts with a skilled eye. As major defects that are found by the inspection, in the case of the bearing unit, there are the indentation due to the capture of the foreign matter, etc., the flaking due to the rolling contact fatigue, other wear, and others. Also, in the case of the gear, there are the fracture or wear of the teeth, or the like. When the person who handles an inspection detects an abnormality such as unevenness, wear, and the like., which are not found in a new rotating body or sliding member, such person exchanges the defective parts for the new one and then assembles the rotating body or the sliding member once again (see the catalog "ROLLING BEARING" (CAT.No.1101e, page B340 to page B351) issued by Nippon Seiko K. K.).

However, in the method of decomposing the overall machinery facility and inspecting the failure with the eye of the person in charge, a decomposing operation of removing the rotating body or the sliding member from the machinery facility and a fitting operation of fitting again the inspected rotating body or sliding member into the machinery facility require much time and labor. Thus, such a problem existed that a substantial increase in an upkeep cost required for maintaining, managing, or the like the machinery facility is brought upon.

In particular, in the case of the windmill, most of the windmills are used in an offshore area and also the number of the installed windmills is large. It is the existing circumstances of maintaining/managing operations of the windmill that the person in charge of the maintenance goes to the installation location of the windmill and then conducts the inspection of rotating parts of the windmill there For this reason, such a problem existed that it take an enormous time and cost to maintain/manage the windmill and thus a maintenance efficiency is poor. Also, it is possible that the inspection itself causes the defect of the rotating body or the sliding member. For instance, the indentation that has not been put before the inspection is made on the rotating body or the sliding member when the machinery facility is reassembled after the decomposition and the inspection, and so forth. Also, since the person in charge of the inspection must check a number of bearings with the eye within a limited time, there existed the problem that such a possibility still remains that such person fails to find the defect. In addition, since a decision level of the defect varies between individuals and thus exchange of the parts is carried out even though the defect is not found substantially, the above inspection entails a useless cost.

Also, in order to overcome the disadvantages caused by such visual inspection, it is studied that the sensor for sensing the sound or the vibration generated during the rotation of the bearing is provided on the body of the vehicle in which the bearing is used, and then the abnormality such as the wear, the failure, or the like of the bearing is sensed based on the sensed signal of the sensor.

However, in the case where the sensor is fitted onto the body of the vehicle, an SN ratio of the sensed signal from the sensor is worsened because the sensor is provided away from the bearing. Thus, there existed such a problem that it is difficult to sense/decide the abnormality with high precision.

Also, as an bearing unit in the prior art, in a bearing unit 1100 having a sensor module shown in FIG. 50, a module hole 1103 is formed on an outer peripheral surface of an outer ring 1102 of a rolling bearing 1101, and then a module 1104 into which a speed sensor, a temperature sensor, and an acceleration sensor are installed is inserted/fixed into the module hole 1103. Then, sensed signals generated from respective sensors in the module 1104 are transmitted to a remote processing unit provided in the locomotive, which pulls the freight cars and the passenger cars in which the rolling bearings 1101 are provided, via the communication channel.

As to the speed, the instantaneous speed of the journal is sensed based on the pulse generated by the rotating wheel, and then such speed and the speed of other bearings that are operating under the same conditions are compared with each other. Thus, the overall period history to which the bearing assembly is subjected is saved/recorded. As to the temperature, such temperature and the temperature of other bearings that are operating under the same conditions are compared with each other by a simple level detection. As to the vibration, a simple RMS measurement of an energy level is carried out over a predetermined period of time, and then such energy level and the past energy level stored in a processing unit are compared with each other. Thus, such energy level and the energy level of other bearings that are operating under the same conditions are compared with each other (see JP-T-2001-500597 (pp.10 to 16, FIG. 1)).

Also, as another configurative example of the bearing unit, in an abnormality sensing unit 1110 of the rolling bearing unit shown in FIG. 51, a sensor fitting hole 1113 is formed in the lower end portion of an outer ring 1112 of a double row tapered roller bearing 1111, and then a sensor unit 1117 having a rotation speed sensor 1114, a temperature sensor 1115, and an acceleration sensor 1116 therein is inserted/supported into the sensor fitting hole 1113 (for example, see JP-A-2002-295464 (pp.4 to 5, FIG. 1)).

In addition, as other configurative example of the bearing unit, in a sensor built-in rotation supporting member 1120 shown in FIG. 52, a sensor fitting hole 1123 is formed in the lower end portion of an outer ring 1122 of a double row tapered roller bearing 1121, and then a sensor unit 1126 having a rotation speed sensor 1124 and a temperature sensor 1125 therein is inserted/supported into the sensor fitting hole 1123 (for example, see JP-A-2002-292928 (pp.4 to 5, FIG. 1)).

Further, as other configurative example, an abnormality sensing unit 1130 of the bearing unit shown in FIG.53 has a pickup 1132 for converting a mechanical vibration of a bearing 1131 into an electric vibration to output, an automatic gain control amplifier 1133 for amplifying an output of the pickup 1132, and a 1 to 15 kHz bandpass filter 1134 for removing noises generated from the driving system and other mechanical systems from the output of the amplifier 1133. Also, the unit 1130 has a root-mean-square calculator 1135 for calculating a root mean square value of the output of the bandpass filter 1134 and supplying the value to a gain control terminal of the automatic gain control amplifier 1133, an envelope circuit 1136 for receiving an output of the bandpass filter 1134, a root-mean-square calculator 1137 for receiving an output of the envelope circuit 1136, and an alarm circuit 1138 for receiving an output of the root-mean-square calculator 1137 and issuing an alarm by using a lamp or a contact output when such output value exceeds a predetermined value (for example, see JP-A-2-205727 (pp.2 to 3, FIG. 1)).

Furthermore, as other configurative example, an abnormality diagnosis system 1140 of the rolling bearing shown in FIG. 54 has a configuration that includes a microphone 1142 arranged in vicinity of a rolling bearing 1141, an amplifier 1143, an electronic device 1144, a speaker 1145, and a monitor 1146. The electronic device 1144 is a calculating/processing unit, and has a transducer 1147 as a converting portion, a HDD 1148 as a recording portion, an abnormality diagnosing portion 1149 as a calculating/processing portion, and an analog converting/outputting portion 1150 (for example, see JP-A-2000-146762 (pp.4 to 6, FIG. 1)).

Besides, as other configurative example, in an abnormality diagnosing method and an abnormality diagnosing system 1160 of the bearing shown in FIG. 55, an electric signal waveform that a sensor 1161 outputs is converted into the digital file by an analog/digital converter 1162, then is sent out to a waveform processing portion 1163, and then is subjected to the enveloping process by the waveform processing portion 1163 to get an envelope spectrum. Then, an inner ring flaw component, an outer ring flaw component, and a rolling element flaw component, which are particular frequency components of the bearing constituent parts, are extracted from the envelope spectrum by the waveform processing portion 1163 in the extracting step by using predetermined equations. Then, a calculating portion 1164 executes the calculating step, a deciding portion 1165 executes the comparing step, an outputting portion 1166 outputs the decided result, and a speaker 1167 and a monitor 1168 inform the inspector of the result (for example, see JP-A-2001-021453 (pp.5 to 6, FIG. 1)).

However, in the configurations of the bearing unit set forth in JP-T-2001-500597 and JP-A-2002-295464, since the sensor fitting hole is provided in the outer ring, the type of the outer rings constituting the bearing is increased such as the outer ring in which the hole is not provided and the outer ring in which the hole is provided. As a result, there is a possibility of generating the installing error, and the like, and also a lot of man-hours are needed to manage the parts. Also, it is possible that the outer ring with the hole hinders the sealing performance in the bearing.

Also, in the abnormality diagnosis system set forth in JP-A-2-205727, JP-A-2000-146762, and JP-A-2001-021453, merely the measure against the vibration-noise is disclosed. In the case where the bearing is used to support the axle of the railway vehicle, it is possible that this diagnosis system decides a great shock generated when the railway vehicle passes over the rail joint as an abnormal signal. Thus, the abnormality decision may be largely affected.

Also, in order to overcome the disadvantages caused by the overhaul inspection or the visual inspection, there is proposed a monitoring system that includes a sensor for sensing the sound or the vibration generated during the rotation of the bearing and an information processing system for analyzing a sensed signal of the sensor to decide whether or not the abnormality is generated and uses a personal computer as the information processing system (for example, see JP-A-2002-71519).

However, the personal computer used as the information processing system in the monitoring system in the prior art has normally such a configuration that a motherboard and an interface for receiving an output of the sensor are installed into a general-purpose casing. Thus, the information processing system needs a relatively large installing space and also has a tendency that does not endure the vibration, and the like well.

For this reason, in order to prevent an influence of the vibration on the bearing unit, etc., a space in which the personal computer is provided must be secured in the position that is distant from the bearing unit, etc. to some extent. In addition, this monitoring system becomes large in size. Therefore, in the case of the machinery facility in which the assurance of the large installing space is difficult, such a problem has arisen that such monitoring system is of little utility.

Also, in order to prevent a deterioration of the SN ratio of the signal sensed by the sensor, it is preferable that the sensor should be incorporated into the constituent parts itself of the bearing unit if possible. However, the personal computer that cannot stand up to the external vibration, and the like and is large in size must be separated as far as possible away from the bearing unit, or the like as the vibration generating source. As a result, the personal computer is apart from the sensor at a predetermined distance or more, and thus it is possible that the problem such as a reduction in a sensing precision due to the influence of the external noise on the information transmission path between the sensor and the personal computer, or the like is caused.

The present invention has been made in view of the above problems, and it is an object of the present invention to provide a high-precision machinery facility abnormality diagnosis system capable of deciding the presence or absence of an abnormality in a state of normal use without decomposition of a facility like a machinery facility such as a railway vehicle facility, a machine tool, a windmill, or the like, which requires much time and labor to decompose, and thus capable of reducing maintenance/administrative costs and being hardly affected by the noise, and the like.

DISCLOSURE OF THE INVENTION

The present invention can be attained by configurations described in the following.

(1) An abnormality diagnosis system for diagnosing a presence or absence of an abnormality of a bearing unit for a railway vehicle axle, comprising:

a sensing/processing portion for outputting a signal generated from the bearing unit as an electric signal;

a calculating/processing portion for making an abnormality diagnosis of the bearing unit based on an output of the sensing/processing portion;

a result outputting portion for outputting a decision result of the calculating/processing portion; and a controlling/processing portion for feeding back a control signal to a control system of the railway vehicle based on the decision result.

(2) An abnormality diagnosis system according to (1), wherein the calculating/processing portion includes a data accumulating/distributing portion for accumulating the electric signal fed from the sensing/processing portion and distributing the signal to an appropriate distributing route according to a type of the electric signal, an analyzing portion for calculating a predetermined physical quantity in regarding to the bearing unit based on the electric signal distributed from the data accumulating/distributing portion, a first data saving portion for saving bearing unit data in regarding to the bearing unit, a comparing/deciding portion for making the abnormality diagnosis of the bearing unit by comparing/referring an analyzed result of the analyzing portion with the bearing unit data saved in the first data saving portion, a second data saving portion for saving the analyzed result of the analyzing portion and a decision result of the comparing/deciding portion.

(3) An abnormality diagnosis system according to (2), wherein the analyzing portion includes a filtering processing portion for removing a noise component of the electric signal fed from the calculating/processing portion or extracting a particular frequency component to output, and a frequency analyzing portion for executing a frequency analysis of a signal output from the filtering processing portion, and the comparing/deciding portion makes the abnormality diagnosis of the bearing unit based on a result of the frequency analysis of the frequency analyzing portion, (4) An abnormality diagnosis system according to (2) or (3), wherein the analyzing portion has a temperature analyzing portion that calculates a temperature of the bearing unit based on the signal output from the data accumulating/distributing portion, and the comparing/deciding portion makes the abnormality diagnosis of the bearing unit based on the temperature analyzing portion.

(5) An abnormality diagnosis system according to any one of (2) to (4), wherein the analyzing portion has a rotation analyzing portion that calculates a rotation speed of the bearing unit based on the signal output from the data accumulating/distributing portion, and the comparing/deciding portion makes the abnormality diagnosis of the bearing unit based on the rotation speed calculated by the rotation analyzing portion.

(6) An abnormality diagnosis system according to any one of (1) to (5), wherein the calculating/processing portion outputs data saved in the second data saving portion to the controlling/processing portion in response to the abnormality diagnosis result.

(7) An abnormality diagnosis system according to any one of (1) to (6), wherein the filtering processing portion extracts only a frequency component of 1 kHz or less.

(8) An abnormality diagnosis system according to any one of (1) to (7), wherein a sensing element of the sensing/processing portion is arranged on a stationary portion of the bearing unit in a loading range.

(9) An abnormality diagnosis system according to any one of (1) to (8), wherein the data accumulating/distributing portion does not output the electric signal containing a noise component, which exceeds a predetermined level, to the analyzing portion.

(10) An abnormality diagnosis system according to any one of (1) to (9), wherein the comparing/deciding portion makes the abnormality diagnosis of the bearing unit by comparing levels of a frequency due to the abnormality and its higher harmonics with a reference value.

(11) An abnormality diagnosis system according to any one of (1) to (10), wherein the comparing/deciding portion decides that the abnormality is generated when at least one of peak values of the frequency due to the abnormal and its higher harmonics is larger than a predetermined reference value.

(12) An abnormality diagnosis system according to any one of (1) to (11), wherein the comparing/deciding portion estimates a degree of damage of the bearing unit based on the peak values of the frequency due to the abnormal and its higher harmonics.

(13) An abnormality diagnosis system according to any one of (1) to (12), wherein the comparing/deciding portion makes the abnormality diagnosis by comparing the levels of the frequency due to the abnormal and its higher harmonics.

(14) An abnormality diagnosis system according to any one of (1) to (13), wherein the comparing/deciding portion makes the abnormality diagnosis based on a square mean or a partial overall of a frequency band containing the frequency due to the abnormal.

(15) An abnormality diagnosis system according to any one of (1) to (14), wherein the comparing/deciding portion makes the abnormality diagnosis by applying a cepstrum analysis to a frequency spectrum.

(16) An abnormality diagnosis system according to any one of (1) to (15), wherein the signal is transmitted between the sensing/processing portion and the calculating/processing portion and the calculating/processing portion and the controlling/processing portion via a cable that has waterproof, oil-resistant, dustproof, rust-preventive, and moisture-proof functions, and heat-resistant, voltage-proof, and electromagnetic noise-resistant properties respectively.

(17) An abnormality diagnosis system according to any one of (1) to (15), wherein a radio communicating device is provided to the sensing/processing portion and the calculating/processing portion and the calculating/processing portion and the controlling/processing portion respectively, and the signal is transmitted therebetween by using the radio communicating device via radio.

(18) An abnormality diagnosis system according to any one of (1) to (15), wherein the signal is transmitted between the sensing/processing portion and the calculating/processing portion and the calculating/processing portion and the controlling/processing portion via the cable that has waterproof, oil-resistant, dustproof, rust-preventive, and moisture-proof functions, and heat-resistant, and electromagnetic noise-resistant properties respectively, or the signal is transmitted therebetween by using the radio communicating device.

(19) An abnormality diagnosis system according to any one of (1) to (18), wherein the abnormality diagnosis is made in real time.

(20) An abnormality diagnosis system according to any one of (1) to (18), wherein the abnormality diagnosis is made at a time different from a vehicle traveling time, based on data accumulated in the data accumulating/distributing portion.

(21) An abnormality diagnosis system according to any one of (1) to (20), wherein the presence or absence of the abnormality of a bearing in the bearing unit and an abnormality occurring location are diagnosed.

(22) An abnormality diagnosis system according to any one of (1) to (20), wherein a flat portion of a wheel is diagnosed.

(23) An abnormality diagnosis system according to any one of (1) to (20), wherein the presence or absence of the abnormality of a gear in the bearing unit and an abnormality occurring location are diagnosed.

(24) An abnormality diagnosis system for a machinery facility having a rotating body, comprising:

a sensor unit having a sensor fitted to a constituent parts of the rotating body to sense a physical quantity of the rotating body in a rotating operation;

a calculating/processing portion for deciding a presence or absence of an abnormality of the rotating body by analyzing an output signal of the sensor unit and then comparing an analyzed result with predetermined reference data; and a controlling/processing portion for displaying the analyzed result of the calculating/processing portion and a decision result of the calculating/processing portion, and controlling an operation of the machinery facility in response to the decision result.

(25) An abnormality diagnosis system according to (24), wherein the sensor unit has an output amplifying means for amplifying the output signal of the sensor.

(26) An abnormality diagnosis system according to (24) or (25), wherein the sensor unit has a radio communicating means for transmitting the output signal to the calculating/processing portion via radio.

(27) An abnormality diagnosis system according to (26), wherein the calculating/processing portion and the controlling/processing portion are provided to a monitoring base station that is remote from the rotating body.

(28) An abnormality diagnosis system according to (27), wherein the sensor unit is fitted to a bearing of a railway vehicle, and the sensor unit diagnoses the abnormality of the bearing.

(29) A machinery facility abnormality diagnosis system for sensing a presence or absence of an abnormality of a sliding member or a rotating body in a machinery facility, comprising:

a sensor unit having one of plural sensing elements for sensing a signal emitted from the machinery facility; and a calculating/processing portion for executing a calculating process to decide the presence or absence of the abnormality in the machinery facility based on an output of the sensing element;

wherein the calculating/processing portion is composed of a microcomputer.

(30) A machinery facility abnormality diagnosis system according to (29), wherein the sensor unit is incorporated into the sliding member or the rotating body.

(31) A machinery facility abnormality diagnosis system according to (30), wherein the microcomputer is fitted to the sliding member or the rotating body or a mechanism parts that supports the sliding member or the rotating body.

(32) A machinery facility abnormality diagnosis system according to (29), wherein the microcomputer and the sensor unit are mounted on a single device board, and are fitted to the sliding member or the rotating body or a mechanism parts that supports the sliding member or the rotating body as a single processing unit.

(33) A machinery facility abnormality diagnosis system according to any one of (29) to (32), wherein the calculating/processing portion is installed in a single casing.

(34) A machinery facility abnormality diagnosis system according to (33), wherein the sensor unit is arranged integrally in the casing.

(35) A machinery facility abnormality diagnosis system according to any one of (29) to (34), wherein the sensing element senses at least one of temperature, vibration displacement, vibration speed, vibration acceleration, force, distortion, acoustic, acoustic emission, ultrasonic waves, and rotation speed.

(36) A machinery facility abnormality diagnosis system according to any one of (29) to (35), wherein the calculating/processing portion includes central processing unit, amplifier, analog/digital converter, filter, comparator, pulse counter, timer, interruption controller, ROM, RRAM, digital/analog converter, communication module, and external interface.

(37) A machinery facility abnormality diagnosis system according to any one of (29) to (36), wherein the calculating/processing portion executes at least one process or more of calculation of feature parameters of a standard deviation and a peak factor, envelope detection, FFT, filtering, wavelet transform, short-time FFT, calculation of a feature frequency due to a defect of the rotating body and comparison/decision.

(38) A condition monitoring method for a machinery facility having at least one of a rotating body and a sliding member, comprising the steps of:

analyzing a predetermined physical quantity of the machinery facility based on a signal generated from the machinery facility;

provisionally diagnosing a presence or absence of an abnormality of the machinery facility by comparing/allocating an analyzed result with information serving as references to decide whether or not the abnormality is present in the machinery facility, every first time period; and diagnosing the presence or absence of the abnormality of the machinery facility and an abnormal location, by executing a total evaluation, which decides the abnormality when a number of times the abnormality is provisionally diagnosed exceeds a threshold value, after a comparison/allocation is executed predetermined number of times or based on a compared/allocated result obtained every second time period.

(39) A condition monitoring method for a machinery facility having at least one of a rotating body and a sliding member, comprising the steps of:

analyzing a predetermined physical quantity of the machinery facility based on a signal generated from the machinery facility;

provisionally diagnosing a presence or absence of an abnormality of the machinery facility by comparing/allocating an analyzed result with information serving as references to decide whether or not the abnormality is present in the machinery facility, every first time period; and diagnosing the presence or absence of the abnormality of the machinery facility and an abnormal location, by executing a total evaluation, which decides a degree of the abnormality according to a number of times the abnormality is provisionally diagnosed, after a comparison/allocation is executed predetermined number of times or based on a compared/allocated result obtained every second time period.

(40) A machinery facility condition monitoring method according to (38) to (39), wherein the signal is A/D-converted into a digital signal, then a process of analyzing a frequency of the digital signal is executed, and then a frequency component generated due to a damage of the machinery facility and calculated based on an operating signal of the machinery facility is compared/allocated with a frequency component derived based on actually measured data every first time period.

(41) A machinery facility condition monitoring method according to (40), wherein the signal is subjected to an amplifying process and a filtering process.

(42) A machinery facility condition monitoring method according to (40) or (41), wherein at least one of the rotating body and the sliding member of the machinery facility is any one of rolling bearing, ball screw, linear guide, and linear ball bearing, and the operating signal of the machinery facility is either a rotation speed signal in the rolling bearing and the ball screw or a moving speed signal in the linear guide and linear ball bearing.

(43) A machinery facility condition monitoring system for a machinery facility having at least one of a rotating body and a sliding member and using the condition monitoring method set forth in (38) or (39), comprising:

at least one sensing/processing portion for sensing a signal generated from the machinery facility;

a calculating/processing portion having a microcomputer that executes a calculating process to decide a condition of the machinery facility based on the signal output from the sensing/processing portion; and a controlling/processing portion having at least one of a result outputting portion that outputs a decision result of the calculating/processing portion and a controller that feeds back a control signal to a control system of the machinery facility based on the decision result.

(44) A machinery facility condition monitoring system according to (43), wherein at least one of the sensing/processing portion and the microcomputer is installed into the rotating body and the sliding member.

(45) A machinery facility condition monitoring system according to (43) or (44), wherein at least one of the rotating body and the sliding member is a bearing to which a radial load is applied, and the sensing/processing portion is fixed in a radial load loading range of a bearing housing that is fitted onto a raceway ring of the bearing.

(46) An abnormality diagnosis system for a railway vehicle bearing unit using the machinery facility condition monitoring system set forth in any one of (43) to (45).

(47) An abnormality diagnosis system for a windmill bearing unit using the machinery facility condition monitoring system set forth in any one of (43) to (45).

(48) An abnormality diagnosis system for a machine tool spindle bearing unit using the machinery facility condition monitoring system set forth in any one of (43) to (45).

(49) A machine equipment abnormality diagnosis system comprising:

a sensing/processing portion having a sensor unit that is fixed to a bolt screwed into a housing of the machine equipment and outputs a signal generated from the machine equipment as an electric signal;

a calculating/processing portion for making an abnormality diagnosis of the machine equipment based on an output of the sensing/processing portion; and a controlling/processing portion for feeding back a control signal to a control system of the machine equipment based on a result of the abnormality diagnosis.

(50) A machine equipment abnormality diagnosis system according to (49), wherein the calculating/processing portion includes the calculating/processing portion includes a data accumulating/distributing portion for accumulating the electric signal fed from the sensing/processing portion and distributing the signal to an appropriate distributing route according to a type of the electric signal, an analyzing portion for calculating a predetermined physical quantity in regarding to the machine equipment based on the electric signal distributed from the data accumulating/distributing portion, a first data saving portion for saving machine equipment data in regarding to the machine equipment, a comparing/deciding portion for making the abnormality diagnosis of the machine equipment by comparing the physical quantity calculated by the analyzing portion with the machine equipment data saved in the first data saving portion, a second data saving portion for saving the analyzed result of the analyzing portion and a result of the abnormality diagnosis of the comparing/deciding portion.

(51) A machine equipment abnormality diagnosis system according to (49) or (50), wherein the calculating/processing portion and the controlling/processing portion are composed of a microcomputer or an IC chip.

(52) A machine equipment abnormality diagnosis system according to any one of (49) to (51), wherein the signal is transmitted between the sensing/processing portion and the calculating/processing portion or the calculating/processing portion and the controlling/processing portion without a wire connection.

(53) A bearing unit including an inner ring having an inner ring raceway surface, an outer ring having an outer ring raceway surface, a plurality of rolling elements arranged relatively rotatably between the inner ring raceway surface and the outer ring raceway surface, and a retainer for holding rollably the rolling elements, whereby a bearing to which a radial load is applied is arranged in a bearing housing, the bearing unit comprising:

an abnormality sensing means provided in a loading range of the bearing housing, for sensing an abnormality from at least one selected from a vibration sensor and a temperature sensor installed/fixed in a single case.

(54) A bearing unit according to (53), wherein a flat portion is provided to a part of an outer peripheral surface of the bearing housing on a loading range side, and the abnormality sensing means is fixed to the flat portion.

(55) A bearing unit according to (54), wherein the abnormality sensing means is arranged on an outer diameter portion of the bearing housing on the loading range side in a center portion of a bearing width.

(56) A bearing unit according to (53), wherein the abnormality sensing means is arranged on an outer diameter portion of the bearing housing on the loading range side in a width area of the inner ring raceway surface or the outer ring raceway surface.

(57) A bearing unit according to any one of (53) to (56), wherein a case of the abnormality sensing means has a signal carrying means that sends out a sensed signal, and a decision result outputting portion that decides a presence or absence of the abnormality based on the signal sent out via the signal carrying means and output a decision result.

(58) A bearing unit according to any one of (53) to (57), wherein the abnormality sensing means is embedded/fixed on a recess portion formed on the bearing housing, and then secured by molding a clearance between the abnormality sensing means and the recess portion.

(59) A bearing unit according to (58), wherein the abnormality sensing means is fixed to the recess portion via a spacer.

(60) A bearing unit according to any one of (53) to (59), wherein a filtering processing portion for removing an unnecessary frequency band from a vibration waveform from the vibration sensor, an envelope processing portion for detecting an absolute value of a filtered waveform transferred from the filtering processing portion, a frequency analyzing portion for analyzing a frequency of a waveform transferred from the envelope processing portion, a comparing/collating portion for comparing a frequency generated due to a damage calculated based on a rotation speed with a frequency derived based on actually measured data, and a result outputting portion for identifying a presence or absence of the abnormality and an abnormal location based on a compared result in the comparing/collating portion are provided.

BRIEF DESCRIPTION OF THE DRAWINGS

FIG. 4 is a table showing relational expressions indicating relationships between defects of respective members of a bearing and abnormal vibration frequencies generated in respective members;

FIG. 34(a) is a block diagram showing a schematic configuration of a machinery facility abnormality diagnosis system according to an eighth embodiment of the present invention;

FIG. 34(b) is a side view showing a bearing fitting state in FIG. 34(a);

BEST MODE FOR CARRYING OUT THE INVENTION

A machinery facility condition monitoring method and system and an abnormality diagnosis system according to the present invention will be explained in detail with reference to the accompanying drawings hereinafter.

<First Embodiment>

Figure 1:
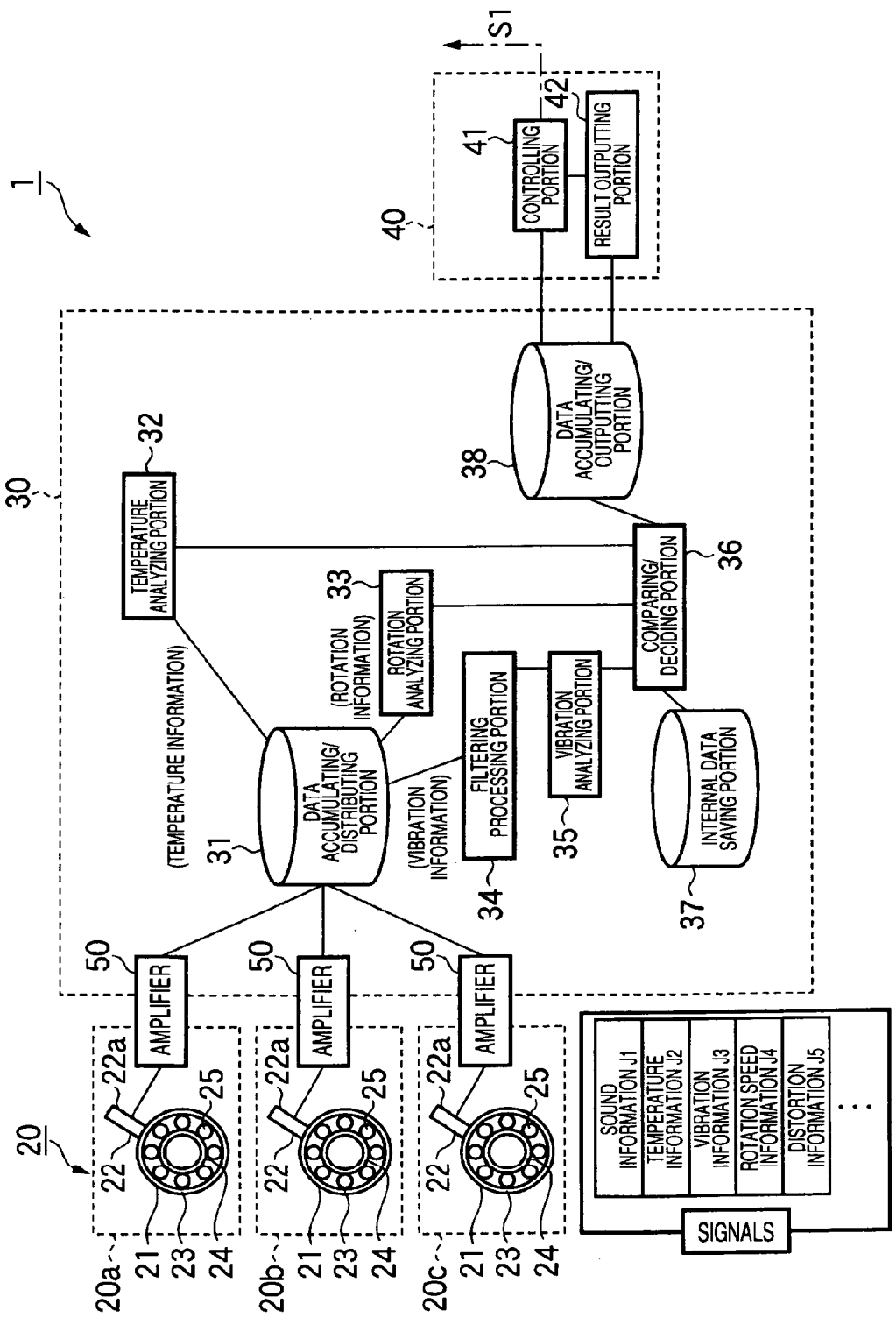
FIG. 1 is a view showing a railway vehicle abnormality diagnosis system according to a first embodiment of the present invention.

FIG. 1 shows a railway vehicle abnormality diagnosis system according to a first embodiment of the present invention. An abnormality diagnosis system 1 includes a sensing/processing portion 20 having sensor units 22 each provided to each row of a rolling bearing 21 to output a condition of each row as an electric signal, a calculating/processing portion 30 for calculating/processing the electric signals output from the sensor units 22 to decide the condition such as defect, abnormality, or the like of a railway vehicle facility 10, and a controlling/processing portion 40 for controlling and outputting the decided result of the calculating/processing portion 30.

The abnormality diagnosis system 1 senses the generation of the abnormality due to the wear or the failure of a plurality of rolling bearings 21 in the bearing unit that bears the axle of the railway vehicle. Each rolling bearing 21 has an outer ring 23 as a stationary portion that is fitted into the vehicle body side, an inner ring 24 fitted onto the axle and rotated together with the axle, and rolling elements 25 such as balls, rollers, or the like held between an outer ring raceway formed on the inner peripheral surface side of the outer ring 23 and an inner ring raceway formed on the peripheral surface side of the inner ring 24 by a retainer (not shown) and arranged rollably between both raceways. Also, the sensor unit is secured to the outer ring 23 of each rolling bearing 21. In FIG. 1, the sensing/processing portion 20 is constructed by sensing portions 20a, 20b, 20c each consisting of the sensor unit 22 secured to each rolling bearing 21.

The sensor unit 22 has sensors as a plurality of sensing elements that sense various information generated from the machinery facility during the running, e.g., sound J1, temperature J2, vibration (vibration displacement, vibration speed, vibration acceleration) J3, rotation speed J4, distortion J5 generated on the outer ring of the bearing, AE (acoustic emission), moving speed, force, ultrasonic wave, etc., as physical quantities that are changed in response to a rotating condition of the bearing 21. Each sensor outputs the sensed physical quantity to the calculating/processing portion 30 as the electric signal.

Here, since the calculating/processing portion 30 can distribute/process appropriately the electric signals every sensed information, respective sensing elements are arranged independently in different locations respectively. Thus, a plurality of sensing elements for sensing independently the particular signals such as sound, temperature, vibration, rotation speed, distortion, AE, moving speed, force, ultrasonic wave, and others may be employed in combination. Alternately, a composite sensor unit constructed by installing a plurality of sensing elements into an inside of a housing to sense simultaneously plural types of signals may be employed as the sensor unit 22, in place of independent arrangement of a plurality of sensing elements. Also, a multidirectional simultaneous vibration sensor for sensing the vibration in the multiple directions by one sensor may be employed as the vibration sensor.

Figure 2A:
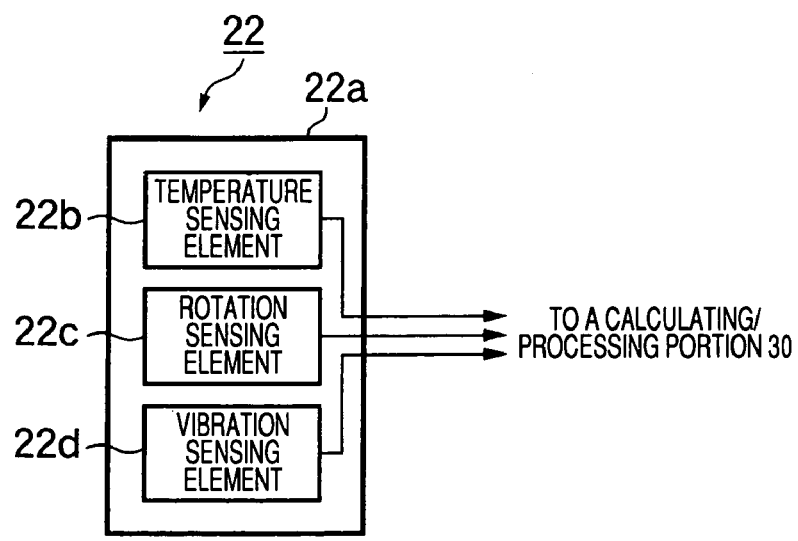
FIG. 2 is a block diagram showing an internal structure of a sensor unit.
Figure 5:
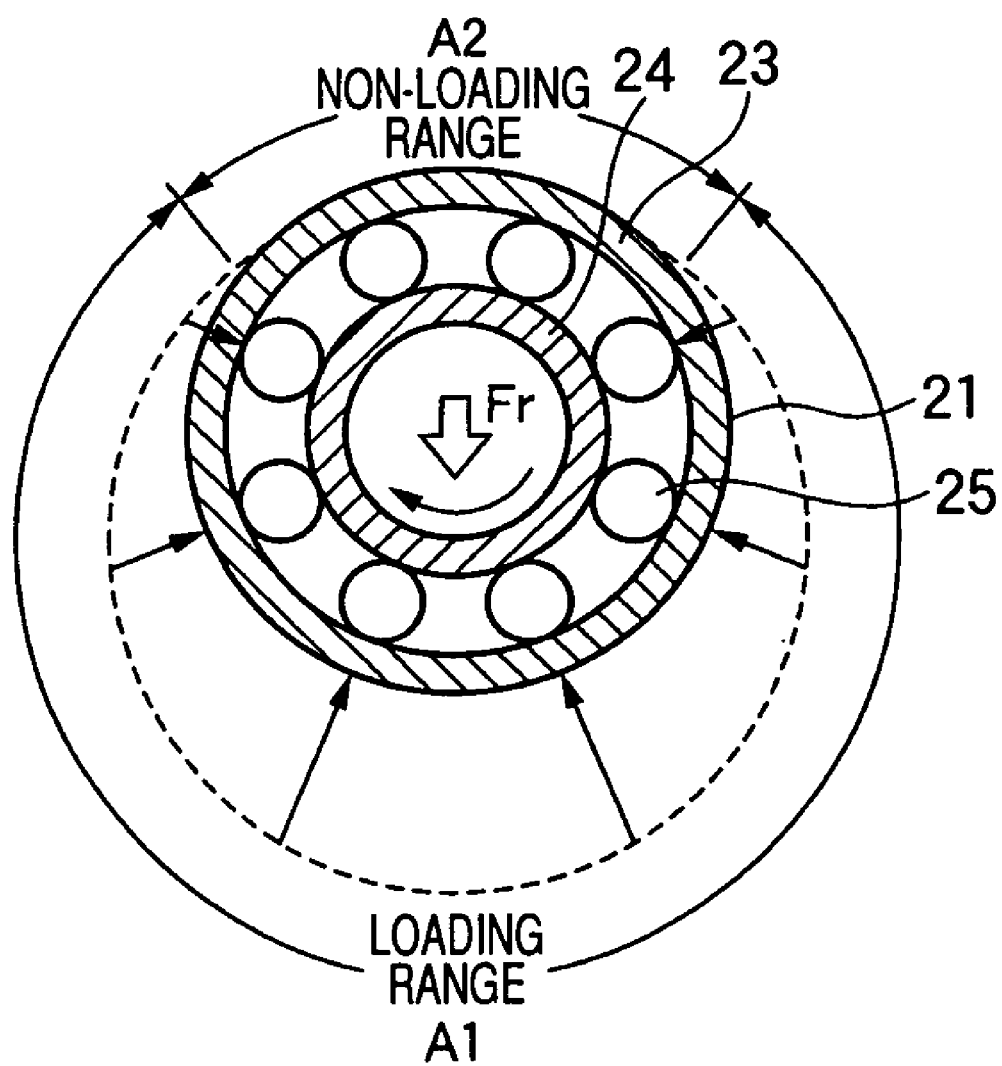
FIG. 5 is a view showing a relationship between a loading range and a non-loading range in the bearing.

In addition, in order to execute the sensing at a high SN ratio, the signal can be sensed with good sensitivity by fitting the sensor unit 22, especially a vibration sensing element 22d (see FIG. 2(a)), to a portion to which a load is applied (loading range) and thus the higher-precision measurement can be attained. Where the "loading range" denotes an area in which the load is applied to the rolling elements, as shown in FIG. 5. In the case where the sensor unit is fitted inevitably to a non-loading range when the space used to fit the sensor is absent in the loading range, a high-tension cable that generates noises is provided to the loading range, or the like, the measurement can be carried out by enhancing a signal sensing sensitivity by virtue of a filtering process executed by a filtering processing portion 34 described later, or the like.

In the present embodiment, as shown in FIG. 2(a), the sensor unit 22 has such a structure that various sensing elements 22b, 22c, and 22d are installed into a unit case 22a. Then, explanation will be made hereunder under the assumption that the temperature sensing element 22b for sensing the temperature of the bearing 21, the rotation sensing element 22c for sensing the rotation speed of the inner ring (axle) of the bearing 21, and the vibration sensing element 22d for sensing the vibration generated in the bearing 21 are provided in the unit case 22a.

Figure 2B:
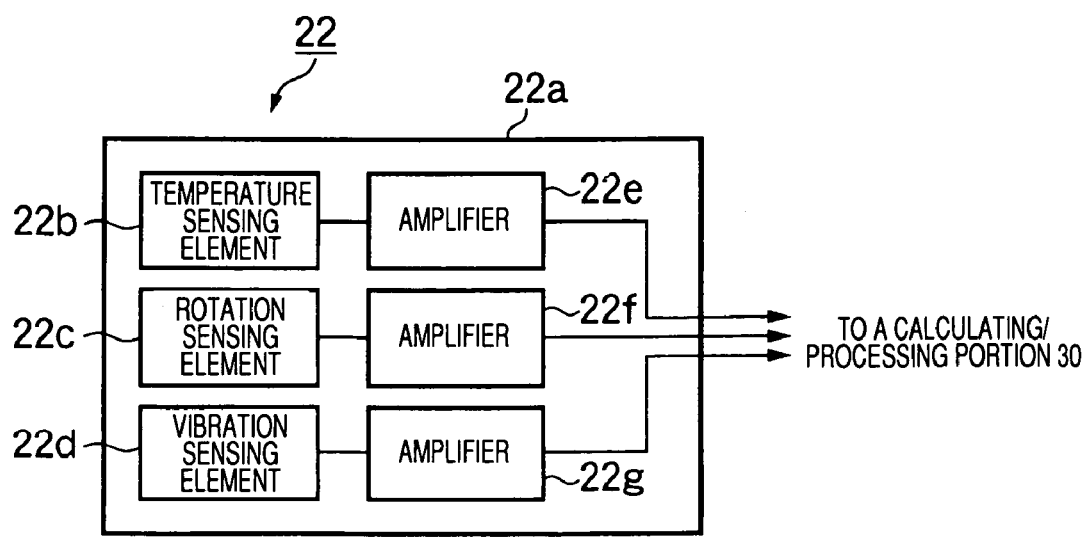

Respective sensing elements 22b to 22c amplify the electric signals corresponding to the sensed vibration, temperature, and rotation speed via an amplifier 50 as an output amplifying means, and then output the signals to the calculating/processing portion 30. The amplifier 50 may be provided in the unit case 22a of the sensor respectively as shown in FIG. 2(b), or the amplifier 50 may be provided between the sensor unit 22 and the calculating/processing portion 30 respectively as shown in FIG. 1, or the amplifier 50 may be provided to an interior of the calculating/processing portion 30. It is preferable that amplifiers 22e, 22f, and 22g should be provided to the sensing elements 22b, 22c, and 22d in the unit case 22a respectively. There is such a possibility that the noise is superposed on the signal during when the signal output from the sensor unit 22 is being transmitted to the calculating/processing portion 30 via the cable, and thus the reliability of measurement is lowered. In this event, if a signal level is amplified in advance via the amplifier 50, the signal is hard to accept the influence of the noise and thus the reliability can be improved.

The signal is transmitted between the sensor unit 22 and the calculating/processing portion 30 via the cable. In order to improve a measuring precision such as reduction of noise, etc., it is preferable that the cable should have waterproof, oil-resistant, dustproof, rust-preventive, moisture-proof, heat-resistant, and electromagnetic noise-resistant properties. Similarly, in order to improve a measuring precision such as reduction of noise, etc., it is preferable that respective sensing elements 22b to 22d in the sensor unit 22 should have waterproof, oil-resistant, dustproof, rust-preventive, moisture-proof, heat-resistant, and electromagnetic noise-resistant properties. For example, if all sensing elements are incorporated into the sensor unit and then the waterproof, oil-resistant, dustproof, rust- preventive, moisture-proof, heat-resistant, and electromagnetic noise-resistant properties are provided to the unit case 22a of the sensor unit 22, these properties can be embodied.

The calculating/processing portion 30 is a unit that executes the calculating process of the electric signals as the outputs that are received from respective sensing elements (the temperature sensing element 22b, the rotation sensing element 22c, and the vibration sensing element 22d in the present embodiment) in the sensor unit 22, and then identifies the presence or absence of the abnormality of the bearing and an abnormality occurring location by comparing the analyzed result analyzed by the calculating process and the reference data. Here, the reference data denote reference values of various physical quantities that are sensed by respective sensing elements in the normal condition of the bearing 21 serving as the diagnosed object. More particularly, the reference data contain the information about a frequency component generated by the wear or the failure of the particular portion of the bearing 21, and the like, in addition to the information of the normal bearing 21 about sound, temperature, vibration, rotation speed, distortion, AE, moving speed, force, ultrasonic wave, and the like.

For instance, the calculating/processing portion 30 may be constructed by using the personal computer or the general- purpose computer into which the existing operating system and the software applications used to execute the abnormality diagnosis. Otherwise, the calculating/processing portion 30 may be constructed as an arithmetic unit that are composed of processing and saving circuits provided independently to respective portions.

The calculating/processing portion 30 includes a data accumulating/distributing portion 31, a temperature analyzing portion 32, a rotation analyzing portion 33, the filtering processing portion 34, a vibration analyzing portion 35, a comparing/deciding portion 36, an internal data saving portion 37 serving as a first data saving portion, a data accumulating/outputting portion 38 serving as a second data saving portion. Then, configurations and functions of respective portions of the calculating/processing portion 30 will be explained in detail hereunder.

Figure 3:
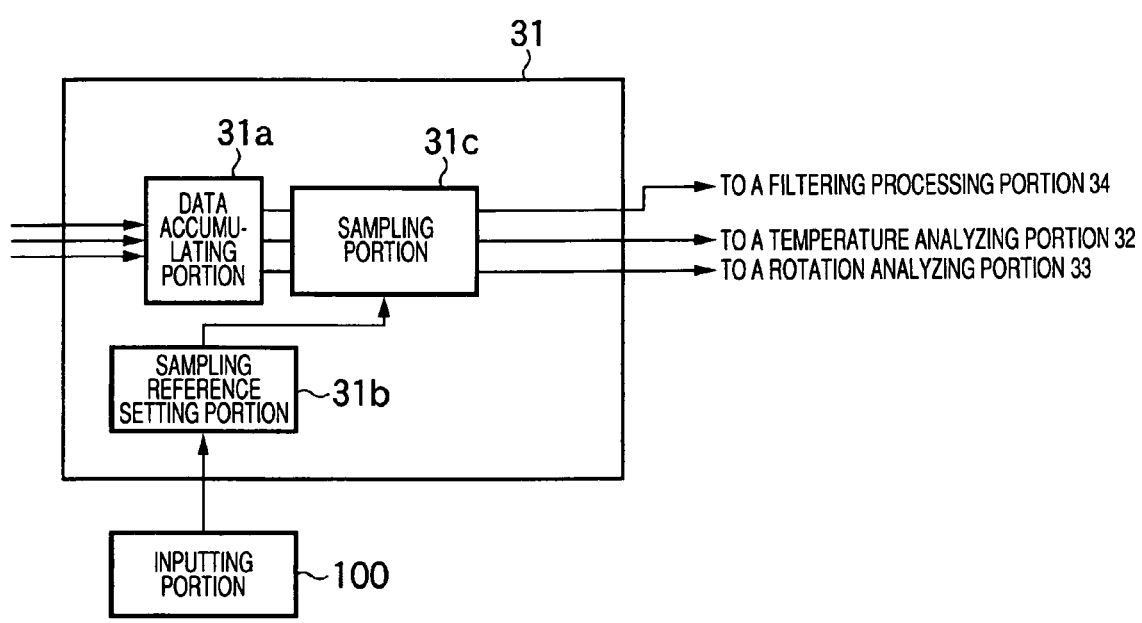
FIG. 3 is a view showing a data accumulating/distributing portion.

FIG. 3 is a view showing the data accumulating/distributing portion 31 serving as a first data accumulating portion. The data accumulating/distributing portion 31 has a data accumulating portion 31a, a sampling portion 31c, and a sampling reference setting portion 31b. The data accumulating portion 31a is a data saving medium that save the output signals from the sensing elements 22b to 22d every signal, and can be constructed by various memories, the hard disk, and the like.

The data accumulating portion 31a receives the signals sent out from the sensing elements 22b to 22d, and then stores temporarily such signals and also allocates such signals to any of the analyzing portions 32, 33, 34 in response to the type of signal. Various signals are A/D-converted into digital signals by an A/D converter (not shown) at the preceding stage to the data accumulating/distributing portion 31. In this event, the A/D conversion and the amplification may be applied in reverse order.

The sampling reference setting portion 31b sets the reference values that are used to exclude areas, in which the influence of the noise appears largely, from the analog signal being output from the vibration sensing element 22d, based on the information derived from an external inputting portion 100. Here, the inputting portion 100 is an inputting means such as a mouse, a keyboard, or the like, and the user can set arbitrarily the reference values via the inputting portion 100.

The sampling portion 31c cuts out vibration, temperature, and rotation speed data serving as the time-variant data into a predetermined length data, and then executes the sampling to output the signal to the analyzing portions in the subsequent stage. When the output signal from the vibration sensing element 22d contains the larger noise than the reference value being set by the sampling reference setting portion 31b, the sampling portion 31c does not execute the sampling of the signal in a period of time containing such noise not to output the signal to the filtering processing portion 34. More particularly, the sampling portion 31c detects two points A and B at which the signal level exceeds a certain predetermined value, and then controls not to output the data to the filtering processing portion 34 and the vibration analyzing portion 35 in a time interval A to D. Accordingly, it is possible not to execute the frequency analysis within the time interval that contains the data on which the large noise is superposed, so that a possibility of executing the false abnormality diagnosis can be reduced. In this case, the sampling reference setting portion 31b and the sampling portion 31c are not always provided. Also, if the similar effect can be achieved, these portions may be arranged in another location, e.g., the preceding stage of the data accumulating portion 31a, or the like.

The temperature analyzing portion 32 calculates the temperature of the bearing based on the output signal fed from the temperature sensing element 22b, and then sends out the calculated temperature to the comparing/deciding portion 36. The temperature analyzing portion 32 has a temperature transformation table responding to characteristics of the sensing elements, for example, and calculates the temperature data based on a level of the sensed signal.

The rotation analyzing portion 33 calculates the rotation speed of the inner ring 24, i.e., the axle based on the output signal fed from the rotation sensing element 22c, and then sends out the calculated rotation speed to the comparing/deciding portion 36. For example, when the rotation sensing element 22c is composed of an encoder fitted to the inner ring 24, a magnet fitted to the outer ring 23, and a magnetism sensing element, a signal output from the rotation sensing element 22c is given as a pulse signal that responds to a shape of the encoder and the rotation speed. The rotation analyzing portion 33 contains a predetermined transformation function or transformation table in response to the shape of the encoder, and calculates the rotation speed of the inner ring 24 and the axle from the pulse signal based on the function or the table.

The vibration analyzing portion 35 executes the frequency analysis of the vibration generated in the bearing 21 based on the output signal from the vibration sensing element 22d. More specifically, the vibration analyzing portion 35 is composed of an FFT computing portion that calculates the frequency spectrum of the vibration signal and calculates the frequency spectrum of the vibration in compliance with the FFT algorithm. The calculated frequency spectrum is fed to the comparing/deciding portion 36. Also, the vibration analyzing portion 35 may be constructed to execute the enveloping process as the preprocessing prior to the FFT to calculate the envelope of the vibration signal and thus attain a reduction of the noise. The vibration analyzing portion 35 also outputs the envelope data obtained after the enveloping process to the comparing/deciding portion 36, as the case may be.

Normally the abnormal frequency bands of the vibration caused due to the rotation of the bearing are decided depending upon a size of the bearing, the number of rolling elements, etc. Respective relationships between the defect of respective members of the bearing and the abnormal vibration frequencies generated in respective members are given as shown in FIG. 4. In the frequency analysis, the maximum frequency that permits the Fourier transform (Nyquist frequency) is decided in response to a sampling time, and thus preferably the frequency that is in excess of the Nyquist frequency should not be contained in the vibration signal. Therefore, the present embodiment is constructed such that the filtering processing portion 34 is provided between the data accumulating/distributing portion 31 and the vibration analyzing portion 35, a predetermined frequency band is cut out from the vibration signal by the filtering processing portion 34, and the vibration signal containing only the cut-out frequency band is sent out to the vibration analyzing portion 35. When the axle is being rotated at a low speed in the railway vehicle, only the frequency component of 1 kHz or less, for example, may be extracted.

Also, the filtering processing portion 34 may be arranged in such a manner that the portion first causes the vibration analyzing portion 35 to calculate the frequency spectrum without the filtering process, then estimates previously the frequency band in which the peak will be observed, and then executes the filtering process in answer to the frequency band to execute newly the frequency analysis. With this arrangement, the unnecessary noise can be eliminated effectively and thus the high-precision frequency analysis can be executed.

Figure 6:
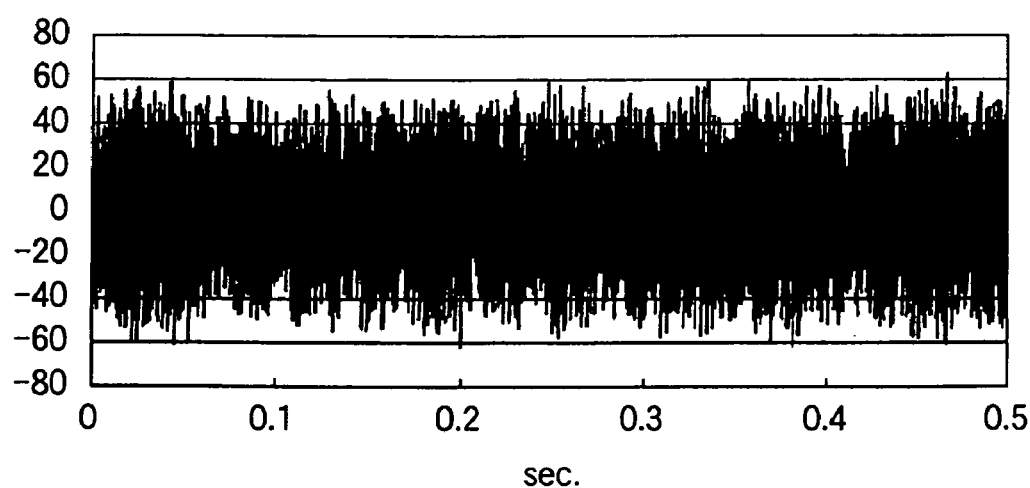
FIG. 6 is a view showing a time-variant waveform of an oscillating signal sensed from the bearing in the first embodiment.
Figure 7:
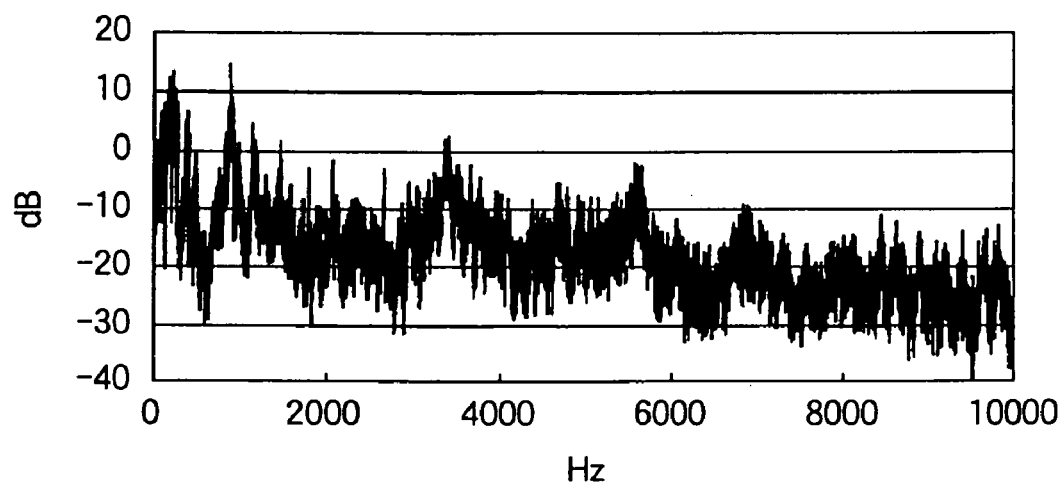
FIG. 7 is a view showing a frequency spectrum of the vibration signal sensed from the bearing in the first embodiment.
Figure 8:
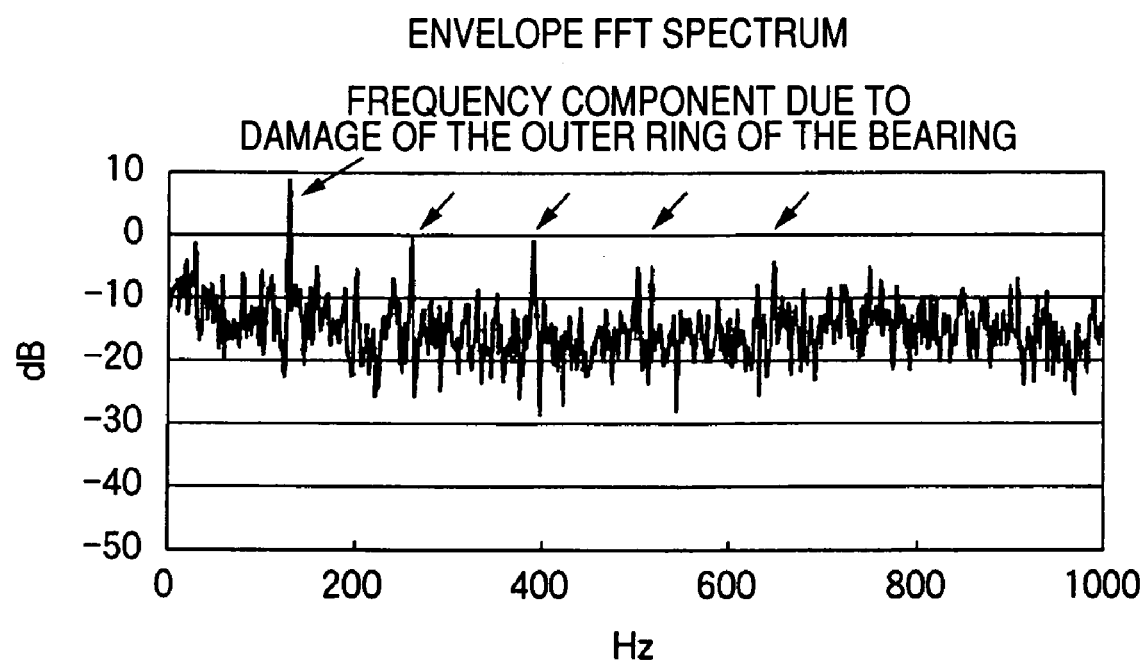
FIG. 8 is a view showing a frequency spectrum of the vibration signal sensed from the bearing in the first embodiment after an enveloping process.

FIG. 6 is a view showing a time-variant waveform of an oscillating signal as the vibration information J3 in regarding to the vibration of the rolling bearing 21 sensed by the sensor unit 22 in the present embodiment, FIG. 7 shows the frequency spectrum of the vibration signal sensed by the vibration analyzing portion 35 in the present embodiment, and FIG. 8 shows the frequency spectrum of the vibration signal sensed by the vibration analyzing portion 35 in the present embodiment after the enveloping process.

In this manner, the vibration analyzing portion 35 applies the frequency analysis to the vibration signal and calculates the frequency spectrum shown in FIG. 7 or FIG. 8. The strong spectrum is observed at a predetermined frequency period from FIG. 8. It is understood from the relational expression given in FIG. 4 that this corresponds to a frequency component generated due to the damage of the outer ring 23 of the rolling bearing 21.

In FIG. 3, the temperature analyzing portion 32, the rotation analyzing portion 33, and the vibration analyzing portion 35 are illustrated. But respective analyzing portions may be provided in response to the information that are sensed by respective sensing elements in the sensor unit 22.

The comparing/deciding portion 36 compares the frequency spectrum of the vibration sensed by the vibration analyzing portion 35 with the reference value saved in the internal data saving portion 37 or the reference value calculated from the frequency spectrum to decide whether or not the abnormal vibration is being generated. Where the reference values are the data of the frequency components generated due to the wear or the failure of the particular location of the bearing or predetermined values contained in the spectrum calculated every frequency spectrum. In order to expect an accuracy of the decision, the comparing/deciding portion 36 refers to the analyzed result of the temperature and the rotation speed obtained by the temperature analyzing portion 32 and the rotation analyzing portion 33 and specification data of various data of the bearing accumulated in the internal data saving portion 37, etc., simultaneously with the decision based on the comparison between the frequency components.

More particularly, if it is decided based on the frequency spectrum of the vibration that the abnormality occurs, the comparing/deciding portion 36 checks the temperature of the bearing and then decides that the serious abnormality is being generated if the temperature exceeds a predetermined value. Also, if only any one indicates the abnormality, the comparing/deciding portion 36 decides that any abnormality occurs. Then, if both results are normal, the comparing/deciding portion 36 decides that no abnormality occurs. If only any one indicates the abnormality, it may be decided that the abnormality occurs when the results are not varied after the decision is made in plural number of times. The comparing/deciding portion 36 outputs the result of the abnormality diagnosis to the data accumulating/outputting portion 38.

As the particular abnormality diagnosis process executed by the comparing/deciding portion 36 based on the vibration information, following methods will be listed.

Figure 9:
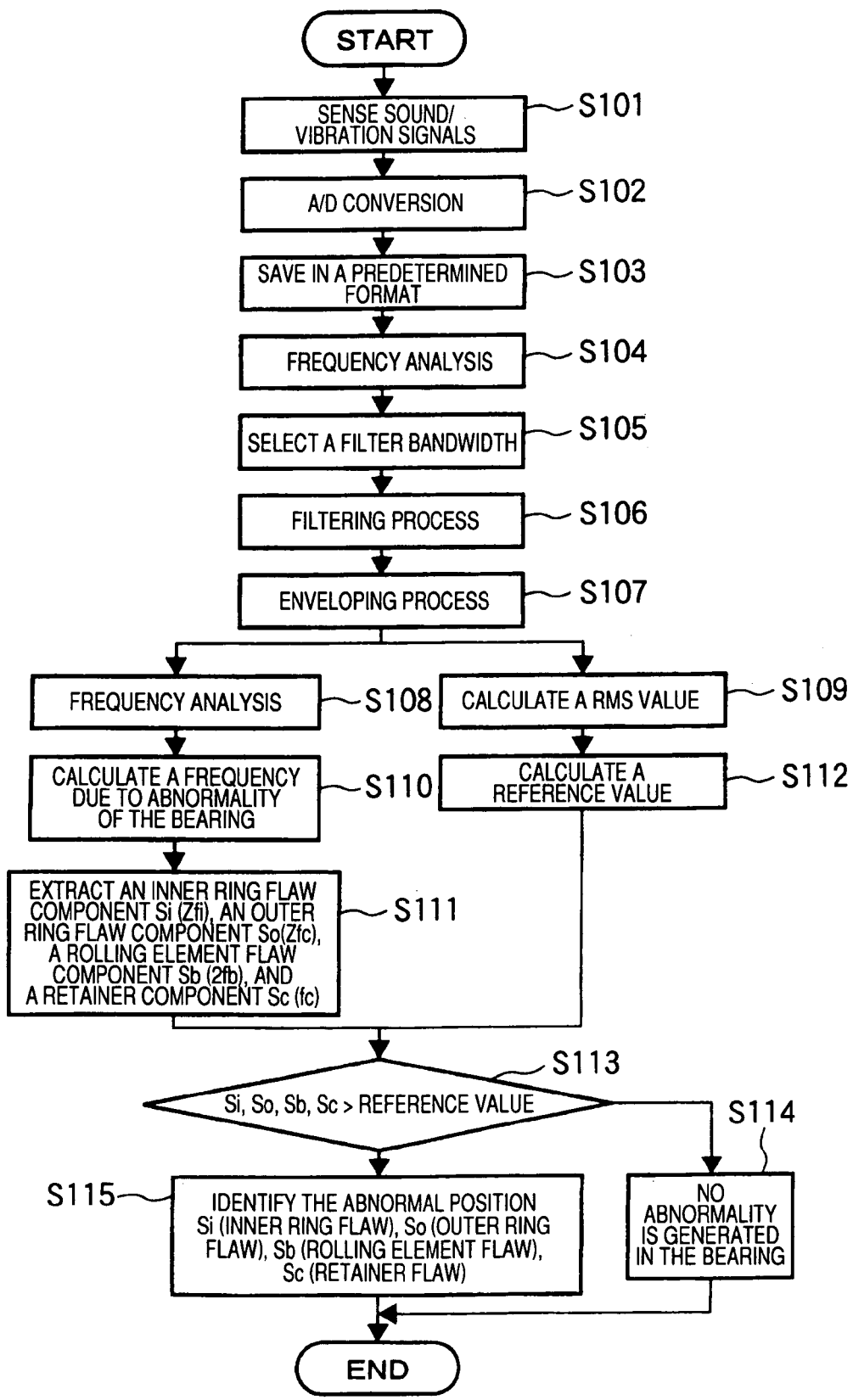
FIG. 9 is a flowchart showing a process flow in a first method.

(1) Method of using root-means-square values of the envelope data as the reference value The present method calculates the frequency components generated at the time of abnormality based on the expressions in FIG. 4. Then, the root-means-square values of the envelope data are calculated and then the reference values used in the comparison are calculated from the root-means-square values. Then, the frequencies that are in excess of the reference values are calculated and then compared with the frequency components generated at the time of abnormality. Then, explanation will be made with reference to FIG. 9 hereunder.

First, the vibration of the bearing is sensed by the vibration sensing element 22d installed in the sensor unit case 22a (step S101). The sensed signal is amplified by a predetermined amplification factor and then converted into the digital signal by an A/D converter (step S102). The vibration signal converted into the digital signal is saved in the data accumulating/distributing portion 31 in a predetermined format (step S103).

Then, the frequency spectrum of the digital signal is calculated (step S104). Then, the filtering processing portion 34 selects a filter bandwidth that is applied to the digital signal, based on the calculated frequency spectrum (step S105). Then, the filtering processing portion 34 executes the filtering process to remove the frequency components other than the selected filter band (step S106), and then outputs the digital signal after the filtering process to the vibration analyzing portion 35. Then, the vibration analyzing portion 35 applies the enveloping process to the digital signal after the filtering process (step S107) Then, the frequency spectrum of the digital signal after the enveloping process is calculated (step S108).

At the same time, the root-means-square value of the digital signal after the enveloping process is calculated (step S109). Then, the reference value used in the abnormality diagnosis is calculated based on the root-means-square value (step S112). Where the root-means-square value is calculated as a square root of a square mean of the frequency spectrum after the enveloping process. The reference value is calculated as follows based on the root-means-square value in accordance with an Equation (1) or (2).

(Reference value)=(Root-means-square value)+α  (1)

(Reference value)=(Root-means-square value)×β  (2)

α, β: predetermined value variable according to the type of data

Then, frequencies generated due to the abnormality of the bearing are calculated based on a table shown in FIG. 4 (step S110). Then, levels of abnormal frequency components of respective members corresponding to the calculated frequencies, i.e., an inner ring flaw component Si (Zfi), an outer ring flaw component So (Zfc), a rolling element flaw component Sb (2fb), and a retainer flaw component Sc (fc) are extracted (step S111). Then, respective components Si, So, Sb, Sc are compared with the reference value calculated in step S112 (step S113). Then, if all component values are smaller than the reference value, it is decided that no abnormality is generated in the bearing (step S114). In contrast, if any component exceeds the reference value, it is decided that the abnormality is generated in the concerned location (step S115).

Figure 10:
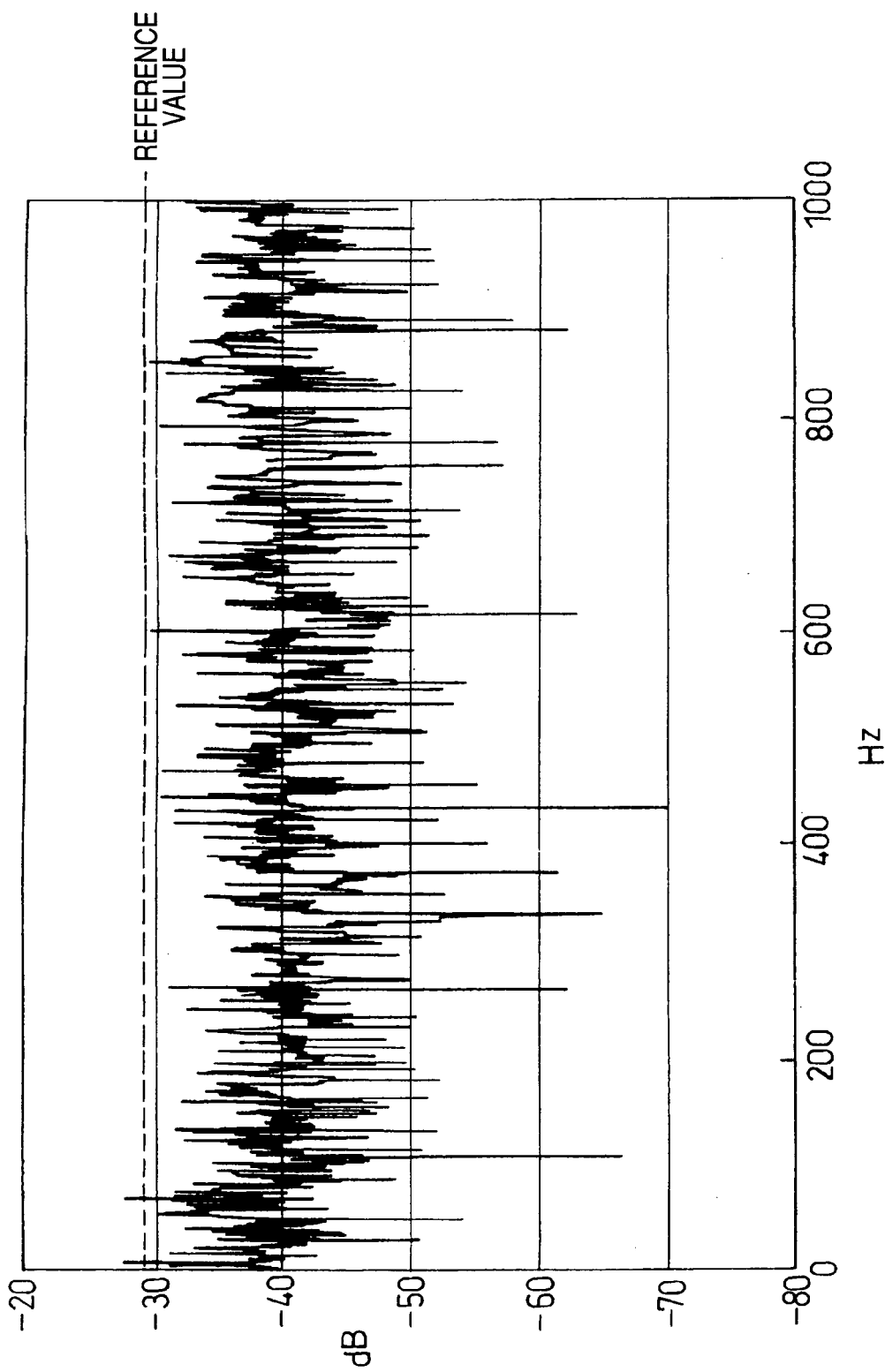
FIG. 10 is a graph showing a frequency spectrum when no abnormality is generated.
Figure 11:
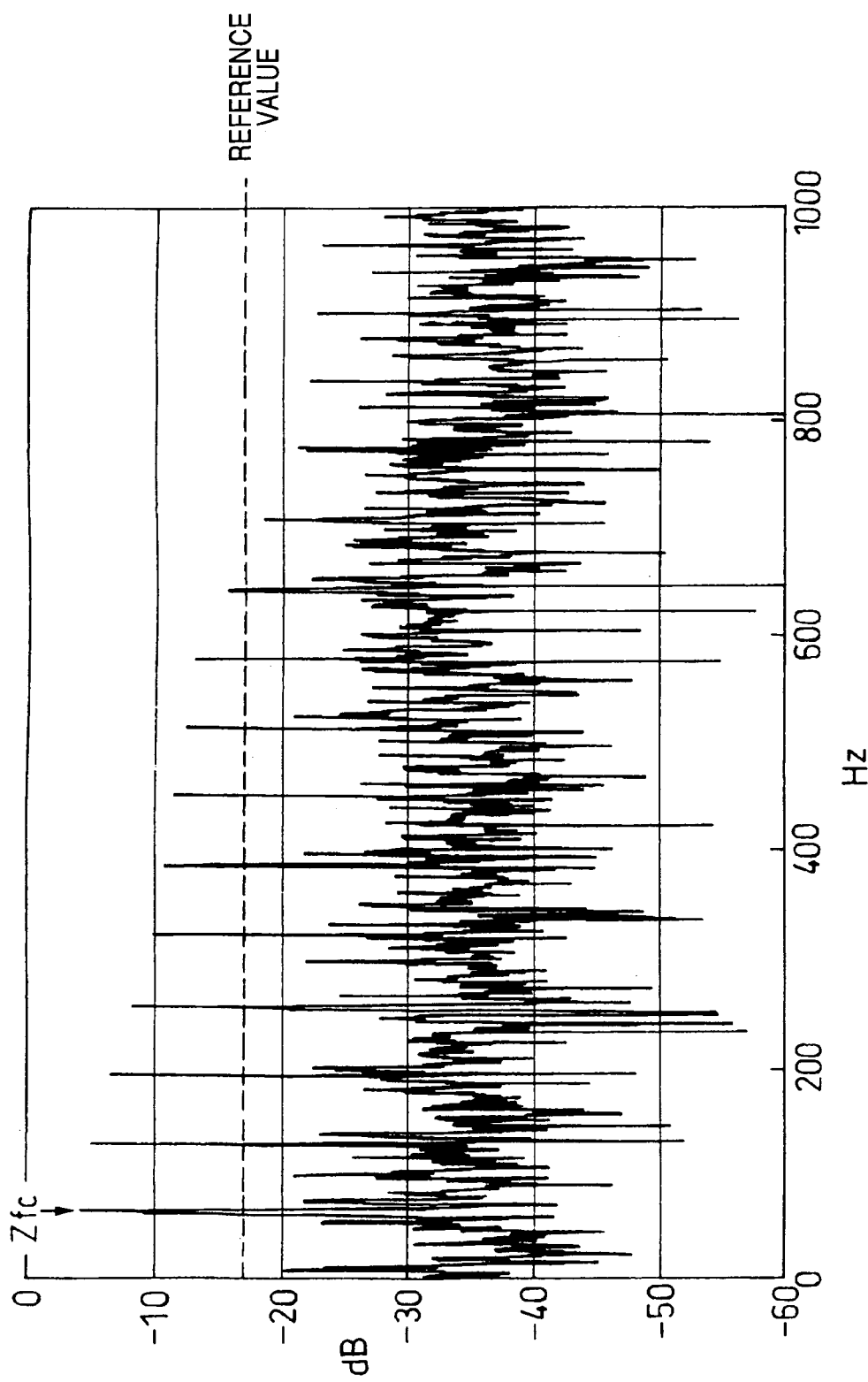
FIG. 11 is a graph showing a frequency spectrum when the abnormality is generated in an outer ring.

FIG. 10 is a graph showing the frequency spectrum when no abnormality is generated, and FIG. 11 is a graph showing the frequency spectrum when the abnormality is generated in the outer ring. In an example in FIG. 10, the reference value was derived as −29.3 dB from the envelope data. If the inner ring flaw component Si(Zfi), the outer ring flaw component So (Zfc), the rolling element flaw component Sb (2fb), and the retainer flaw component Sc (fc) are compared with a line of the reference value depicted in FIG. 10, the levels of all components are smaller than the reference value. As a result, it is decided that this bearing is normal. In contrast, in the case in FIG. 11, since the outer ring flaw component So (Zfc) is protruded largely from the reference value, it can be decided that the abnormality is generated in the outer ring of the bearing.

Figure 12:
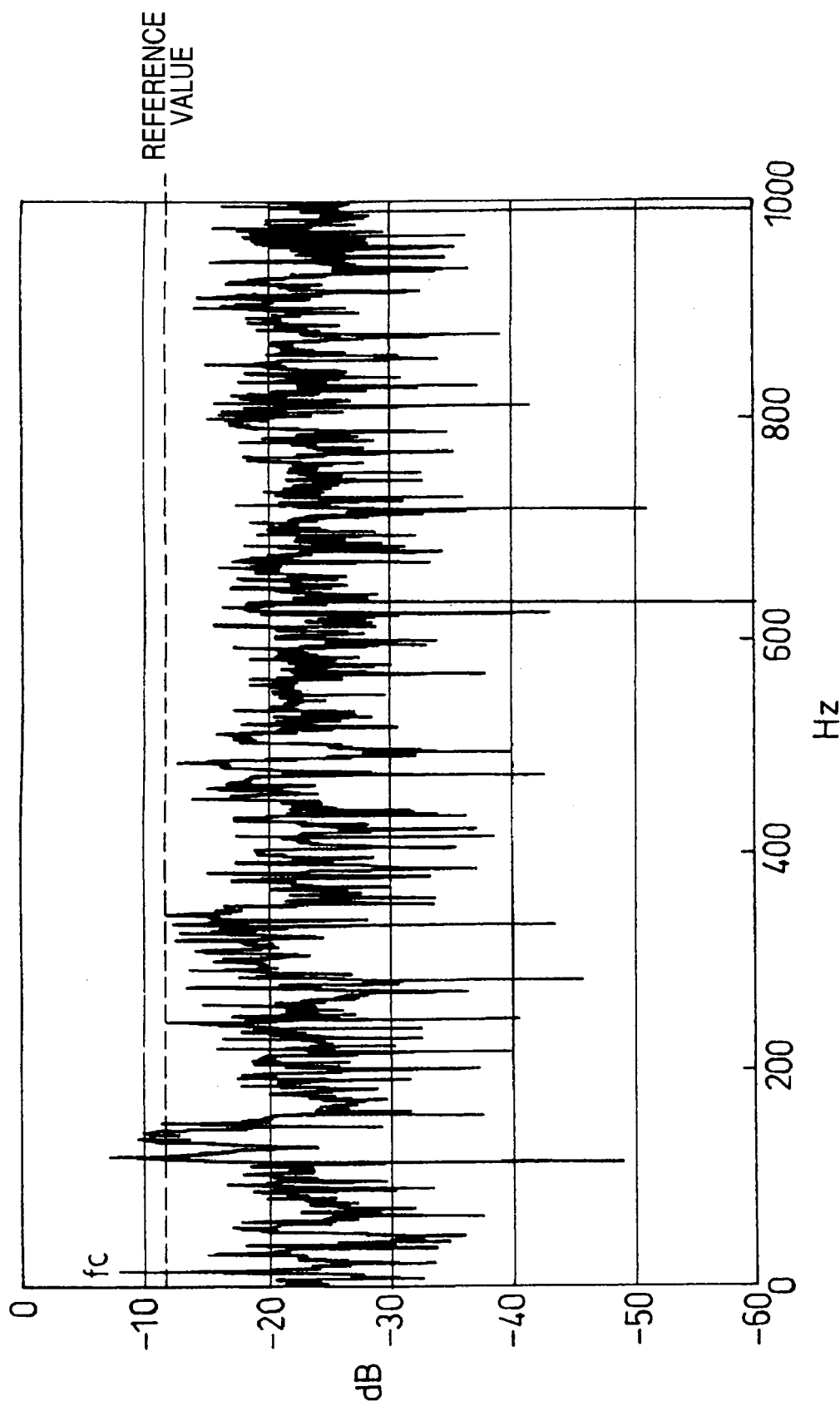
FIG. 12 is a graph showing a relationship between the frequency spectrum and a reference value when a retainer has a flaw.

Also, FIG. 12 is a graph showing a relationship between the frequency spectrum and the reference value when the retainer has the flaw. In FIG. 12, a peak that is larger than the reference value is observed at a frequency fc corresponding to the flaw of the retainer. In this manner, since the presence or the absence of the peak of the generated frequency can be decided by the comparison between levels in the frequencies due to the bearing and the reference value, even a small peak shown in FIG. 12 can be diagnosed appropriately.

Here, the root-mean-square value is employed, but either a mean value such as the running means, or the like or a peak factor (=peak level/mean value) may be employed.

Figure 13:
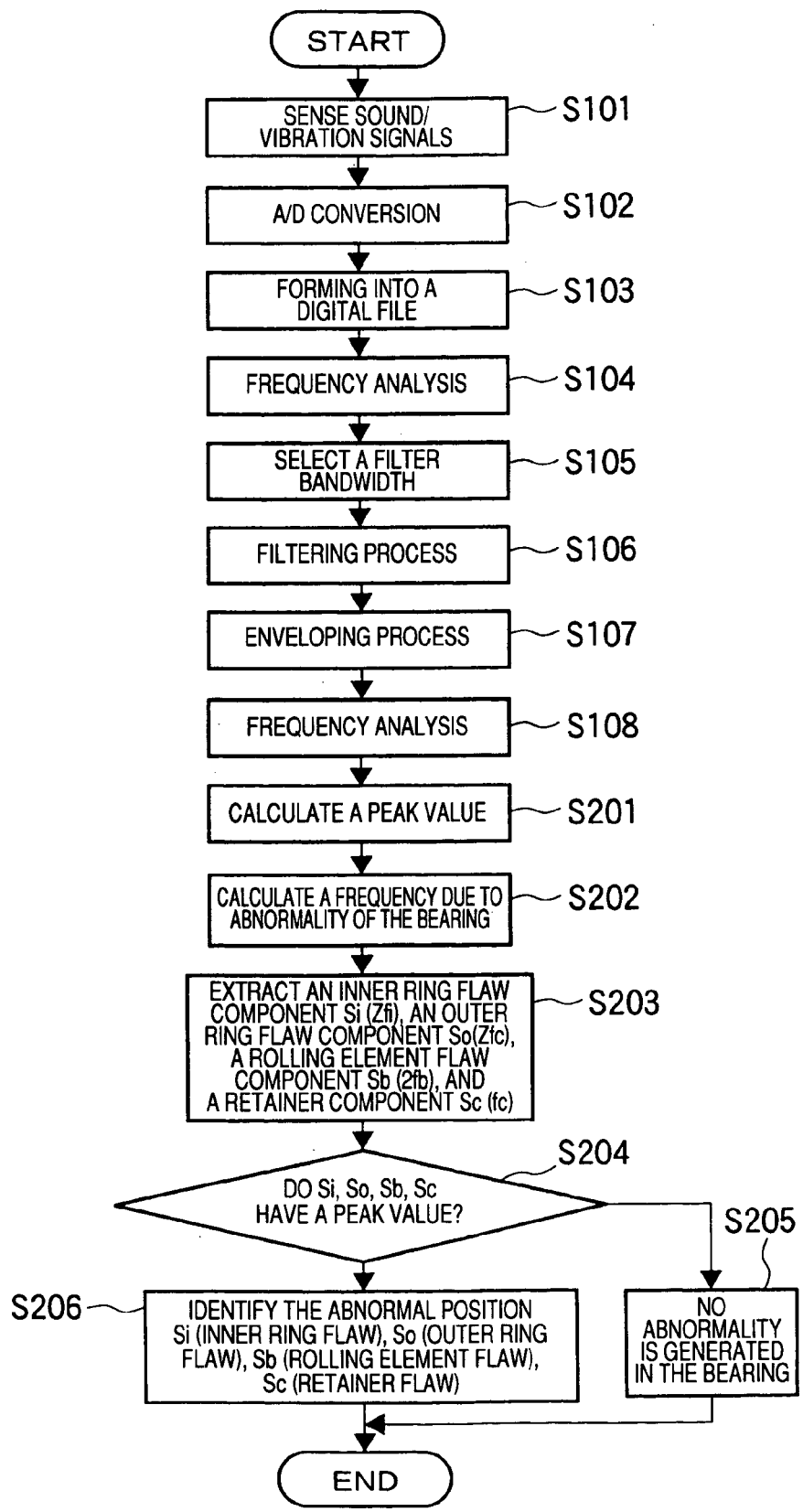
FIG. 13 is a flowchart showing a process flow in a second method.

(2) Method of calculating a peak of the spectrum and then comparing a peak frequency and an abnormal frequency The present method calculates the frequency components generated at the time of abnormality based on the expressions in FIG. 4. Then, it is collated whether or not the peaks, which exceed a predetermined occurring number of times or exceeds the reference value, among the frequency spectrum calculated by the comparing/deciding portion 36 correspond to the frequency components at which the abnormality occurs. Then, explanation will be made in detail with reference to a flowchart shown in FIG. 13 hereunder.

Since the process flows up to step S108 are similar to those set forth in the method (1), their explanation will be omitted herein. In the present method, first the peak value of the resultant frequency spectrum is calculated (step S201). Here, in order to derive the peak of the frequency, at first difference data indicating a difference between a level of a data point in each frequency component and a level of a preceding data point in each frequency component is calculated. Then, an inflection point at which a sign of the difference data is changed from plus to minus is found out, and then it is decided that the peak value appears at the frequency values in regarding to the difference data that give positive/negative criterions. In this case, only the frequency spectrum a ridge (inclination) of which shows a steep and sharp peak is selected as the object of the peak values that are necessary for the diagnosis. For this reason, only when a gradient is larger or smaller than a predetermined reference value (e.g., 1 or −1), it is decided that the frequency spectrum gives the peak.

Figure 14:
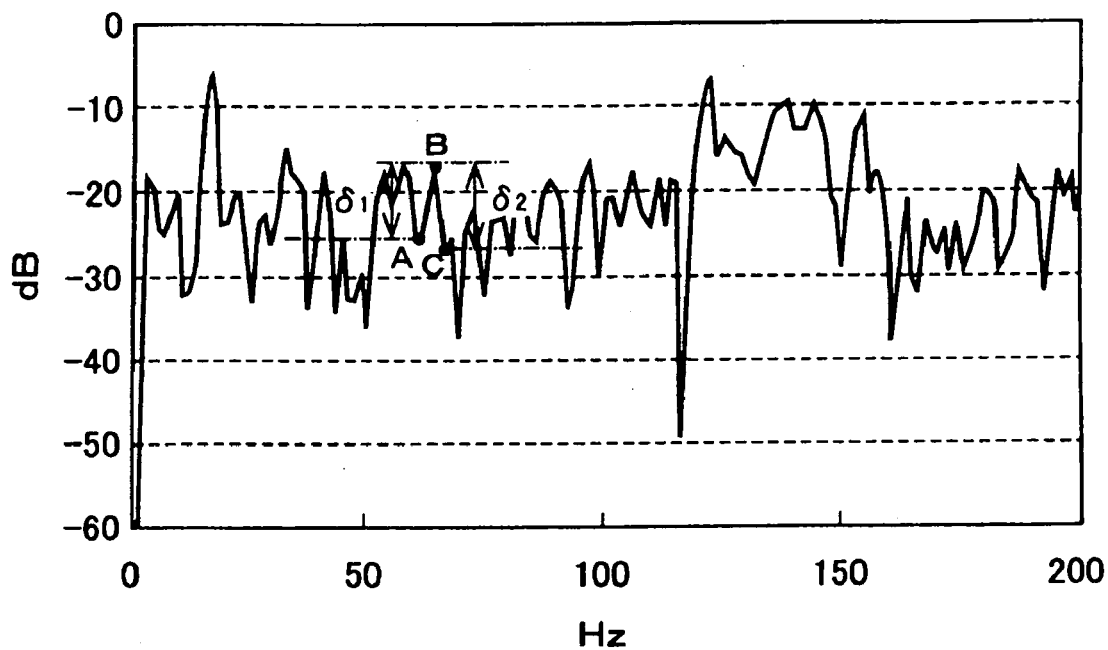
FIG. 14 is a view explaining the second method.

FIG. 14 is a view showing the frequency spectrum. In FIG. 14, a point B out of three successive points A ($X_0,Y_0$), B ($X_1,Y_1$), C ($X_2,Y_2$) gives the peak. In this case, since difference data $\delta_1$ between A and B is given as $\delta_1=Y_1-Y_0>0$ and the difference data $\delta_2$ between B and C is given as $\delta_2=Y_2-Y_1<0$, the difference data is changed from positive to negative. Then, if a gradient $(Y_1-Y_0)/(X_1-X_0)>1$ or a gradient $(Y_2-Y_1)/(X_2-X_1)<-1$ is satisfied here, it is decided that the point B gives the peak.

Then, the abnormal frequency is calculated from the specification of the bearing based on FIG. 4 (step S202). Then, the levels of the abnormal frequency components of respective members corresponding to the calculated frequency, i.e., the inner ring flaw component Si (Zfi), the outer ring flaw component So (Zfc), the rolling element flaw component Sb (2fb), and the retainer flaw component Sc (fc) are extracted (step S203). Then, it is decided by comparing the peak frequency with the frequencies generated at the time of abnormality whether or not the peak frequency agrees with the calculated abnormal frequency (step S204). Then, if a certain peak corresponds to the abnormal frequency, it is decided that the abnormality is generated in the member that corresponds to the concerned abnormal frequency (step S206). In contrast, if the peak corresponds to no frequency, it is decided that no abnormality is generated (step S205).

(3) Method of using a fundamental frequency and a particular harmonic

The present method compares peak frequencies of a primary value as a fundamental frequency of the abnormal frequency component, a secondary value having a twice frequency of the fundamental frequency, and a quaternary value having a quadruple frequency of the fundamental frequency with the frequencies generated at the time of abnormality respectively, and then decides finally that the abnormality is generated if it is decided that the abnormality is generated at at least two frequencies, or decides that no abnormality is generated if the frequency at which it is decided that the abnormality is generated is one or less. Then, explanation will be made in detail with reference to FIG. 15 hereunder.

Figure 15:
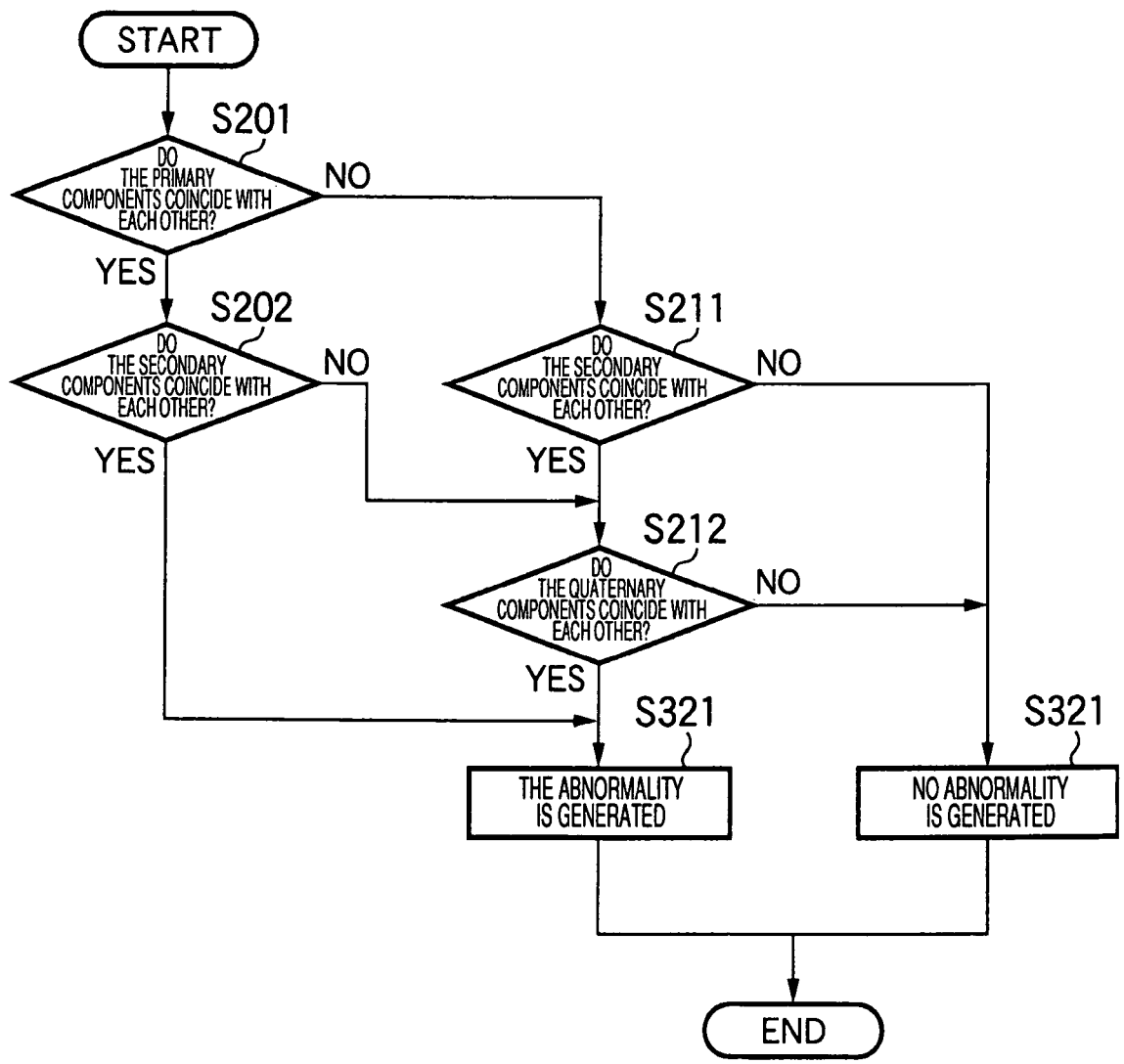
FIG. 15 is a flowchart showing a process flow in a third method.

The process flow required until the frequency spectrum is calculated and the frequencies generated due to the abnormality are calculated is similar to the process flow in the method (1). In the present method, as shown in FIG. 15, first it is decided in the comparison whether or not the spectrum value exceeds the reference value at the frequency of the fundamental component (primary component) generated at the time of abnormality (step S301). If the spectrum value exceeds the reference value, it is decided that the primary components coincide with each other. Then, the process goes to step S302. In contrast, if the primary components do not coincide with each other, the process goes to step S311.

In step S302, it is decided whether or not the spectrum value exceeds the reference value at the frequency of the secondary component that has the twice frequency of the fundamental component generated at the time of abnormality. If the spectrum value exceeds the reference value, it is decided that the secondary components coincide with each other. Then, in step S322, it is decided finally that the abnormality is generated in the concerned location. In contrast, in S302, if the secondary components do not coincide with each other, the process goes to step S312.

Also, in step S311, it is decided whether or not the spectrum value exceeds the reference value at the frequency of the secondary component that has the twice frequency of the fundamental component generated at the time of abnormality. If the spectrum value exceeds the reference value, it is decided that the secondary components coincide with each other. Then, the process goes to step S312. In contrast, if the secondary components do not coincide with each other, the process goes to step S321, wherein it is decided finally that the abnormality is not generated in the concerned location.

In step S312, it is decided whether or not the spectrum value exceeds the reference value at the frequency of the quaternary component that has the quadruple frequency of the fundamental component generated at the time of abnormality. If the spectrum value exceeds the reference value, it is decided that the quaternary components coincide with each other. Then, in step S322, it is decided finally that the abnormality is generated in the concerned location. In contrast, if the quaternary components do not coincide with each other, it is decided finally that the abnormality is not generated in the concerned location.

Figure 16:
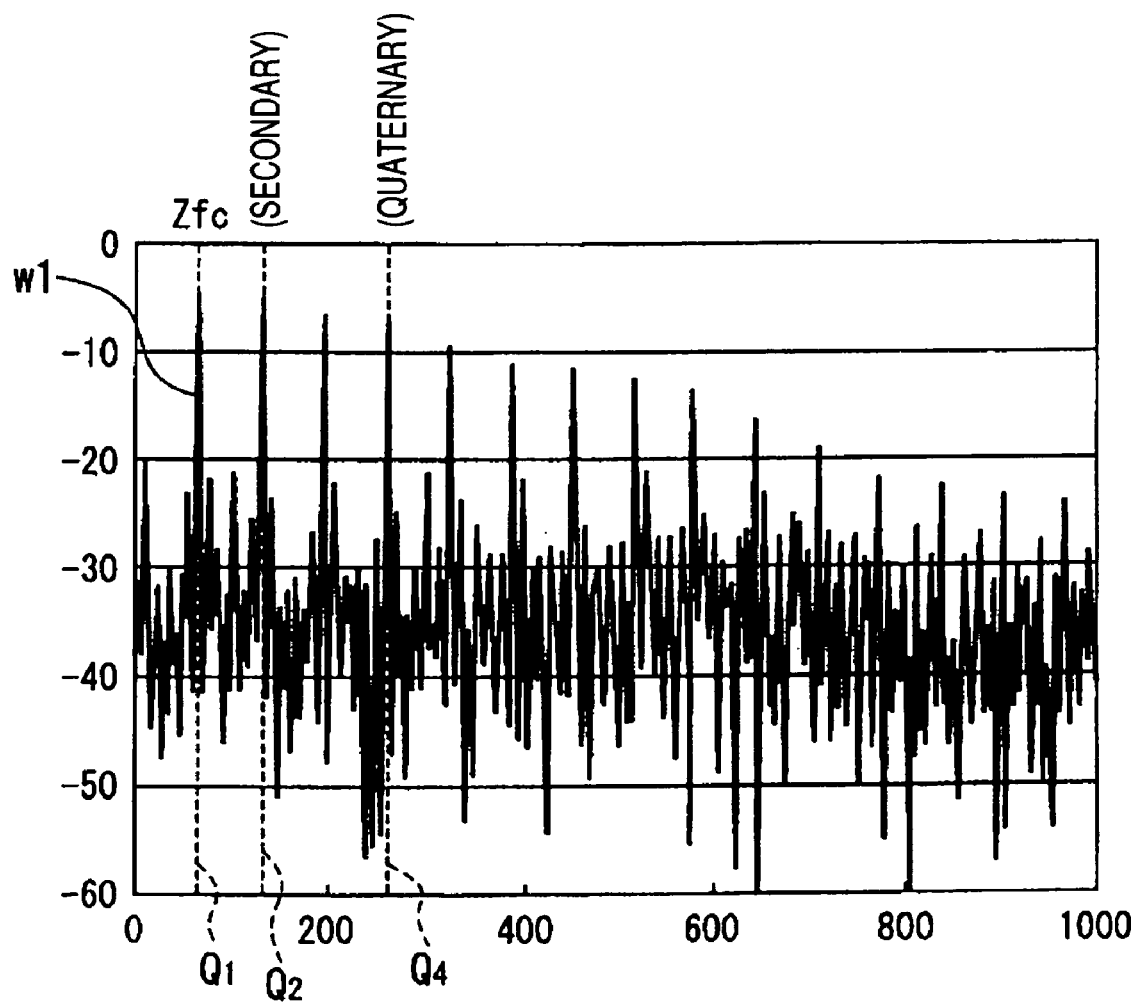
FIG. 16 is a view showing a frequency spectrum when an outer ring has the flaw.

FIG. 16 is a view showing the frequency spectrum when the outer ring has the flaw. It is understood that harmonics that are the natural-number multiple of Zfc as the fundamental frequency are observed. It is appreciated that, if the reference value is −10 dB in this case, the spectrum value exceeds the reference value at all the primary, secondary, and quaternary components. Therefore, according to the process in the present method, it is decided that the abnormality is generated in the outer ring.

Normally, such a situation may be considered that a large peak generated accidentally due to the influence of the noise, or the like is observed at the frequencies corresponding to the abnormality. According to the process in the present method, if the peak value does not exceed the reference value at at least two frequencies out of the primary, secondary, and quaternary components, it is not decided that the abnormality is generated. Thus, it is possible to reduce a possibility of misjudgment.

In the flowchart shown in FIG. 15, the comparison is made in order of the primary, secondary, and quaternary components. But the comparison is made in order of the larger peak level. In this case, if the largest peak is smaller than the reference value, it can be decided at that time that no abnormality is generated, and thus a calculation time can be shortened. Also, a combination of the primary value, the secondary value, and the tertiary value or a combination of the secondary value, the quaternary value, and the sexenary value may be used as the combination of frequency components.

Figure 17:
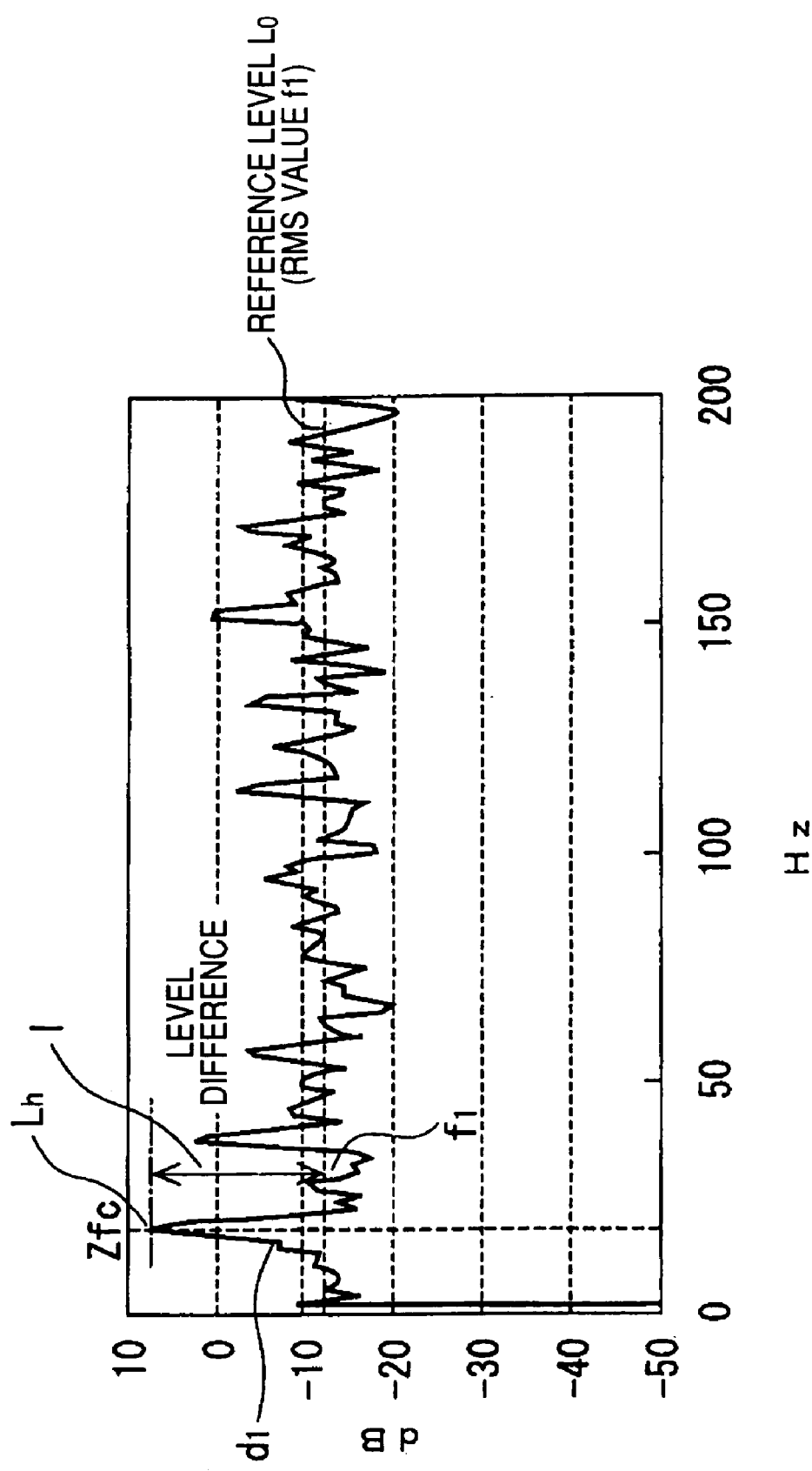
FIG. 17 is a view explaining a fourth method.

(4) Method conducting an abnormality diagnosis and estimating a degree of the damage In the methods (1) to (3), the presence or absence of the abnormality is diagnosed. But a size of the damage can be estimated as follows. FIG. 17 is a view showing the frequency spectrum after the enveloping process. In FIG. 17, the large peak is observed at the frequency Zfc, and thus it is understood that the damage is generated in the outer ring. A size of the damage generated in the outer ring in which the abnormality occurs can be estimated by comparing a peak value Ln at this Zfc and a reference level Lo as a mean value of the overall frequency spectrum.

Figure 18:
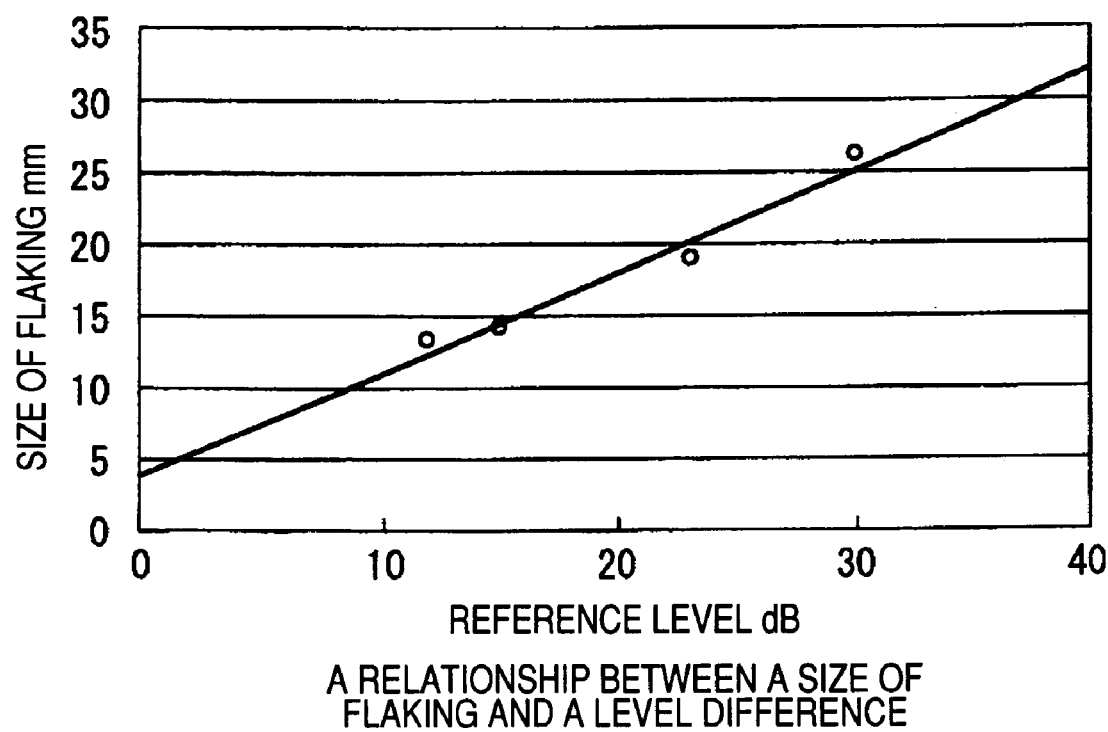
FIG. 18 is a graph showing a relationship between a size of flaking and a level difference between peaks appearing on the actually measured frequency spectrum data and a reference level.

FIG. 18 shows a relationship between a size of flaking and a level difference between peaks appearing on the actually measured frequency spectrum data d1 and the reference level when the flaking as the damage of the raceway ring is generated in the rolling bearing. In this manner, normally the level difference is increased in proportion to a size of the damage. Therefore, conversely the size of the damage can be estimated if the level difference between the peak on the actually measured frequency spectrum data d1 and the reference level is sensed. In this event, an increase of the peak level on the actually measured frequency spectrum data d1 becomes most conspicuous at the peak that corresponds to the primary value of the frequency components. Therefore, when the abnormality is sensed, an extent of the damage can be estimated by calculating a level difference I between a primary value Ln of the harmonic components and a reference level $L_0$. Thus, an exchange timing of the damaged parts can be decided in response to the extent of the damage. As a result, exchange of the parts can be carried out at an appropriate timing without the excessive exchange of parts or maintenance, and thus an upkeep cost can be reduced.

(5) Method of using a level difference of a natural-number multiple harmonic component of the fundamental frequency as a reference value The present method counts the number of times 2, 3, 4, . . . , n-degree levels having 2, 3, 4, . . . , n-tuple frequencies of the fundamental frequency respectively exceed the reference value of the primary level as the fundamental frequency of the abnormal frequency components, and then decides that the abnormality is generated when these 2, 3, 4, . . . , n-degree levels exceed the reference value in a predetermined number or more. More particularly, the counting is carried out when the n-degree value is {(primary level)−(n−1-)·a} (dB) or more with respect to the primary level. Where a is an arbitrary value. Then, explanation will be made with reference to a flowchart shown in FIG. 19 hereunder.

Figure 19:
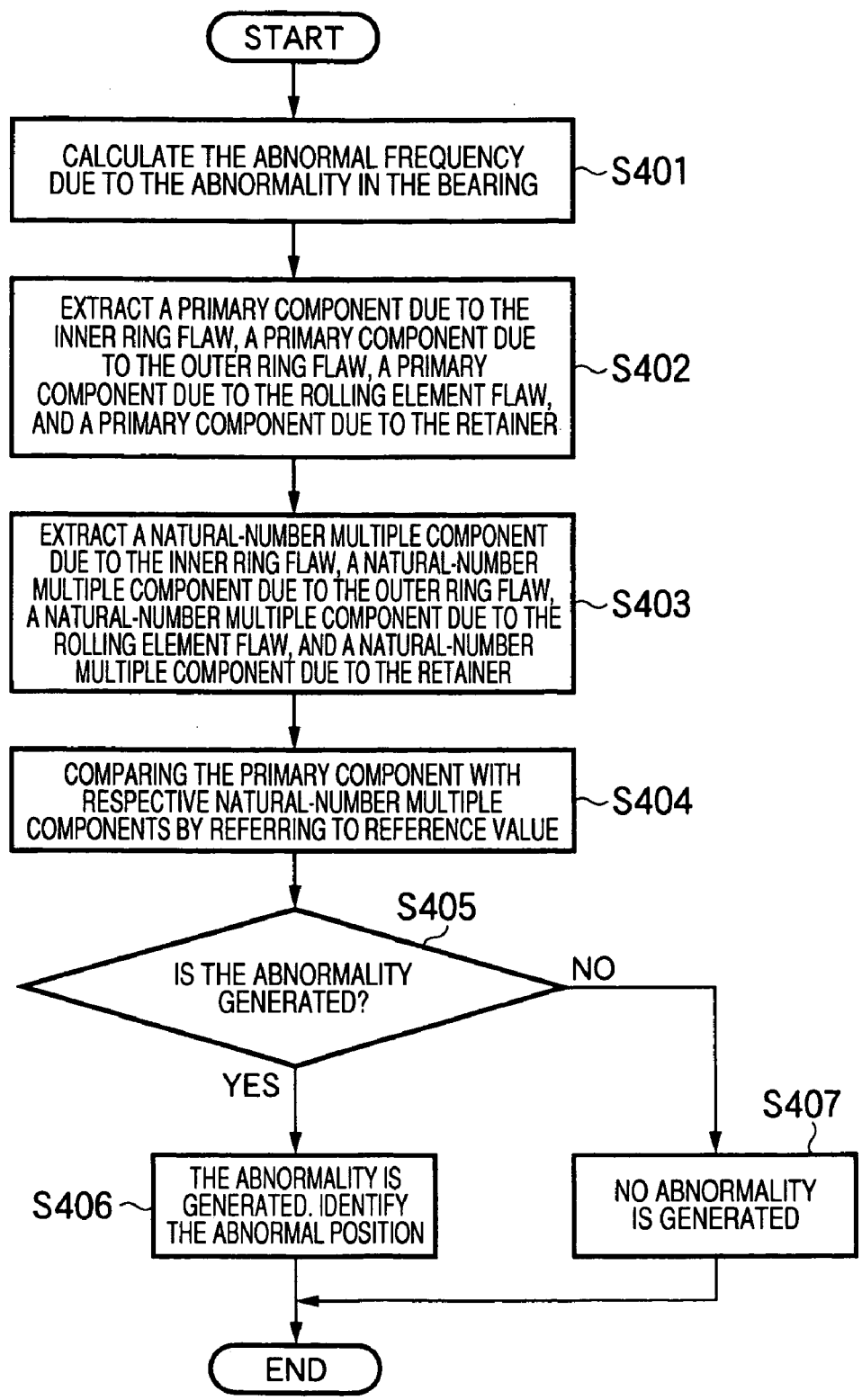
FIG. 19 is a flowchart showing a process flow in a fifth method.

FIG. 19 is a flowchart showing a process flow in the present method. In the present method, the processes required until the frequency spectrum is calculated are identical to the processes in step S101 to step S108 in the flowchart in FIG. 9. The processes in step S108 et seq. are shown in FIG. 19.

First, the abnormal frequency due to the abnormality in the bearing is calculated every part (outer ring, inner ring, rolling element, or retainer) of the bearing by referring to the expressions (step S401). Then, the level of the frequency spectrum corresponding to the abnormal frequency is extracted (step S402). Then, levels of the frequency spectra that correspond to the natural-number multiple (2, 3, . . . , n-tuple) frequencies of the abnormal frequency are extracted respectively (step S403). Here, assume that secondary, tertiary, quaternary, and quinary components having twice, thrice, quadruple, and quintuple frequencies of the abnormal frequency as the base are extracted.

Then, the levels of the secondary, tertiary, quaternary, and quinary components are checked on the basis of the primary component as the base (step S404). Here, if the levels of respective components exceed {(primary level)−3(n−1)} (dB), the count indicating that the abnormality is generated is executed. More particularly, the count indicating that the abnormality is generated is executed in respective components in following cases.

(level of the secondary component)>
(level of the primary component)−3
(level of the tertiary component)>
(level of the primary component)−6
(level of the quaternary component)>
(level of the primary component)−9
(level of the quinary component)>
(level of the primary component)−12

Then, the final abnormality decision is made by checking whether or not the count number of times indicating that the abnormality is present exceeds the predetermined number of times (step S405). Here, it is decided finally that the abnormality is generated step S406 if the count number of times indicating that the abnormality is present exceeds two times, while it is decided finally that no abnormality is generated step S407 if the count number of times is once or less.

Figure 20:
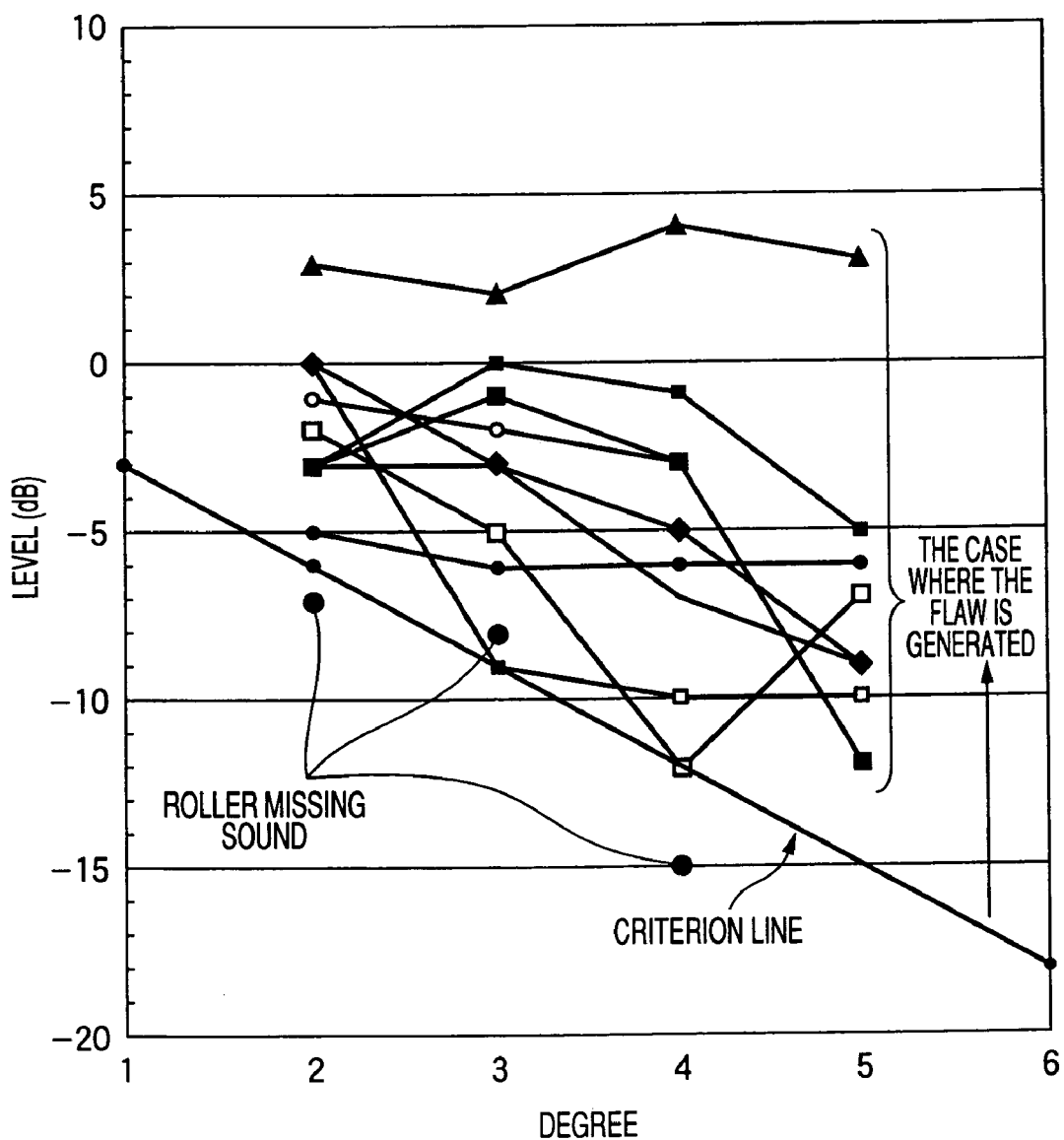
FIG. 20 is a view showing frequency spectrum levels and a reference line.

FIG. 20 is a view showing a relationship between a level of the frequency spectrum and a reference line when the inner ring of the cylindrical roller bearing (outer diameter 215 mm, inner diameter 100 mm, width 47 mm, and number of roller 14) is rotated at about 300 min$^{-1}$. In FIG. 20, a straight line is a criterion line obtained by connecting the above reference values by a line. In the case where the bearing has the flaw, the values of the secondary components or more are in excess of the criterion line, but the peak level of the secondary and quaternary compositions, which correspond to the roller missing sound also generated in the normal condition, fall below this criterion line. Since normally the higher order components of the roller missing sound (rolling element missing sound) are low rather than the case where the outer ring has the flaw, most of the sound values fall below this criterion line, as shown in FIG. 20. As a result, even when the peaks of the roller missing sound, or the like appear at the same frequencies as the case where the outer ring has the defect, it is possible to decide whether or not the bearing is abnormal or normal, with good precision by comparing the levels of the higher order components mutually.

(6) Method of using a square mean or a partial overall of a level every frequency band The present method executes the abnormality diagnosis by using not the peak level value itself of the frequency caused due to the abnormality but a square mean or a partial overall of the level of the frequency band containing the frequency caused due to the abnormality. Here, the square mean Vi and the partial overall Si are given by following equations. Where $V_{RMS}$ and $S_{OA}$ are the square mean and the partial overall in the full frequency band respectively. The overall denotes a total sum in the particular specified interval.

<Formula 1>

$$Vi = \frac{1}{m}\sum_{k=1}^{m}(P_k - \bar{P}_m)^2 \quad (1)$$

$$Si = \sum_{k=1}^{m} P_k \quad (2)$$

$$V_{RMS} = \frac{1}{N}\sum_{i=1}^{N}(P_i - \bar{P})^2 \quad (3)$$

$$S_{OA} = \sum_{i=1}^{N} P_i \quad (4)$$

where $$N \cdot \Delta f < \frac{f_s}{2} \quad (5)$$

m: cut-out frequency bandwidth (number of data)
/Pm: spectrum mean value in the interval m
Pi: spectrum value at the frequency i
/P: spectrum mean value in the interval N
fs: sampling frequency
Δf: width of neighboring frequencies (frequency resolution)

Figure 21:
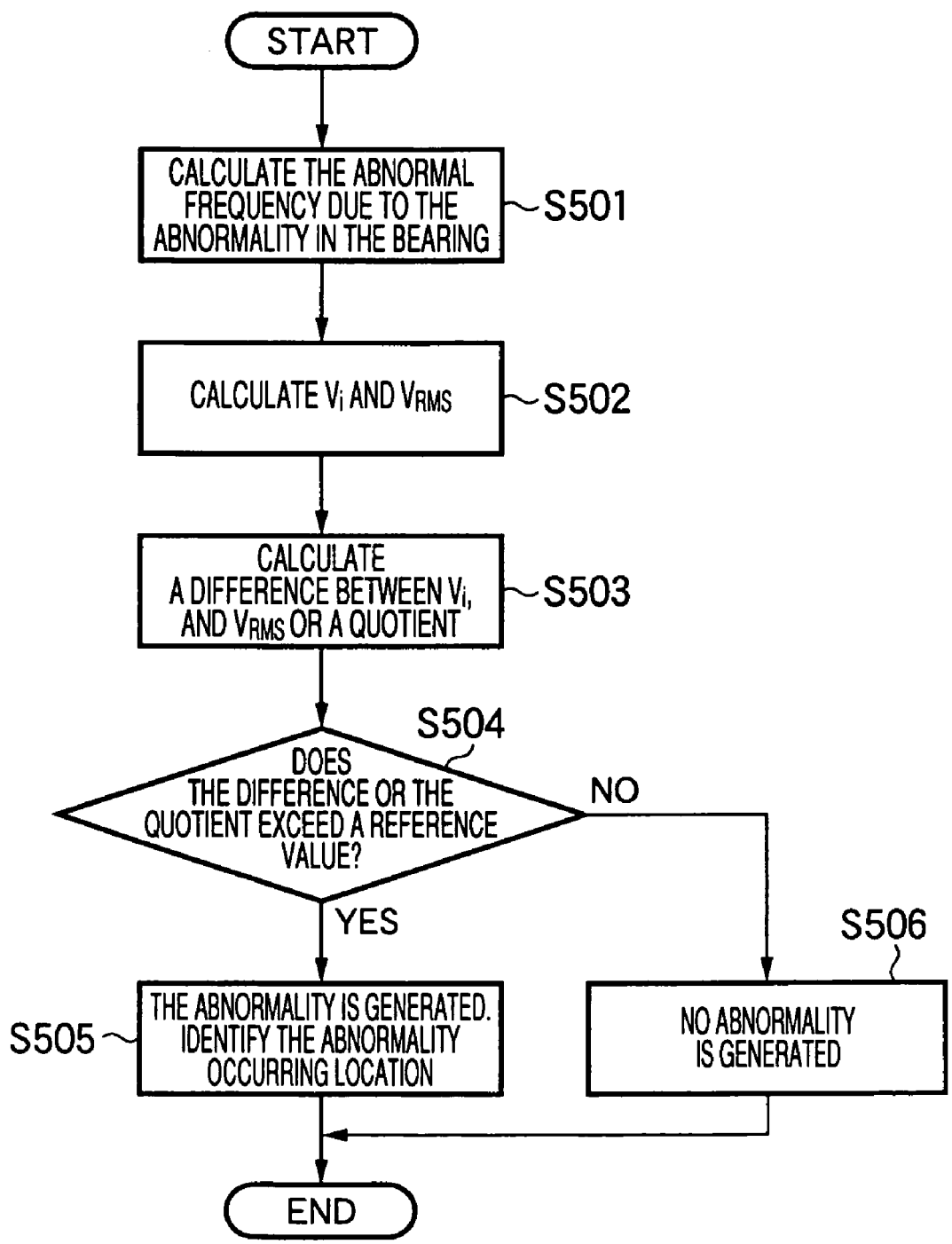
FIG. 21 is a flowchart showing a process flow in a sixth method.

FIG. 21 is a flowchart showing a process flow in the present method. In the present method, the processes required until the frequency spectrum is calculated are identical to the processes in step S101 to step S108 in the flowchart in FIG. 9. The processes in step S108 et seq. are shown in FIG. 21.

First, the abnormal frequency caused due to the abnormality in the bearing is calculated by referring to the expressions shown in FIG. 4 every part (outer ring, inner ring, rolling element, or retainer) of the bearing (step S501). Then, the square mean (Vi) or the partial overall (Si) in the frequency band containing the calculated frequency, and a normalized value as the square mean ($V_{RMS}$) or the partial overall ($S_{OA}$) of the overall frequency spectrum band are calculated (step S502). Then, a quotient value obtained by dividing the square mean (Vi) or the partial overall (Si) in the primary component bandwidth by the normalized value ($V_{RMS}$ or $S_{OA}$) or a difference value between them is calculated (step S503).

Then, it is decided whether or not the quotient value or the difference value is within the normal range, more particularly whether or not the quotient value or the difference value exceeds a predetermined value, by comparing/collating the quotient value or the difference value with the saved reference data (step S504). Then, if the quotient value or the difference value is more than or less than a predetermined reference value, it is decided that the abnormality is generated, and then the abnormality occurring location is identified based on the frequency band (step S505). Here, it may be determined by the actual measurement that the abnormality decision should be made depending on whether the above value is more than the predetermined reference value or is less than the predetermined reference value. Except the above case, it is decided that no abnormality is generated (step S506).

Figure 22:
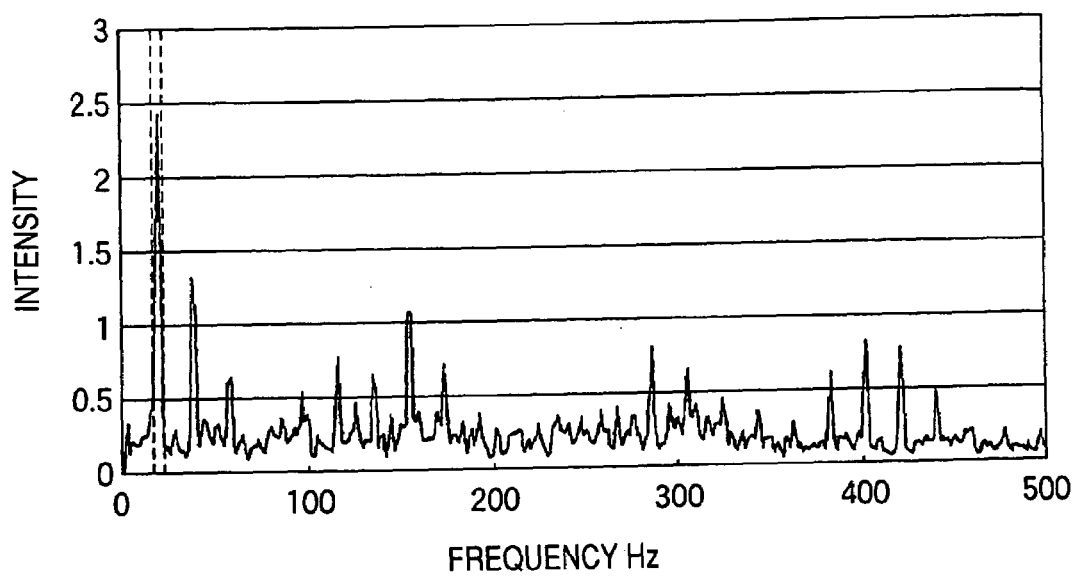
FIG. 22 is a graph showing a frequency spectrum when the abnormality is generated in the outer ring.
Figure 23:
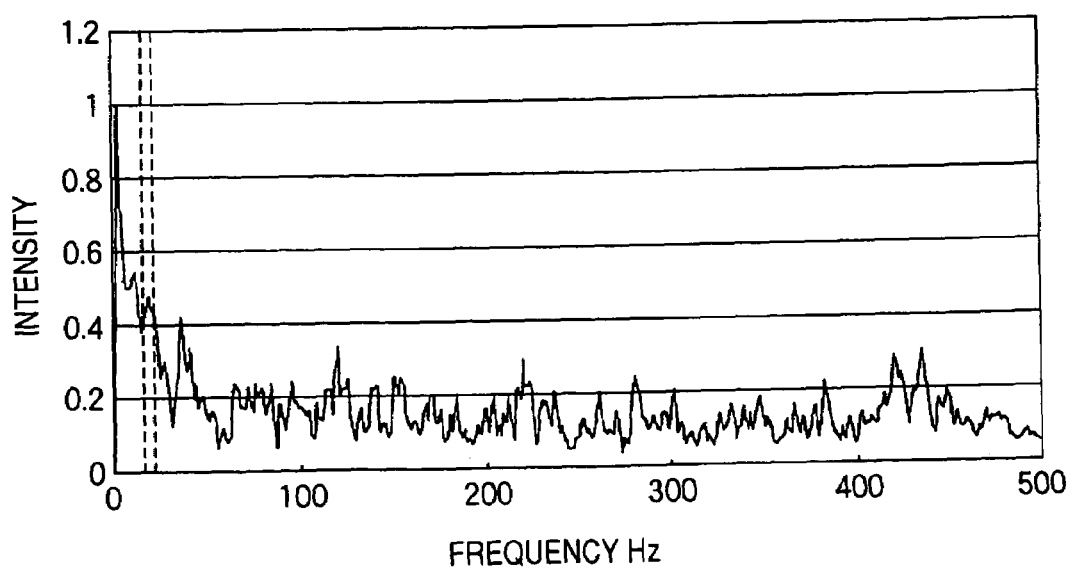
FIG. 23 is a graph showing a frequency spectrum when no abnormality is generated in the outer ring.

The above method will be explained by referring to the actual measured result. FIG. 22 is a graph showing the frequency spectrum when the abnormality is generated in the outer ring, and FIG. 23 is a graph showing the frequency spectrum when no abnormality is generated in the outer ring. The abnormal peak frequency band is present near the left end (around 10 to 20 Hz) of FIG. 22. The square mean value Va of the overall spectrum is 0.016. Also, the square mean value Vn of the overall spectrum corresponding to FIG. 20 is 0.008. Suppose that the frequency bandwidth extracted with respect to the abnormal frequency band (fundamental frequency) generated due to the flaw of the outer ring is 2 Hz, the value derived by normalizing the square mean value by V in this bandwidth is 90.78 in the case in FIG. 22 and is 38.47 in the case in FIG. 23. It is understood that, when the abnormality is generated, the normalized value is about 2.4 times larger than that in the normal condition. Therefore, if a predetermined threshold value is provided either between 90.78 and 38.47 or to a ratio between the normal condition and the abnormal condition, it can be decided that the abnormality is generated in the outer ring when the normalized value is larger than the threshold value.

Figure 24:
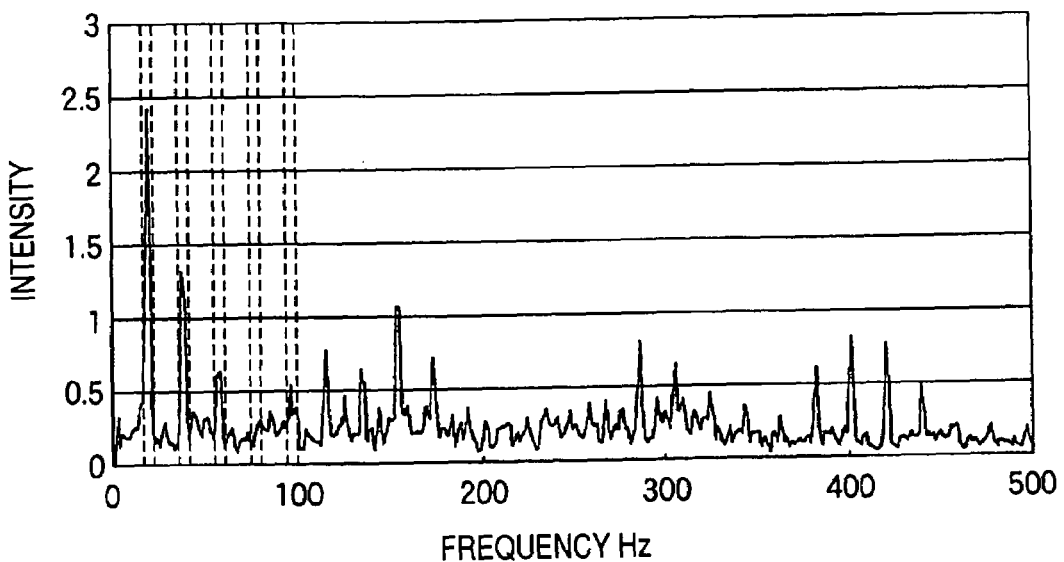
FIG. 24 is another graph showing a frequency spectrum when the abnormality is generated in the outer ring.
Figure 25:
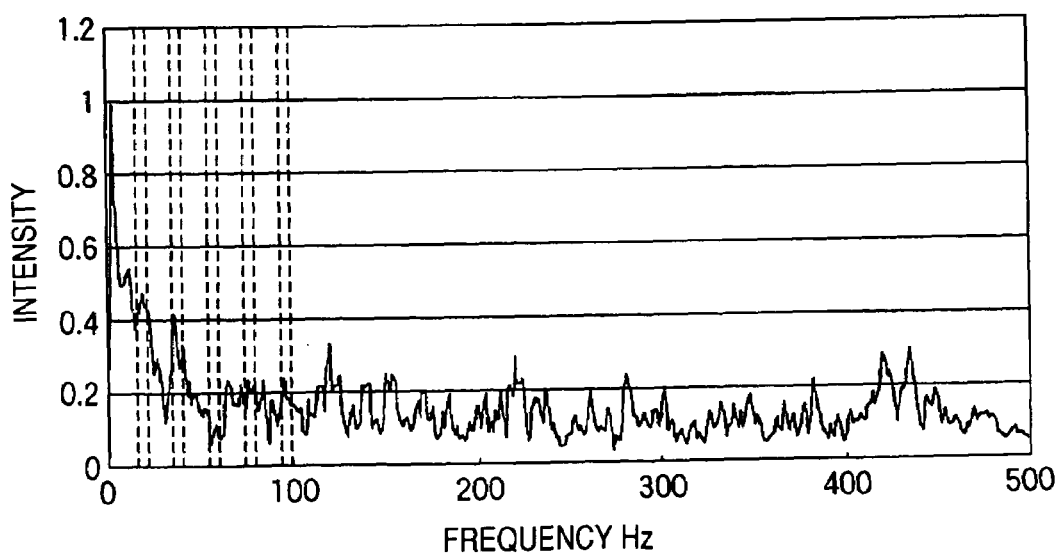
FIG. 25 is another graph showing a frequency spectrum when no abnormality is generated in the outer ring.
Figure 26:
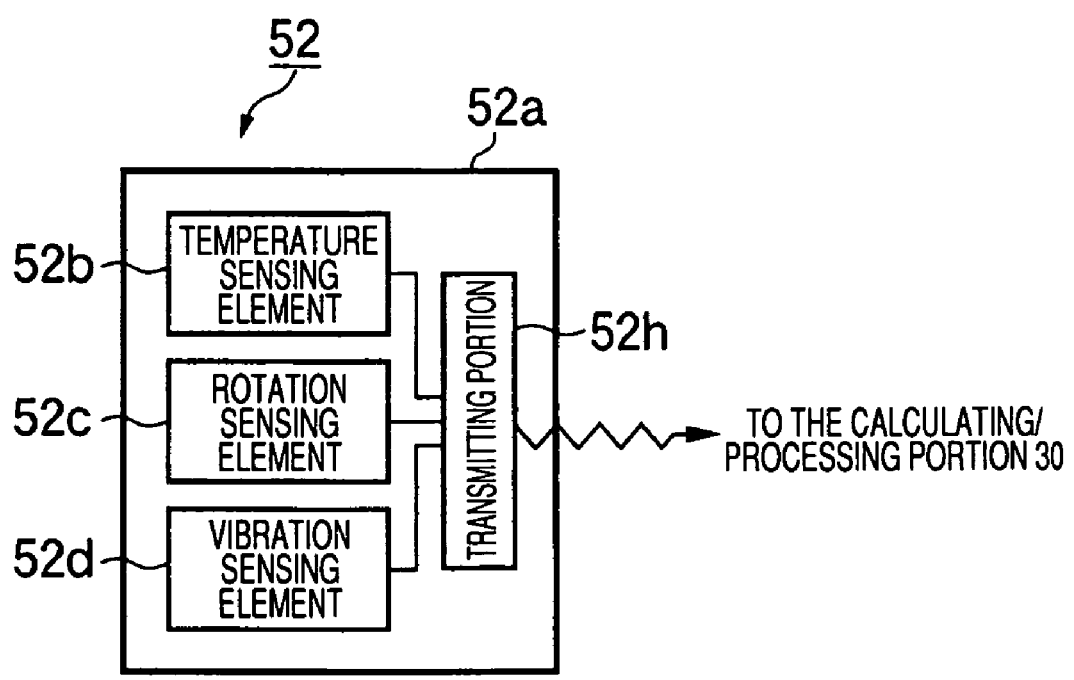
FIG. 26 is a block diagram showing an internal configuration of a sensor unit in a railway vehicle abnormality diagnosis system according to a second embodiment of the present invention.

Meanwhile, FIG. 24 and FIG. 25 show examples in which plural bands are employed. FIG. 24 is a graph showing an envelope frequency spectrum of the machinery facility having the roller bearing, which has the damage in its outer ring, and the normal gear (the number of teeth; 31). In FIG. 24, five frequency peaks are observed and also the secondary component to the quinary component are observed in every integral multiple of the fundamental frequency. FIG. 25 shows an observed data in the normal condition corresponding to FIG. 24, and no singular frequency is found.

Then, the above approach is also applied to the data in FIG. 24 and FIG. 25. The value derived by normalizing a sum of the square mean values in respective bands of the fundamental frequency to the quinary component, which are generated due to the flaw of the outer ring, by the square mean value of the overall spectrum is given as 11.64 in the case in FIG. 24 and 5.19 in the case in FIG. 25. Here, the quinary harmonic means the fifth peak that is counted from the fundamental frequency. It is understood that, when the abnormality is generated, the normalized value is about 2.2 times larger than that in the normal condition. Therefore, if a predetermined threshold value is provided either between 11.64 and 5.19 or to a ratio between the normal condition and the abnormal condition, it can be decided that the abnormality is generated in the outer ring when the normalized value is larger than the threshold value.

The above processes are the particular processing pattern when the decision to check whether or not the abnormality is caused is made by the comparing/deciding portion 36. The comparing/deciding portion 36 may be constructed to execute the abnormality diagnosis by using plural deciding methods out of these methods. In order to improve an accuracy of the abnormality diagnosis, it is preferable that the abnormality should be decided by using plural deciding methods.

The data accumulating/outputting portion 38 is a saving portion for saving the decision result of the comparing/deciding portion 36, and is composed of a hard disc, a memory medium, or the like. The data accumulating/outputting portion 38 outputs the decision result to a controlling portion 41 and a result outputting portion 42. The data accumulating/outputting portion 38 is constructed to output the result to the controlling/processing portion 40 in real time, but is not limited to this. The data accumulating/outputting portion 38 may be constructed to output periodically to the controlling/processing portion 40, or may be constructed to output the result only when the result is necessary for an operation of the controlling/processing portion 40 (when it is decided that the abnormality occurs), as explained in the following.

The controlling/processing portion 40 has the result outputting portion 42 as a displaying means for displaying the analyzed result or the decision result of the calculating/processing portion 30 in a predetermined display mode, and the controlling portion 41 for feeding back a control signal S1 to a control system, which controls an operation of a driving system of the vehicle into which the bearing 21 is incorporated, in response to the decision result of the comparing/deciding portion 36.

More specifically, the result outputting portion 42 informs of the analyzed result or the decision result of the calculating/processing portion 30 by a monitor, an image display, or a printing output to a printer, and also informs of the result by flashing an alarm lamp or operating an alarm when the decision result of the calculating/processing portion 30 indicates that the abnormality is generated.

For example, when the decision result of the calculating/processing portion 30 indicates that the abnormality is generated, the controlling portion 41 feeds a control signal S1 instructing a travel stop of the vehicle, a reduction of the speed, or the like to a travel controller of the vehicle in answer to a degree of the abnormality. In the present embodiment, a plurality of sensor units 22 sense continuously a condition of the bearing in the bearing unit, and the calculating/processing portion 30 executes the abnormality diagnosis sequentially based on the sensed data. Therefore, the controlling/processing portion 40 informs immediately of the abnormality when the abnormality occurs, and then performs the control of the vehicle That is, a flow of sensing, analyzing, deciding and result outputting processes are carried out in real time.

Now, the sensor unit 22 may be constructed to execute the measurement constantly or may be constructed to execute the measurement every predetermined time. Also, instead of the real-time abnormality diagnosis, only the measurement and the accumulation of measured data may be executed during the traveling of the vehicle and then the analysis may be executed later in another location. For example, only the measurement may be carried out in the daytime and then the analysis, the decision, and the result output may be carried out together with in the nighttime.

As explained above, the axle bearing unit abnormality diagnosis system 1 in the present embodiment is the abnormality diagnosis system that diagnoses the presence or absence of the abnormality of the bearing unit of the railway vehicle axle bearing unit, and includes the sensing/processing portion 20 having a plurality of sensing elements for outputting the signal generated from the bearing unit as the electric signal, the calculating/processing portion 30 performs the calculating process to execute the abnormality diagnosis of the bearing unit based on the output of the sensing/processing portion 20, the result outputting portion 42 for outputting the decision result from the calculating/processing portion 30, and the controlling portion 41 for feeding back the control signal to the control system of the railway vehicle based on the decision result.

Also, in the abnormality diagnosis system 1 in the present embodiment, the outputs of the sensor units 22 incorporated in advance into the bearings 21 are analyzed by respective analyzing portions 32, 33, 35 of the calculating/processing portion 30 to check whether or not the abnormality is caused due to the wear or the failure of the constituent parts of the bearing 21. Then, the abnormality diagnosis system 1 decides the presence or absence of the abnormality by comparing the analyzed result with the reference data prepared previously in the internal data saving portion 37.

Accordingly, this abnormality diagnosis system 1 can decide whether or not the abnormality due to the wear or the failure of the constituent parts of the sensor built-in bearing 21 is present. Therefore, the presence or absence of the abnormality can be decided in the normal condition of use not to decompose the sensor built-in bearing 21 itself or the railway vehicle itself containing the bearing 21. As a result, a frequency of overhauling/assembling operations that take a lot of time and labor can be reduced, and thus maintenance/administrative costs can be reduced.

Also, the decision is made mechanically based on the analysis and the comparison executed by specified calculating processes. Therefore, the decision is seldom varied owing to a degree of expertise or individual differences of the person in charge of inspection rather than the visual inspection in the prior art, and thus the reliability of the diagnosis to check the presence or absence of the abnormality can be improved.

Also, the sensor units 22 are installed directly into the outer ring, or the like as the constituent parts of the rotating body constituting the rolling bearing 21, and then the sensors can sense physical quantities generated from the rolling bearing 21 with high sensitivity. Therefore, such a possibility can be reduced that peaks of the frequency components of the sound or the vibration generated by other articles around the rolling bearing 21 exert a harmful influence upon an SN ratio of the signal sensed by the sensor, and thus improvement of analysis/decision precisions can be attained by improving the SN ratio of the output signal of the sensor.

As a consequence, such a possibility can be eliminated that, for example, the sensed signal of the sensor unit 22 is largely distorted by the peak of the frequency component of the noise generated when the railway vehicle passes over the rail joint, the vibration generated from the devices, and the like regardless of the bearing 21, and the like. Also, reduction of a computing load and reduction of a loss of time required for the analysis can be achieved by improving the SN ratio of the output signal of the sensor unit, and thus improvement of the analysis/decision precisions and the acceleration of the process can be achieved.

Also, in the present embodiment, since the amplifiers that amplify the sensor output respectively are built in the sensor unit 22, the output signal of the sensor unit 22 has already been amplified to have the large amplitude. Therefore, the influence of the noise superposed on the signal transmission path between the sensor unit 22 and the calculating/processing portion 30, or the like can be suppressed. As a result, reduction of a process precision due to the noise can be prevented, and thus the reliability of the abnormality diagnosis can be improved.

In this event, the abnormality diagnosis system 1 in the present embodiment diagnoses the presence or absence of the abnormality of the bearing in the bearing unit and the abnormality occurring location, but the system is not limited to this configuration. The system may be constructed to diagnose the flat portion of the axle, or may be constructed to diagnose the presence or absence of the abnormality of the gear in the bearing unit and the abnormality occurring location. Therefore, various large-size rotating bodies that take a lot of time and labor to remove and fit the parts can be chosen as the object of the abnormality diagnosis in the present invention.

As above, the approaches (1) to (6) are described as the particular processes of the abnormality diagnosis executed by the comparing/deciding portion 36 based on the vibration information. But the present invention is not limited to the above approaches. The abnormality diagnosis may be executed by analyzing the frequency spectrum by virtue of the cepstrum analysis.

<Second Embodiment>

Next, a machinery facility abnormality diagnosis system according to a second embodiment of the present invention will be explained in detail hereunder. In this case, the same reference symbols are affixed to the portions similar to those in the first embodiment, and thus their redundant explanations will be omitted or simplified hereunder.

Figure 27:
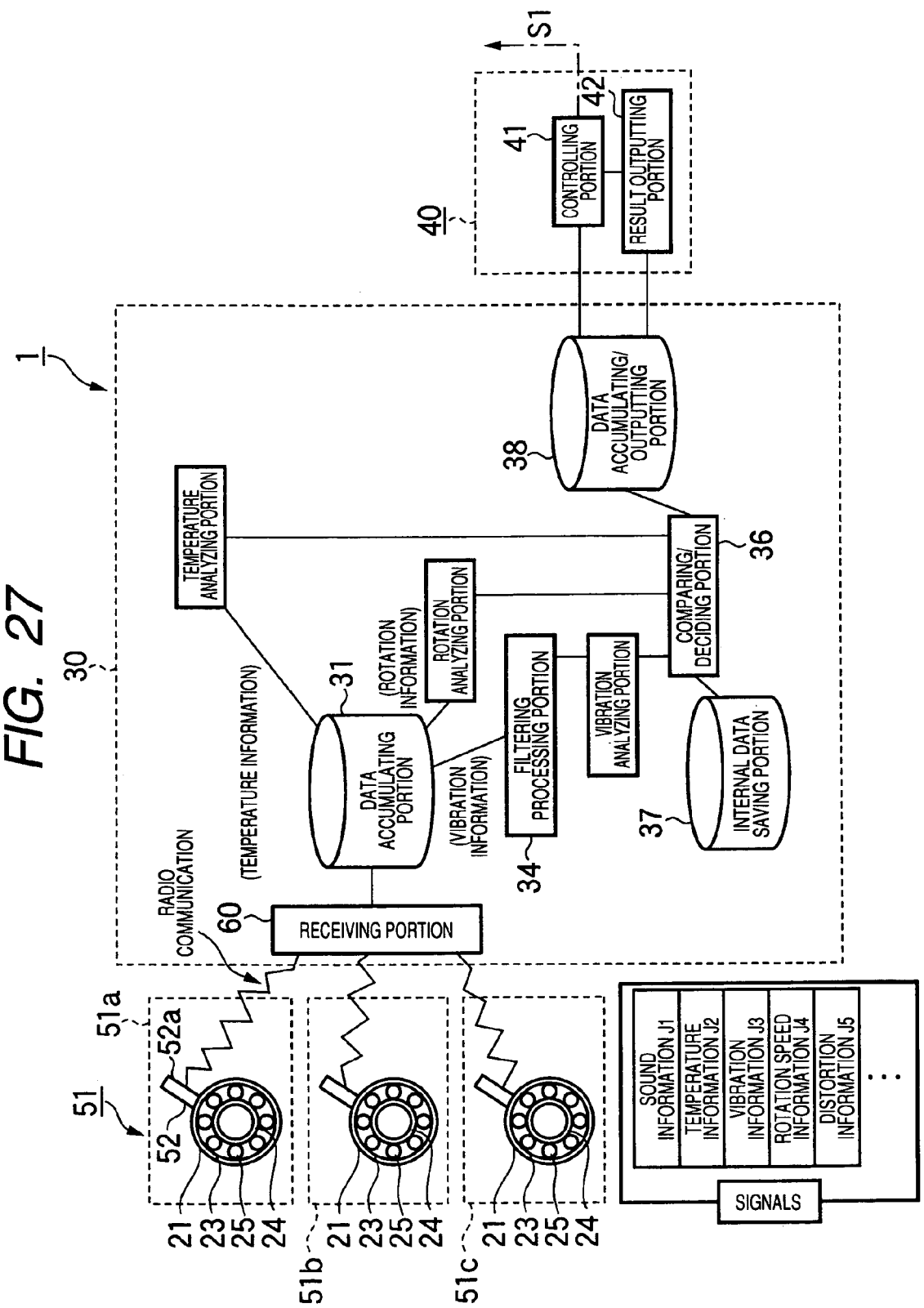
FIG. 27 is a view showing the railway vehicle abnormality diagnosis system according to the second embodiment of the present invention.

In the present embodiment, as shown in FIG. 27, a sensing/processing portion 51 consisting of sensing portions 51a, 51b, 51c each having a sensor unit 52 that communicates with the calculating/processing portion 30 via radio is provided in place of the sensing/processing portion 20. The sensing portions 51a, 51b, 5ic are constructed by fitting the sensor unit 52 onto the outer ring 23 of the bearing 21 respectively. In the sensor unit 52, a temperature sensing element 52b, a rotation sensing element 52c, a vibration sensing element 52d, and a transmitting portion 52h for radio communication are fitted into an interior of a sensor case 52a. An amplifier for amplifying the signals sensed by the sensing elements 52b to 52d by a predetermined amplification factor may be provided to the sensing element respectively. The transmitting portion 52h transmits the signals to a receiving portion 60 provided in the calculating/processing portion 30 via radio.

With the above arrangement, the sensor unit can be fitted to the bearing unit without regard to the wiring between the sensing/processing portion 51 and the calculating/processing portion 30, and the like. Therefore, a margin for arrangement of the sensors is increased and thus it can be facilitated to fit the sensor unit to the position that enhances a sensing precision. The calculating/processing portion 30 and the controlling/processing portion 40 may be connected via radio communication by providing the similar transmitter portion and receiver portion.

Other configurations and operations are similar to those in the first embodiment.

<Third Embodiment>

Figure 28:
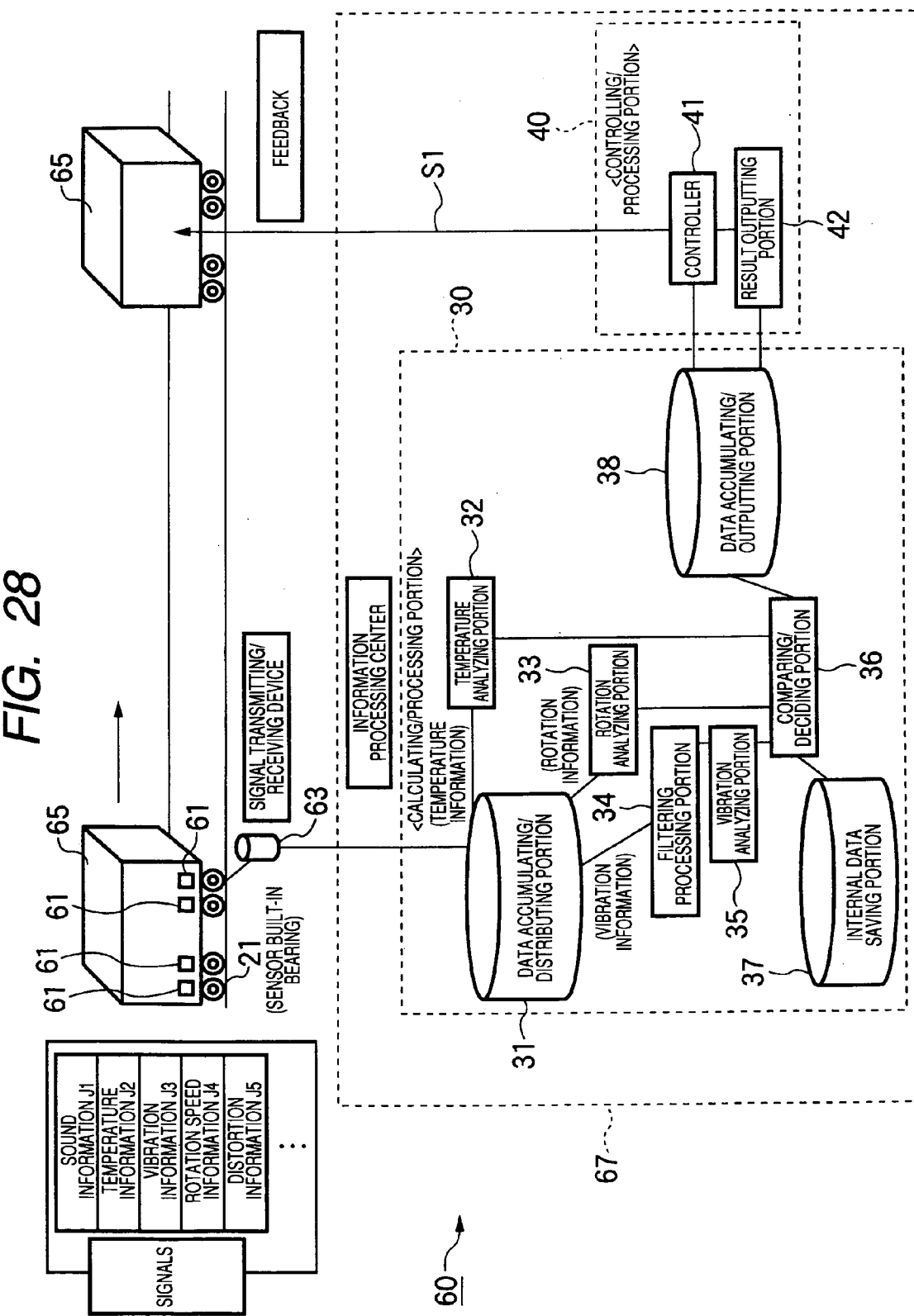
FIG. 28 is a block diagram showing a schematic configuration of a rotating body abnormality diagnosis system according to a third embodiment of the present invention.

FIG. 28 is a block diagram showing a schematic configuration of a machinery facility abnormality diagnosis system according to a third embodiment of the present invention. In a rotating body abnormality diagnosis system 60, the sensor unit installed into the sensor built-in bearing 21 that bears the axle is improved in the abnormality diagnosis system 1 in the first embodiment, and also a installing mode of the calculating/processing portion 30 and the controlling/processing portion 40, which execute predetermined processes based on the output signal of the sensor unit, are devised.

The particular configurations of the processing methods of the calculating/processing portion 30 and the controlling/processing portion 40 are similar to those in the first embodiment. Therefore, the same reference numbers are affixed to the common configurations, and thus explanation of the calculating/processing portion 30 and the controlling/processing portion 40 will be omitted herein.

A sensor unit 61 in the present embodiment is similar to the first embodiment in that, as shown in FIG. 28, the sound J3, the temperature J2, the vibration J3, the rotation speed 14, the distortion J5, AE, the moving speed, the force, the ultrasonic wave, and others and that these sensed signals are amplified by the amplifier 50 (not shown) to output.

The sensor unit 61 in the present embodiment has a radio communication device that transmits the output signal fed from the amplifier 50 via radio. An output of the sensor unit 61 is sent out to a signal transmitting/receiving device 63 via radio communication.

For example, the signal transmitting/receiving device 63 is provided to sides of railway tracks, away stations, etc. at an appropriate interval within an effective range of a radio signal along the traveling route of a railway vehicle 65 on which the sensor built-in bearing 21 is mounted. The signal transmitting/receiving device 63 sends out the signal received from the sensor unit 61 to an information processing center 67 via cable or radio communication.

The information processing center 67 has the calculating/processing portion 30 and the controlling/processing portion 40. The information processing center 67 receives the output signals of the sensor units 61 via the signal transmitting/receiving device 63 and accumulates the signals in the data accumulating/distributing portion 3 1 in the calculating/processing portion 30. Then, the data accumulating/distributing portion 31 distributes the received signals to respective analyzing portions 32, 33, 35 in the calculating/processing portion 30. Predetermined processes are applied to the distributed signals in respective analyzing portions 32, 33, 35.

The identification information (ID information) used to identify the sensor unit that outputs the signal are contained in the output of the sensor unit 61. The calculating/processing portion 30 and the controlling/processing portion 40 decide from which bearing 21 the received output is sent out, based on the identification information to discriminate the data and execute the process and the accumulation every bearing. As a result, the information processing center 67 causes the calculating/processing portion 30 and the controlling/processing portion 40 to share with a plurality of railway vehicles 65, and thus performs the central management of the abnormality diagnosis of a plurality of bearings 21.

Also, a radio communication device (not shown) for feeding back a control signal S1 to a control system of the railway vehicle 65 via radio communication is added to the controlling/processing portion 40 provided in the information processing center 67.

In the above abnormality diagnosis system 60, a margin for arrangement of the calculating/processing portion 30 and the controlling/processing portion 40 can be enhanced rather than the case where the output of the sensor unit 61 is transmitted to the calculating/processing portion via the signal line provided on the railway vehicle having the bearings, and thus the install of the rotating body abnormality diagnosis system 60 can be facilitated.

Also, since the identification information (ID information) are contained in the signal output from the sensor unit 61, the calculating/processing portion 30 and the controlling/processing portion 40 in the information processing center 67 can be shared with a plurality of railway vehicles 65. Thus, the central management of the abnormality diagnosis of a large number of bearings 21 can be carried out and thus improvement in an efficiency of the abnormality diagnosing process of the bearing 21 and reduction in a cost of the abnormality diagnosing equipment can be attained.

Other configurations and operations are similar to those in the first embodiment.

<Fourth Embodiment>

Figure 29:
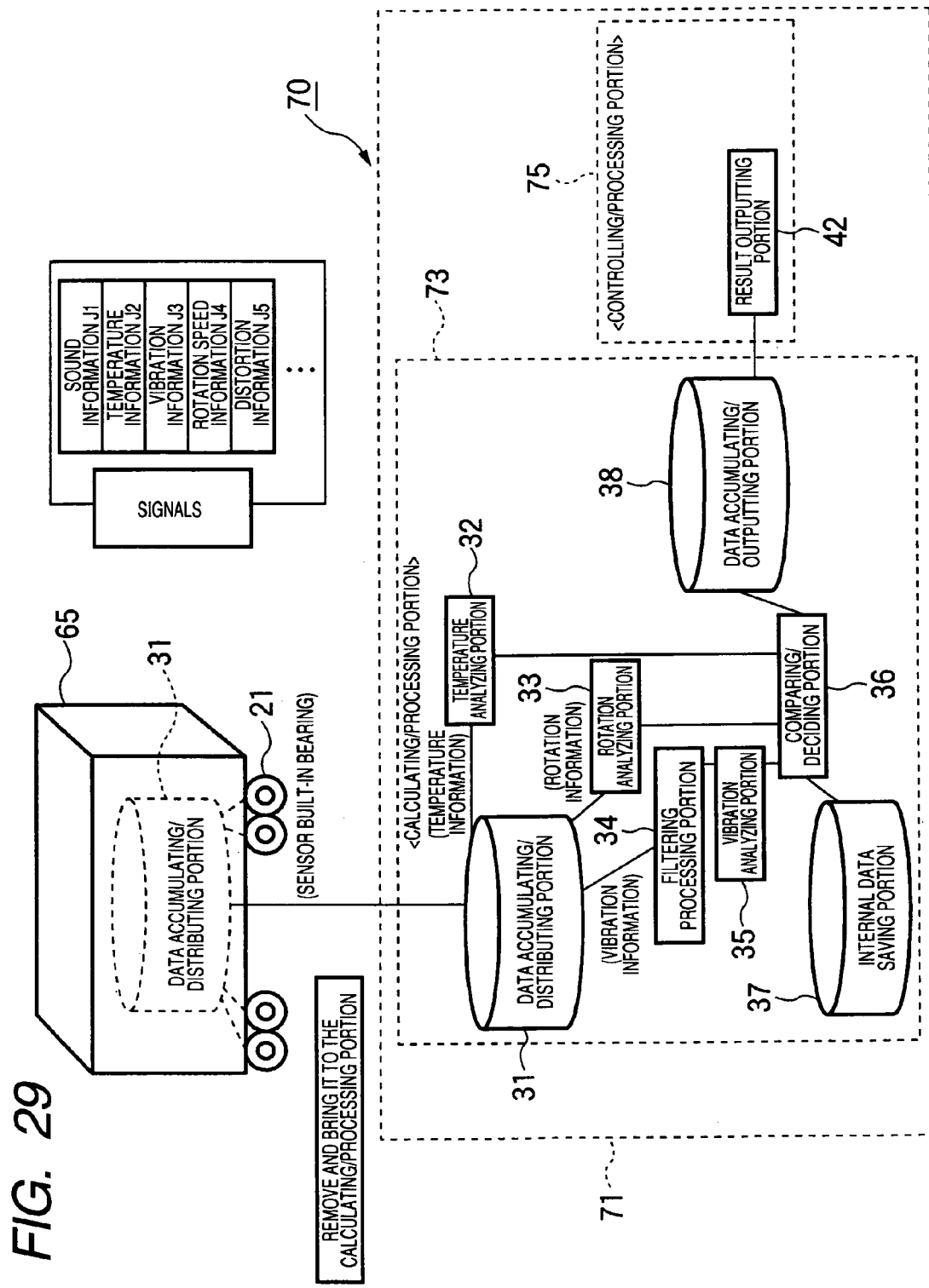
FIG. 29 is a block diagram showing a schematic configuration of a rotating body abnormality diagnosis system according to a fourth embodiment of the present invention.

FIG. 29 shows a schematic configuration of a machinery facility abnormality diagnosis system according to a fourth embodiment of the present invention. In this case, the same reference symbols are affixed to the portions similar to those in the first embodiment, and thus their redundant explanations will be omitted or simplified hereunder.

In a machinery facility abnormality diagnosis system 70 in the fourth embodiment, the sensor built-in bearing 21 shown in the first embodiment is used as the bearing that bears the axle of the railway vehicle 65, and then the data sensed by the sensor unit 22 incorporated into the bearing 21 are analyzed/decided by a calculating/processing portion 73 and a controlling/processing portion 75 provided in an information processing center 71 that is provided away from the railway vehicle 65.

In the calculating/processing portion 73, constituent means for analyzing/deciding the signals output from the sensor unit 22 are common to the first embodiment, but the data accumulating/distributing portion 31 for accumulating temporarily the output data from the sensor unit 22 and also distributing the data to the analyzing portions 32, 33, 35 in response to the data type can be detachably attached easily.

Also, the railway vehicle 65 is equipped with an accumulating portion connector (not shown). The data accumulating/distributing portion 31 attached to this accumulating portion connector can accumulate the signals output by the sensor units 22 in the bearings 21 therein.

In this abnormality diagnosis system 70, the data accumulating/distributing portion 31 that accumulates the outputs of the sensor units 22 therein is removed from the railway vehicle 65 and then is carried into the information processing center 71 and connected to the calculating/processing portion 73 in the information processing center 71. Then, various data stored in the data accumulating/distributing portion 31 are analyzed/decided by the calculating/processing portion 73, and then the result outputting portion 42 in the controlling/processing portion 75 informs the caretaker, or the like of the decision result and the analyzed result in the calculating/processing portion 73.

After the analysis/decision of the accumulated data are completed, the data accumulating/distributing portion 31 is subjected to the maintenance such as erase of the used data, or the like, as the case may be, and then is returned to the railway vehicle 65 to use again.

The abnormality diagnosis system 70 having the above configuration is unsuited to the real-time analysis/decision But this system is suited to the case where the data accumulated in the data accumulating/distributing portion 31 are kept safe for a long term or are analyzed in detail.

Also, like the case of the third embodiment, the calculating/processing portion 73 and the controlling/processing portion 75 provided in the information processing center 71 can be shared with a number of vehicles. Therefore, the abnormality diagnosis system 70 is suited to reduction in the cost of equipment required to execute the abnormality diagnosis.

Other configurations and operations are similar to those in the first embodiment.

<Fifth Embodiment>

Figure 30:
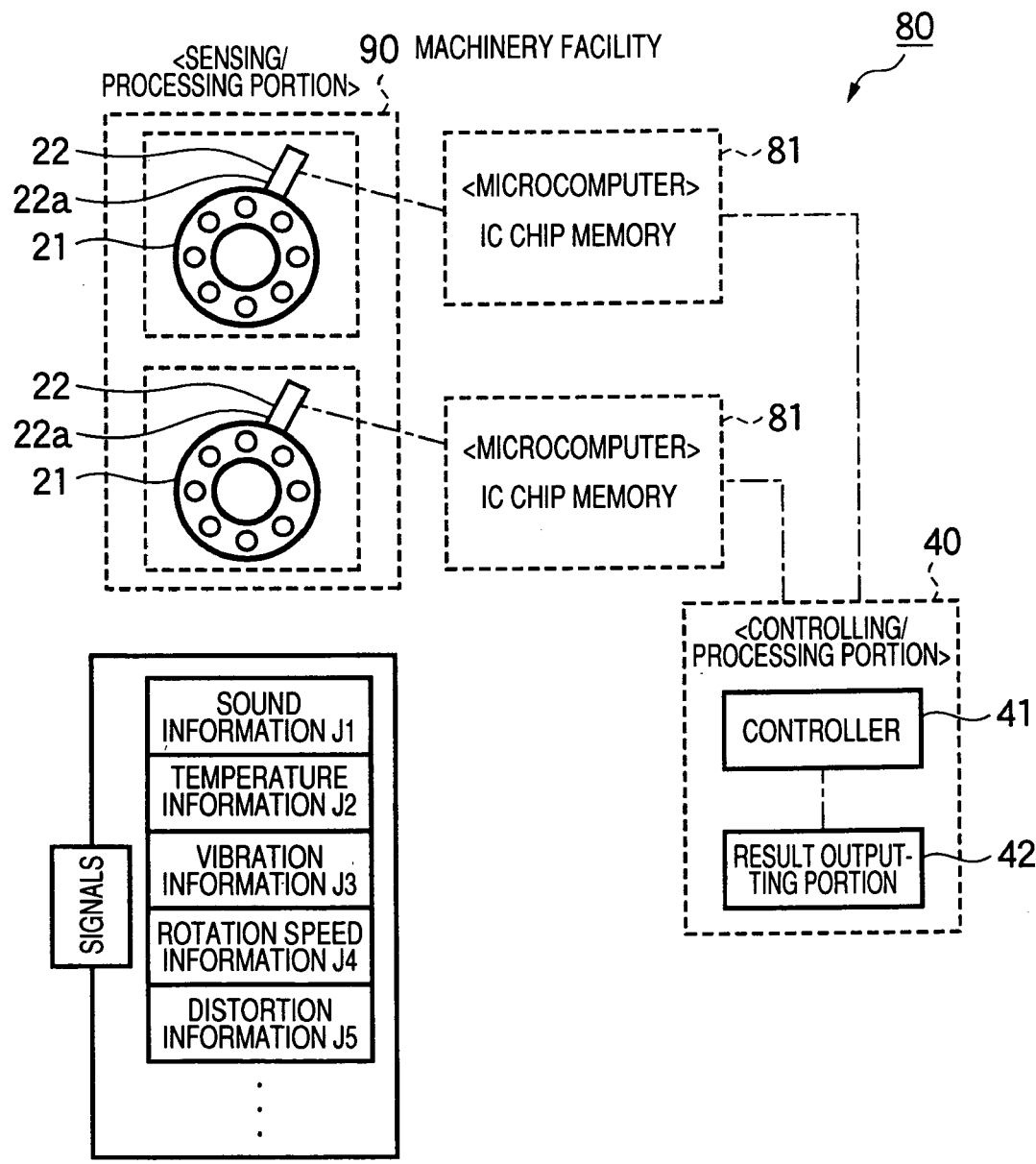
FIG. 30 is a block diagram showing a schematic configuration of a machinery facility abnormality diagnosis system according to a fifth embodiment of the present invention.

FIG. 30 shows a machinery facility abnormality diagnosis system according to a fifth embodiment of the present invention. In this event, the same reference symbols are affixed to the portions similar to those in the first embodiment, and thus their redundant explanations will be omitted or simplified hereunder.

A machinery facility abnormality diagnosis system 80 in the fifth embodiment detects generation of the abnormality generated due to the wear or the failure of constituent parts of the rolling bearing 21 from the rolling bearing 21 that bears the axle of the railway vehicle. In other words, the rolling bearing 21 that bears the axle corresponds to at least one of the rotating body and the sliding member as the diagnosed object from which the presence or absence of the abnormality is sensed, and the carriage or the railway vehicle whose axle is supported by the rolling bearings 21 corresponds to a machinery facility 90 that contains one or plural rotating bodies or sliding members.

In the case of the present embodiment, the bearing 21 is the sensor built-in bearing in which the sensor unit 22 for sensing various physical quantities such as sound, vibration, or the like generated in the rotating operation of the bearing and outputting them as the electric signal is fitted into the outer ring as the constituent parts of the bearing. A plurality of the sensor built-in bearings 21 are used in one vehicle.

The machinery facility abnormality diagnosis system 80 in the present embodiment includes a plurality of sensor units 22 provided every bearing 21, a microcomputer 81 as the calculating/processing portion that decides the presence or absence of the abnormality in the bearing 21 by analyzing the outputs of the sensor units 22 based on predetermined calculating processes and then comparing the analyzed result with reference data prepared in advance, and the controlling/processing portion 40 for displaying the analyzed result and the decision result of the microcomputer 81 in a predetermined display mode and feeding back the control signal to the control system of the railway vehicle in response to the decision result.

The physical quantity in the sliding operation (rotating operation) of the bearing 21 as the sliding member is the physical quantity that is changed in response to the rotating condition of the bearing 21. For example, various information such as sound and vibration generated by the bearing 21, rotation speed and temperature, distortion generated on the constituent parts of the sliding member, and the like may be considered.

Like the first embodiment, the sensor unit 22 includes one or plural sensing elements that sense a lot of information such as sound J1, temperature J2, vibration (vibration displacement, vibration speed, vibration acceleration) J3, rotation speed J4 of the bearing, distortion 15 generated on the outer ring of the bearing, AE, moving speed, force, ultrasonic wave, etc. as the physical quantity that is changed in response to the rotating condition of the bearing 21. Then, the sensor unit 22 sends out these sensed information to the microcomputer (calculating/processing portion) 81 as the sensed signals.

The sensor unit 22 has such a configuration that various sensors are installed/held every sensed information in the sensor case 22a secured to the outer ring of the bearing. Also, an output amplifying means for amplifying the output signals of respective sensors to output is built in the sensor case 22a.

The reference data that are compared with the analyzed result are various physical quantities that are sensed in the normal condition of the bearing 21 as the diagnosed object by the sensor unit. More particularly, there are information such as frequency components generated by the wear and the failure of the particular location of the bearing 21, and the like, in addition to sound information of the normal bearing 21, temperature information of the bearing, vibration information, rotation speed information of the bearing, distortion information generated on the outer ring of the bearing, and others.

Figure 31:
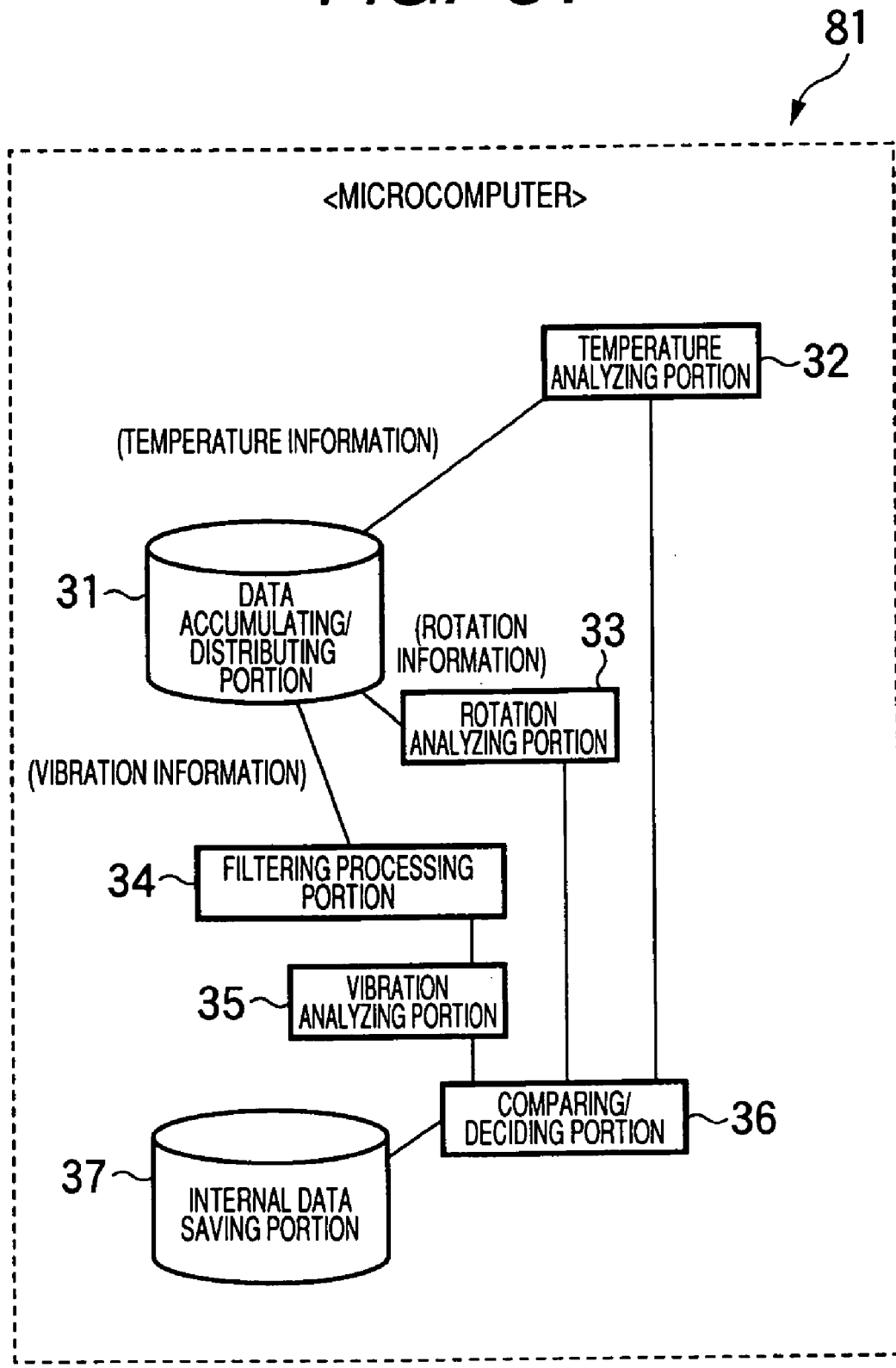
FIG. 31 is a block diagram showing a schematic configuration of a microcomputer shown in FIG. 30.

The microcomputer 81 is a one-chip microcomputer or a one-board microcomputer that is developed for the system in the present embodiment. The similar processes to those executed in the inside of the calculating/processing portion 30 are executed in the inside of the microcomputer 81. More specifically, as shown in FIG. 31, the microcomputer 81 has the data accumulating/distributing portion 31, the temperature analyzing portion 32, the rotation analyzing portion 33, the filtering processing portion 34, the vibration analyzing portion 35, the comparing/deciding portion 36, and the internal data saving portion 37, and executes the calculating process of the electric signals as the output received from the sensor to identify the presence or absence of the abnormality of the bearing and the abnormality occurring location, as explained in the first embodiment. Then, the microcomputer 81 outputs the abnormality diagnosis result to the controlling/processing portion 40, In the present embodiment, the analyzed result in the analyzing portions 32, 33, 35 and the decision result in the comparing/deciding portion 36 are output directly to the controlling/processing portion 40. But the data accumulating/outputting portion may be provided, like the first embodiment.

The controlling/processing portion 40 has the result outputting portion 42 as the displaying means for the analyzed result and the decision result in the microcomputer 81 in a predetermined display mode, and the controlling portion 41 for feeding back the control signal S1 to the control system, which controls an operation of a driving mechanism of the vehicle into which the bearings 21 are incorporated, in response to the decision result of the comparing/deciding portion 36. The operations/effects of the controlling/processing portion are similar to those explained in the first embodiment.

In the machinery facility abnormality diagnosis system 80 in the present embodiment explained as above, the presence or absence of the abnormality due to the wear and the failure of the constituent parts of the rolling bearing 21 can be decided by analyzing the output of the sensor unit 22, which is incorporated previously into the rolling bearing 21 as the sliding member, by virtue of the microcomputer 81 as the information processing device and then comparing the analyzed result with the reference data prepared previously. Therefore, the abnormality can be decided still in the normal condition of use without overhaul of the rolling bearing 21 itself and the railway vehicle itself.

As a result, a frequency of the troublesome overhauling/assembling operations can be reduced and thus the maintenance/administrative costs can be reduced. Also, since the decision is made mechanically based on the analysis and the comparison executed by specified calculating processes, the decision is hardly varied owing to a degree of expertise or individual differences of the person in charge of inspection rather than the visual inspection in the prior art, and thus the reliability of the diagnosis to check the presence or absence of the abnormality can be improved.

Also, the information processing portion is constructed by using the microcomputer 81, and the microcomputer 81 itself can be prepared as a one-chip or one-board small dedicated unit. Therefore, the overall system can be downsized considerably in comparison with the monitoring system that uses the general-purpose personal computer as the information processing device, and thus an occupied space required for the equipment can be reduced. As a result, the installation of the information processing portion into the machinery facility containing the sliding member (i.e., railway vehicle, or the like) can be facilitated.

Also, the sensor unit 22 is incorporated directly into the outer ring as the constituent parts constituting the rolling bearing 21, or the like, and thus the sensor unit 22 can sense the physical quantity generated by the rolling bearing 21 with high sensitivity. Therefore, such a possibility can be reduced that the peaks of the frequency components of the sound or the vibration generated by other articles surrounding the rolling bearing 21 exert the harmful influence upon the SN ratio of the signal sensed by the sensor, and thus improvement of the analysis/decision precisions can be attained by improving the SN ratio of the output signal of the sensor.

In addition, since the information processing portion can be formed in a compact size and also there is no need to use the large general-purpose casing, or the like, an earthquake-proof property as the information processing device can be improved easily. As a result, the information processing portion as well as the sensor unit 22 can be arranged in close vicinity to the rolling bearing 21, and thus the reliability of the abnormality diagnosis can be improved because the rolling bearing 21 and the microcomputer 81 are arranged closely to avoid the influence of the external noise.

Also, in the present embodiment, an output amplifying means (amplifier) for amplifying the output signal to output is built in the sensor unit itself. In this event, the output amplifying means for amplifying the sensor output may be connected between the sensor unit 22 and the microcomputer 81, or may be built in the microcomputer 81 side.

<Sixth Embodiment>

Figure 32:
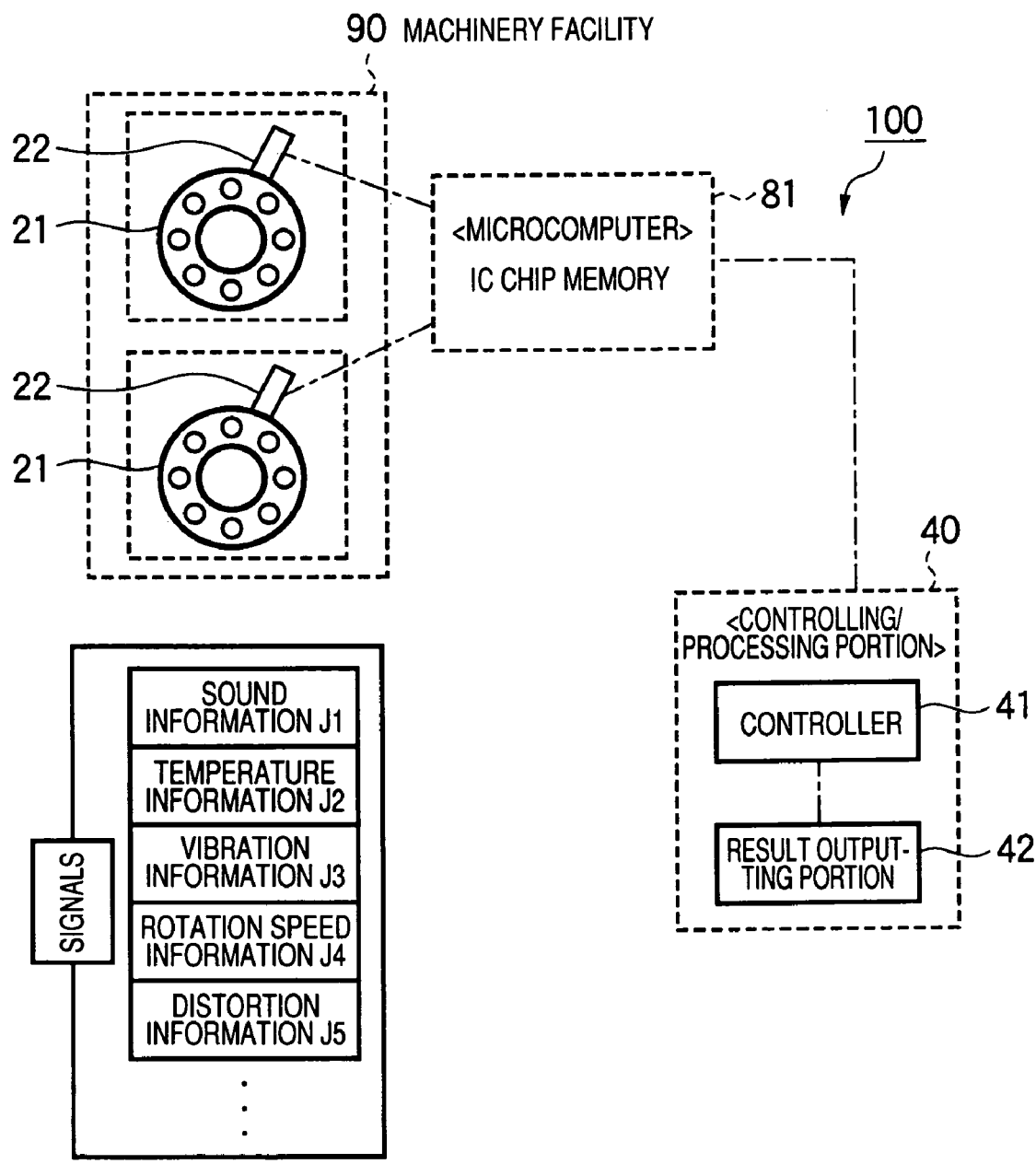
FIG. 32 is a block diagram showing a schematic configuration of a machinery facility abnormality diagnosis system according to a sixth embodiment of the present invention.

FIG. 32 is a block diagram showing a schematic configuration of a machinery facility abnormality diagnosis system according to a sixth embodiment of the present invention.

A machinery facility abnormality diagnosis system 100 in the present embodiment is constructed such that a single microcomputer 81 processes the information of a plurality of sensor units 22. Since remaining configurations are similar to those in the fifth embodiment, the same reference numbers as those in the fifth embodiment are affixed to the common configurations, and thus explanation of the microcomputer 81 and the controlling/processing portion 40 will be omitted herein.

In case the microcomputer 81 has an enough processing performance in reserve, the single microcomputer 81 is caused to process the information of a plurality of sensor units 22 in this manner. Therefore, the number of equipments of the expensive microcomputer 81 can be reduced and a cost reduction can be attained.

In the above embodiments, install positions of the microcomputer 81 are not particularly mentioned. It is preferable that the microcomputer 81 as well as the sensor unit 22 should be fitted to the rotating body or the sliding member or the mechanism parts for supporting the sliding member. By doing this, such a system instating mode can be realized that both the sensor unit 22 and the microcomputer 81 are arranged in close vicinity to each other on the same constituent member. Therefore, a length of the signal line between the sensor unit 22 and the microcomputer 81 is not extended, and thus generation of the disadvantages caused by interwining of the signal line, and the like can be prevented.

Also, the influence of the external noise upon the signal transmission line between the sensor unit 22 and the microcomputer 81 can be reduced, and thus the reliability of the sensed signal can be improved.

<Seventh Embodiment>

Figure 33:
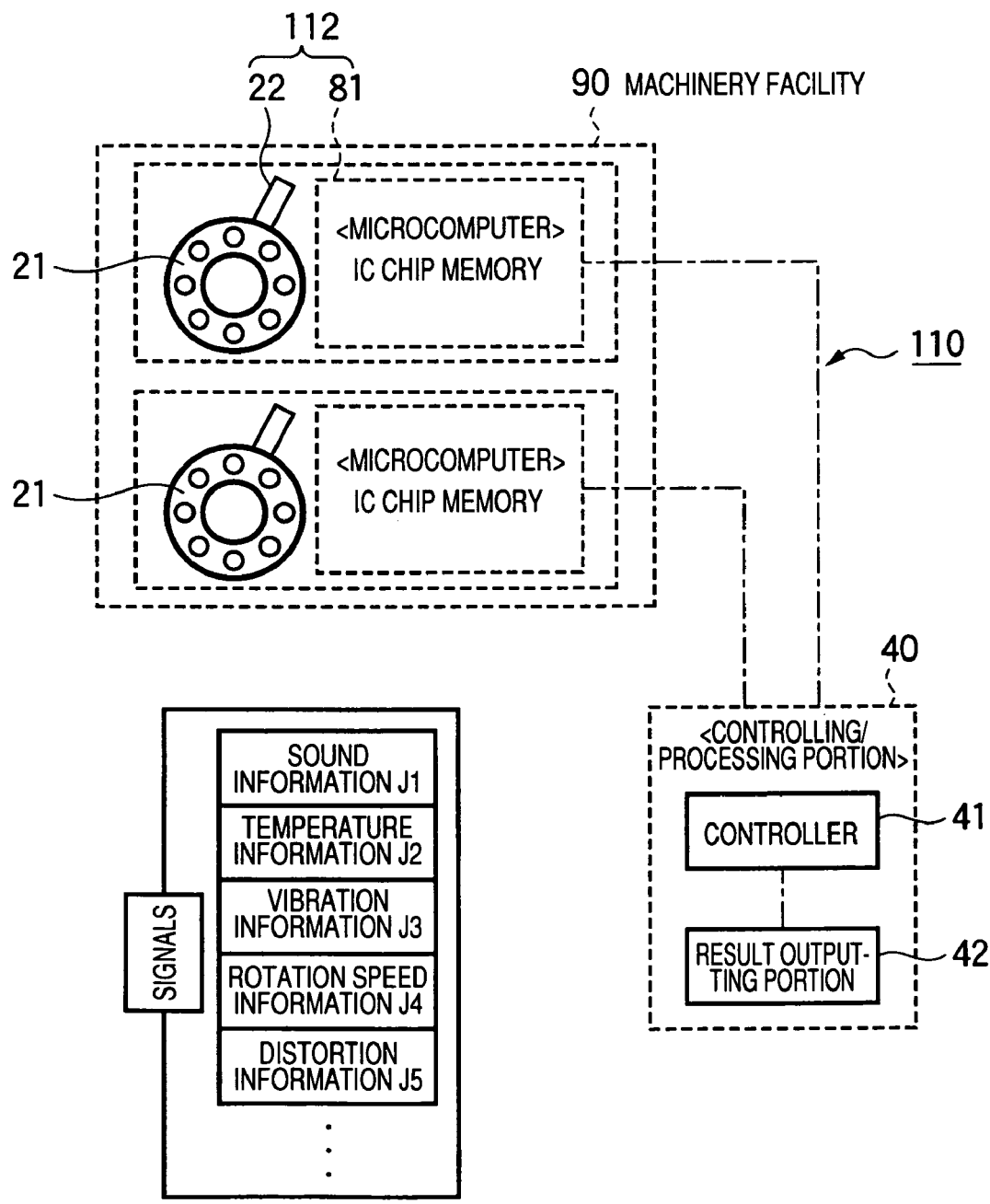
FIG. 33 is a block diagram showing a schematic configuration of a machinery facility abnormality diagnosis system according to a seventh embodiment of the present invention.

FIG. 33 shows a machinery facility abnormality diagnosis system according to a seventh embodiment of the present invention.

In a machinery facility abnormality diagnosis system 110 in the seventh embodiment, the microcomputer 81 and the sensor unit 22 are mounted on a single device substrate and then fitted to the constituent parts of the rolling bearing 21 as a single processing unit 112. Since the rolling bearing 21 and the controlling/processing portion 40 to which the microcomputer 81 outputs the decision result may have the same configuration as those in the above embodiments, their explanation will be omitted herein. According to the abnormality diagnosis system 110 constructed in this manner, the fitting of the monitoring system to the machinery facility 90 can be completed by fitting the single processing unit 112 thereto, and thus a fitting workability can be improved.

In the machinery facility abnormality diagnosis system according to the present invention, the sensor unit 22 and the microcomputer 81 are not connected via the signal cable, or the like, and the signal may be transmitted/received via radio communication. When doing this, a margin for arrangement of the microcomputer 81 and the controlling/processing portion can be enhanced rather than the case where the output of the sensor unit 22 is transmitted to the microcomputer 81 via the signal cable that is provided on the equipment containing the sliding member, and thus the installation of the machinery facility abnormality diagnosis system can be further facilitated.

<Eighth Embodiment>

FIG. 34(*a*) and FIG. 34(*b*) show a machinery facility abnormality diagnosis system according to an eighth embodiment of the present invention.

In a machinery facility abnormality diagnosis system 151 of the eighth embodiment, a diagnosis unit 161 constructed by mounting a microcomputer containing a CPU 152 to execute the calculating process, an amplifier circuit (Amp) 153, A/D converters (ADCs) 154, 155, external memories (RAM, ROM, ROM) 156, 157, 158, and the communication circuits (LANIF, SCI) 159, 160 on a board (not shown) is installed into a case (casing) 161A. Then, a piezoelectric sensor 162, a temperature sensor 163, and a rotating pulse generator 164 are fitted to the bearing 21 as the sensors.

The piezoelectric sensor 162 detects a vibration acoustic signal generated when the rolling elements (not shown) of the bearing 21 pass over the flaw on the raceway ring (not shown), an AE (acoustic emission) signal generated when the minute crack is developing, or the like, and converts such signal into a voltage or charge signal. The voltage or charge signal is amplified at about 20 to 40 dB by a pre-amplifier (preamplifier circuit) 165 arranged in close vicinity to the piezoelectric sensor 162. Then, the signal after entered into the case 161A is converted into a voltage signal, a level of which corresponds to an input range of the A/D converter 154, by the amplifier circuit 153. The voltage signal converted by the amplifier circuit 153 is input into the A/D converter 154 via a bandpass filter (BPF) 166 and then is fed to a predetermined port of the microcomputer including the CPU 152. The A/D converter 154 is an external high-precision A/D converter with a 16-bit resolution.

Because the analog bandpass filter 166 is put at the preceding stage of the A/D converter 154 to pass the frequency of 1 kHz to 10 kHz, the low-frequency mechanical vibration and the aliasing caused due to an upper limit frequency in the A/D conversion can be prevented. This filtering function can be replaced with a digital filter such as PLD, or the like that is put at the subsequent stage of the A/D converter. Such preprocess filtering may be executed in the CPU calculation, but the preprocess filtering is separated from the CPU calculation because a processing speed and a program size are influenced.

Since the A/D converted value is obtained as the signed integer, a full-wave rectified waveform can be derived by calculating an absolute value of a finite-time wave. Because the full-wave rectified waveform is finite, the FFT operation is executed after an influence of both ends is lessened by applying the Window process. Since a floating-point operational unit is not provided to the microcomputer containing the CPU 152, a fixed point operation that can be calculated by using the integer only is used.

The resultant frequency distribution is compared with the frequency of an envelope having a damping waveform decided by the rotating speed and the number of the rolling elements in order of higher intensity. At this time, bearing specifications stored in the external memories 157, 158 and the speed value derived from the rotating pulse generator 164 are employed.

The piezoelectric sensor 162 can get acoustic/elastic wave/AE signals. But its sampling frequency is set to 100 kHz for the purpose of sensing the flaking/damage mainly.

The voltage signal generated by the temperature sensor 163 is input into the A/D converter 155 via the amplifier circuit (not shown) and is given to a predetermined port of the microcomputer including the CPU 152. The A/D converter 155 is an external high-precision A/D converter with 10-bit resolution. The temperature sensor 163 and the rotating pulse generator 164 are set to a sampling frequency that is lower than that of the piezoelectric sensor 162.

The external memory 156 is formed of RAM, and the external memories 157, 158 are formed of ROM. Also, the communication circuit 159 is composed of a LAN interface, and is connected to a LAN line (Local Area Network) 167 via a twisted pair, a coaxial cable, an optical fiber cable, or the like. When a radio LAN is employed, the communication circuit 159 is connected to the LAN line 167 via radio. The communication circuit 160 gives a serial communication interface, and is connected to a program loading/diagnostic data transmitting and receiving terminal 168.

The communication circuit 160 is used to transmit/receive in serial an extent of coincidence between the sensed frequency and respective flaw frequencies of the outer ring, the inner ring, the rolling elements, and the retainer of the bearing 21. A parallel-type communication circuit may be employed if it is used within a short distance. Preferably a dedicated IC for ensuring a security should be interposed in the communication line.

The machinery facility abnormality diagnosis system 151 further includes a timer counter (TMUCNT) 169, a direct memory access controller (DMA) 170, an interruption controller (INTC) 171, a D/A converter (DAC) 172, and an active gain control (AGC) 173. The D/A converter 172 is connected to a diagnostic output connector and/or display 174.

The timer counter 169 counts up a pulse signal generated by the rotating pulse generator 164 and then gives the number of counted pulses to a predetermined port of the microcomputer including the CPU 152.

The interruption controller 171 and the timer counter 169 are used to feed the signal to the microcomputer including the CPU 152 at a predetermined sampling period. Normally the data are transferred to the external memory 156 via the microcomputer including the CPU 152. But the direct transfer may be applied by the direct memory access controller 170 to shorten extremely the sampling period.

When the operator can come close to the diagnosis unit 161 or when the diagnosis unit 161 can be put near the machine operator, the diagnostic output connector and/or display 174 is used to give the LED display or the liquid crystal screen display via the LCD driver, give the sound output using the D/A output, or the like.

In the machinery facility abnormality diagnosis system 151, all the data digitized by the signal processing are calculated by the microcomputer including the CPU 152, and various processing programs are loaded on the external memories 157, 158 attached separately. Also, since at least one machinery facility abnormality diagnosis system 151 is used in one unit of the bearing 21, the specifications (dimensions of respective portions, material, number of the rolling elements, lubricant, date of manufacture) of the bearing 21 and the specifications (frequency characteristic, sensitivity) of the sensors 162, 163, 164 are stored in the external memories 157, 158.

Also, since RMS, peak, crutosis, peak factor, etc. are assigned to predetermined addresses of the external memory 156 as amplitude parameters, the external device can inquire about the data by using the communication function.

In the machinery facility abnormality diagnosis system 151, the piezoelectric sensor 162, the temperature sensor 163, and the rotating pulse generator 164 for sensing acoustic/elastic wave, ultrasonic wave, and mechanical vibration, for example, are fitted to the bearing 21, and then the diagnosis unit 161 capable of amplifying/digitizing the signals generated by these sensors, then applying the calculating process to the signals by virtue of the microcomputer containing the CPU 152, and then outputting the calculated result is installed into the single case 161A. For this reason, the condition of the bearing 21 can be monitored with a simple configuration without overhaul and also the defect or the abnormality of the bearing 21 can be inspected. As a result, time and labor required to overhaul and assemble the bearing 21 can be reduced and the damage of the bearing 21 caused by the overhauling and the assembling can be prevented. In addition, since the monitoring can be executed effectively with good precision, the higher-precision diagnosis can be carried out and thus the defect that the visual inspection could overlook can be found. Also, the diagnosis unit 161 can be installed into various machinery equipments other than the bearing 21 because such diagnosis unit 161 can be formed in a compact size by using small-size sensors, the microcomputer, IC, and the circuit board, and the diagnosis unit 161 can be installed flexibly into various machinery equipments because such diagnosis unit 161 can have a communication capability, so that the diagnosis unit 161 can contribute to the reduction in a cost aspect and the energy saving measure. Since the ultrasonic pulse echo approach can be utilized by providing not only a function of amplifying the signals from respective sensors but also a function of sending the pulse signal to the piezoelectric sensor 162, for example, to the diagnosis unit 161, the damage of the mechanical sliding surface in the stationary time and the metal contact condition between the sliding surfaces in the running time can be sensed/diagnosed.

Also, in the machinery facility abnormality diagnosis system 151, one or more out of temperature, vibration displacement, vibration speed, vibration acceleration, force, distortion, acoustic, acoustic emission, ultrasonic wave, and rotating speed can be sensed by the piezoelectric sensor 162, the temperature sensor 163, and the rotating pulse generator 164. Therefore, the condition of the bearing 21 can be monitored without fail and also the defect or abnormality of the bearing 21 can be inspected without fail.

Also, in the machinery facility abnormality diagnosis system 151, the microcomputer containing the CPU 152, the amplifier circuit 153, the A/D converter circuits 154, 155, the external memories 156, 157, 158, the communication circuits 159, 160, the timer counter 169, the direct memory access controller 170, the interruption controller 171, the D/A converter 172, and the active gain control 173 are employed in the calculating process. Therefore, the diagnosis system that is excellent in a cost aspect can be realized by using a combination of the general-purpose parts without custom parts.

Also, in the machinery facility abnormality diagnosis system 151, one process or more out of calculation of feature parameters of a standard deviation and a peak factor, envelope detection, FFT, filter, wavelet transform, short-time FFT, and calculation of a feature frequency due to the defect of the rotating body and the comparing/deciding processes can be executed in a digital fashion. Therefore, since the monitoring can be executed effectively with good precision, the higher-precision diagnosis can be carried out and thus the defect that the visual inspection could overlook can be found surely.

<Ninth Embodiment>

Figures 35A, 35B:
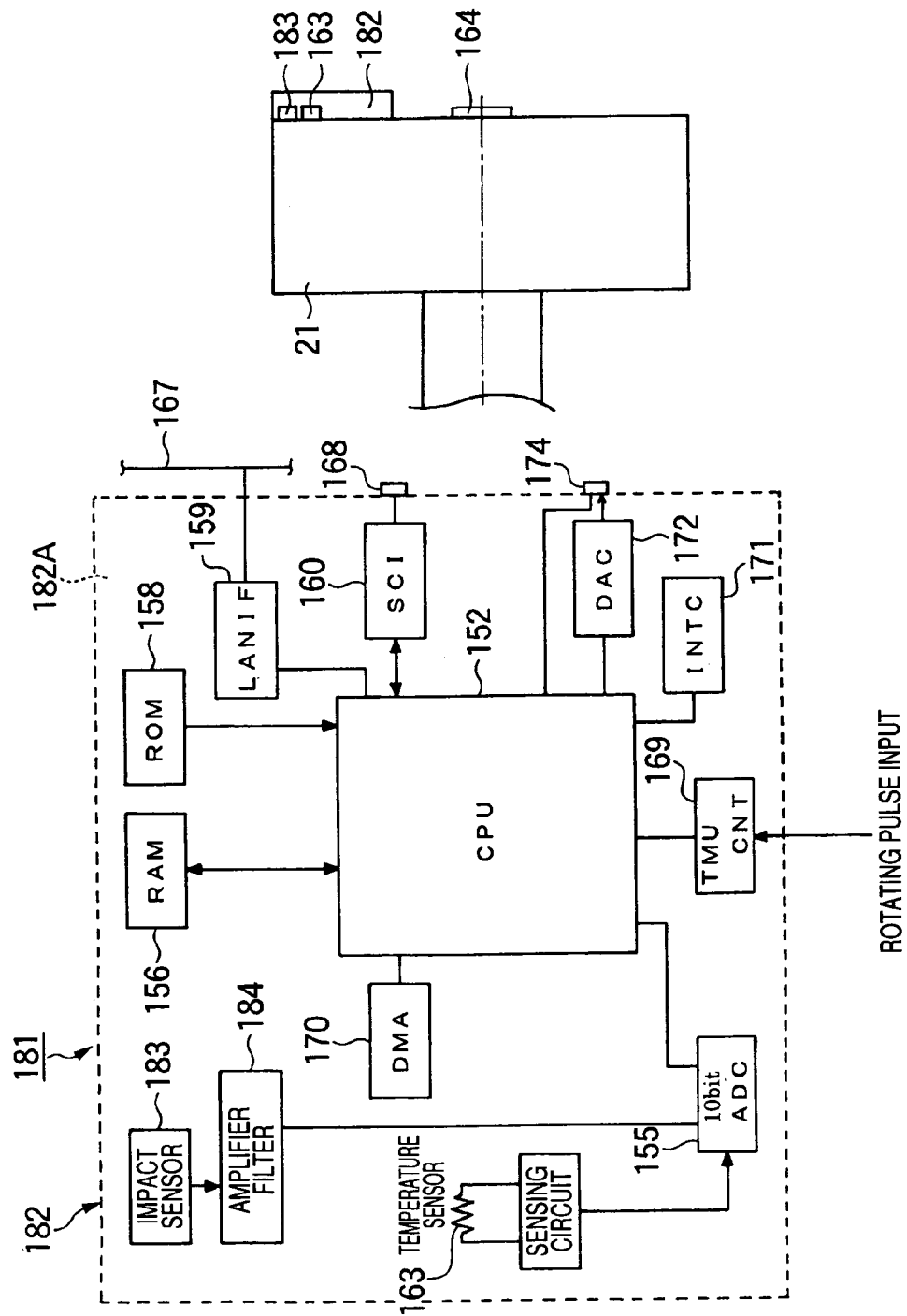
FIG. 35(a) is a block diagram showing a schematic configuration of a machinery facility abnormality diagnosis system according to a ninth embodiment of the present invention.
FIG. 35(b) is a side view showing a bearing fitting state in FIG. 35(a)

FIG. 35(*a*) and FIG. 35(*b*) show a machinery facility abnormality diagnosis system according to a ninth embodiment of the present invention.

In a machinery facility abnormality diagnosis system 181 of the ninth embodiment, an impact sensor 183 that is formed as a bimorph of a piezoelectric ceramic element is installed a case 182A of a diagnosing unit 182, and also the impact sensor 183 and the temperature sensor 163 arc arranged integrally in the case 182A. Since other configurations are similar to those in the eighth embodiment, the same reference numbers as those in the eighth embodiment are affixed to the common configurations, and thus explanation about them will be omitted herein.

In the machinery facility abnormality diagnosis system 181, an impact generated when the bearing 21 goes down is detected. Normally, the feature parameter computing expressions for the natural impulse elastic waves generated at the time of failure of the bearing 21 are stored in the external memory 158. If the feature parameter decided based on a waveform signal, which is digitized via the impact sensor 183, an amplifier filter portion 184, and the A/D converter 155 as the high-precision external A/D converter with 10-bit resolution, and the rotation speed has the dimension, mean value of the vibration value, standard deviation (rms), maximum value, peak (average of ten values counted from the maximum absolute value), etc. are calculated previously. Meanwhile, if the feature parameter is dimensionless, wave waveform, peak factor, impact index, skewness, crutosis, etc. are calculated previously. The approach of sensing the defect of the bearing 21 from the frequency domain data, which is obtained by the FFT operation by the microcomputer including the CPU 152, is similar to the seventh embodiment. In this event, the impact sensor 183 and the amplifier filter portion 184 may be integrated as far as the frequency band permits.

The data of cross frequency of the feature parameter in other frequency domain, extreme frequency, degree of irregularity, degree of contain of the rotating frequency, degree of contain of the rotating frequency harmonics, degree of contain of the defect feature frequency component powers of respective parts of the bearing 21, etc. are registered in the external memory 156, and then are updated in a predetermined period.

The degradation diagnosis of the bearing 21 by the feature parameters may be executed by the microcomputer including the CPU 152 in the case 182A. Alternately, if the diagnosis is recognized by using the regression analysis in which a large number-of parameters are related complicatedly or the learning algorithm using the neural network, the data may be processed by transmitting the data to the computer, into which the recognition program is installed, separately via the LAN line 167, or the like. Otherwise, it is preferable that the custom IC exclusively used for the recognition program or another microcomputer should be added.

In the machinery facility abnormality diagnosis system 181, the diagnosis unit 182 can be constructed by using small- size electronic parts, small-size sensors, and short wirings in addition to the microcomputer including the CPU 152. Thus, such diagnosis unit 182 can be installed into the space-saving case 182A and thus the inspection/diagnosis can be executed by such diagnosis unit 182 incorporated into the bearing 21. Also, the diagnosis unit 182 can be constructed in a compact size, and a cost can be further reduced by omitting the signal line extended from the sensors to the calculating/processing device.

<Tenth Embodiment>

Figure 36:
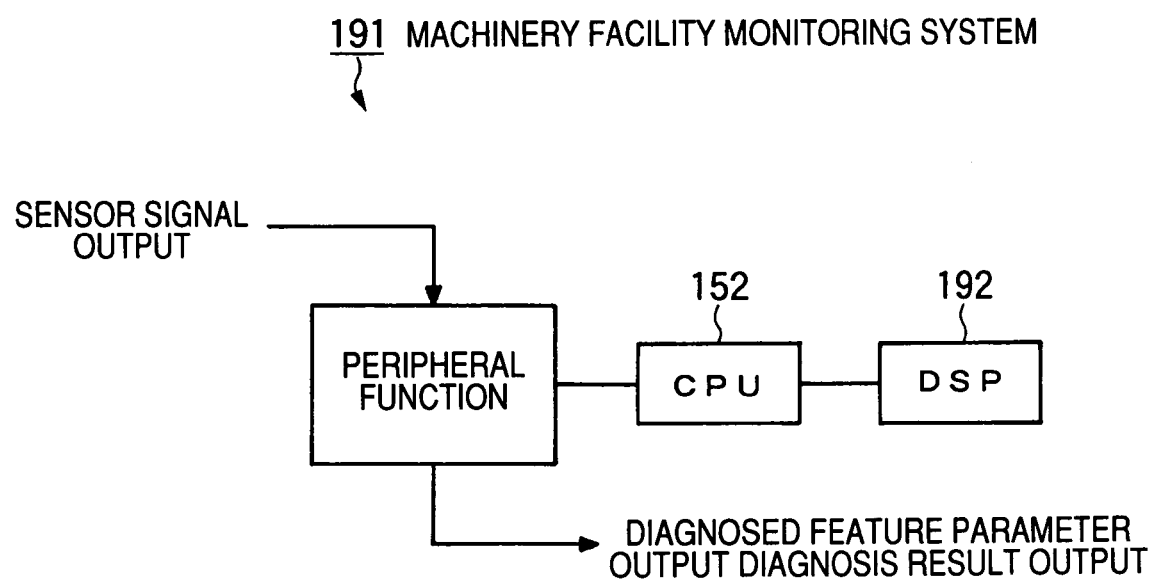
FIG. 36 is a block diagram showing a schematic configuration of a machinery facility abnormality diagnosis system according to a tenth embodiment of the present invention.

FIG. 36 shows a machinery facility abnormality diagnosis system according to a tenth embodiment of the present invention.

In a machinery facility monitoring system 191 of the tenth embodiment, a DSP (digital signal processor, capable of executing a product-sum operation in a filtering operation and a data transfer at a high speed) 192 is incorporated into the calculating/processing portion.

In this embodiment, the eighth and ninth embodiments are revised such that the DSP 192 takes charge of the digital signal processing such as digital filtering, FFT, and the like and also the microcomputer containing the CPU 152 executes other processes. Also, for the same purpose, the calculating/processing portion can be constructed by using a PLD (programmable logic device) without the DSP.

In the above embodiment, the sliding member that is diagnosed to check whether or not the abnormality is present is not limited to the rolling bearing. More particularly, the sliding bearing, and the like correspond to the sliding member in addition to various rolling bearings. Also, constituent parts of the longitudinal motion mechanism such as the ball screw, the linear guide, etc. correspond to the sliding member as the diagnosis object of the present invention. Also, various large-size rotary sliding members such as the gear or the wheel of the railway vehicle, etc., which take enormous time and labor to remove and fit, can be selected as the abnormality diagnosis object of the present invention.

In the above embodiment, the machinery facility abnormality diagnosis system itself is equipped with the controlling/processing portion that feeds back the signal responding to the decision result to a controller that controls an operation of the mechanism, into which the sliding members are incorporated, of the machinery facility such that the sensing of the abnormality by this abnormality diagnosis system leads quickly to the maintenance and the operation management of the machinery facility. However, the controlling/processing portion may be constructed as the independent equipment (system) that can be connected to the abnormality diagnosis system.

<Eleventh Embodiment>

Next, a machinery facility condition monitoring system according to an eleventh embodiment of the present invention will be explained hereunder. In this event, the same reference symbols are affixed to the portions similar to those in the fifth embodiment, and thus their redundant explanations will be omitted or simplified hereunder.

Figure 37:
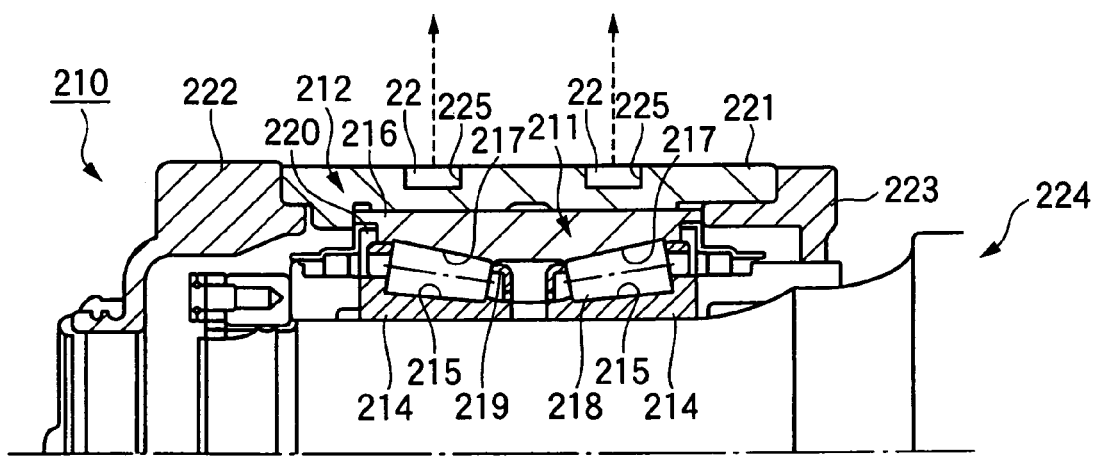
FIG. 37 is a sectional view showing a machinery facility to which a condition monitoring system according to an eleventh embodiment of the present invention is applied.
Figure 38:
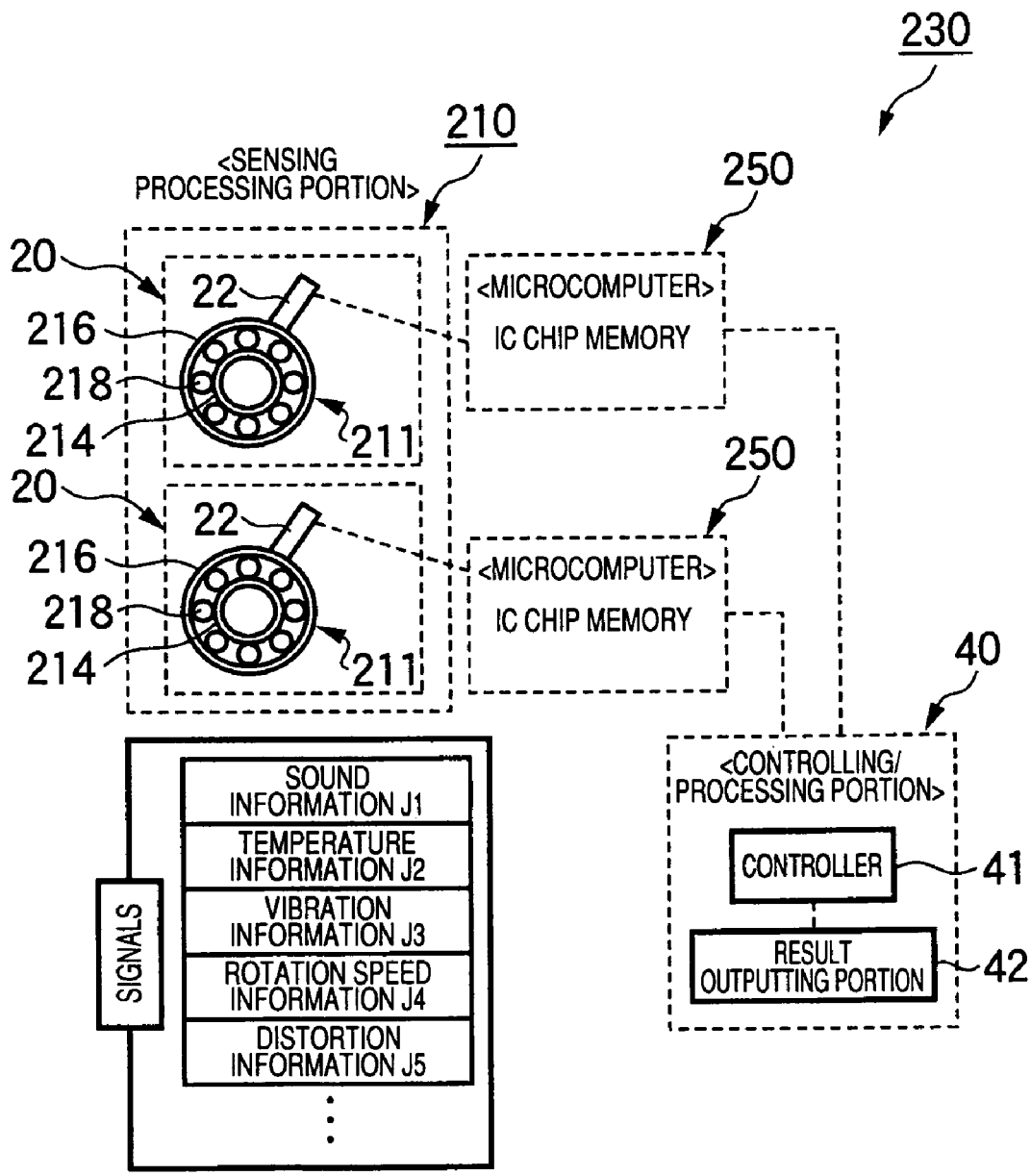
FIG. 38 is a schematic view showing the condition monitoring system according to the eleventh embodiment.

As shown in FIG. 37, a railway vehicle facility 210 as a machinery facility, to which a condition monitoring system 230 (see FIG. 38) is applied, includes a double row tapered roller bearing 211 as at least one of the rotating body and the sliding member as the sensed object and a bearing housing 212 constituting a part of the railway vehicle carriage.

The double row tapered roller bearing 211 has a pair of inner rings 214, 214 having inner ring raceway surfaces 215, 215 inclined like a tapered outer surface on their outer peripheral surfaces, a single outer ring 216 having a pair of outer ring raceway surfaces 217, 217 inclined like a tapered inner surface on an inner peripheral surface, tapered rollers 218 as a plurality of rolling elements arranged in double rows between the inner ring raceway surfaces 215, 215 of the inner rings 214, 214 and the outer ring raceway surfaces 217, 217 of the outer ring 216, annular pressed retainers 219, 219 for holding rollably the tapered rollers 218, and a pair of sealing members 220, 220.

The bearing housing 212 has a housing 221, a front lid 222 fitted to a front end portion of the housing 221, and a rear lid 223 fitted to a rear end portion of the housing 221.

An axle 224 is press-fitted into the inner ring of the double row tapered roller bearing 211. A radial load imposed by weights of various members, etc. and any axial load are applied to the double row tapered roller bearing 211. An upper area of the outer ring 216 serves as a loading range. Where the loading range denotes an area in which the load is applied to the rolling element.

The housing 221 constitutes a side frame of the railway vehicle carriage, and is formed like a circular ring to cover the outer peripheral surface of the outer ring 216. A pair of recess portions 225, 225 are formed on the outer peripheral surface of the housing 221 in the center portion of each row of the double row tapered roller bearing 211 in the axial direction. The recess portions 225, 225 receive therein the sensor units 22, 22 constituting a part of the condition monitoring system 230 and having the same configuration as the first embodiment.

Next, the condition monitoring system 230 of the eleventh embodiment will be explained hereunder. The condition monitoring system 230 is different from the fifth embodiment only in the process that is executed by a comparing/deciding portion 252 in a calculating/processing portion 250 constructed by the microcomputer, but the processes in the sensing/processing portion 20 and the controlling/processing portion 40 are equivalent to the abnormality diagnosis system in the fifth embodiment. In other words, the condition monitoring system 230 includes the sensing/processing portions 20, 20 having the sensor units 22, 22 provided to the rows of the double row tapered roller bearing 211 respectively to output the condition of respective rows as the electric signal, the calculating/processing portions 250, 250 for calculating/processing the electric signals output from the sensor units 22, 22 to decide the conditions such as the defect, the abnormality, or the like of the railway vehicle facility 210, and the controlling/processing portion 40 for controlling/outputting the decision result of the calculating/processing portions 250, 250.

The sensor units 22, 22 has sensors as a plurality of sensing elements that can sense the information such as sound J1, temperature J2, vibration J3, rotation speed 14, distortion J5, AE (acoustic emission), moving speed, force, ultrasonic wave, etc., which are generated from the machinery facility during the running, as the physical quantity that changes in response to the rotating state of the bearing 211 and then output the information to the calculating/processing portions 250, 250 as the electric signal. Here, since the calculating/processing portions 250, 250 can appropriately distribute/process the electric signals every sensed information, a plurality of sensing elements for sensing independently the particular signal such as sound, temperature, vibration, rotation speed, distortion, AE, moving speed, force, ultrasonic wave, or the like respectively may be employed in combination as the sensor units 22, 22, otherwise a composite sensor unit capable of sensing a plurality of information at the same time may be employed as the sensor unit 22.

Also, the fitting position of the sensor unit 22 is selected on the outer peripheral portion of the housing 221 in the loading range of the radial load. Therefore, when the damage is caused on the bearing raceway surface, for example, a collision force generated when the rolling element passes over the damaged portion is larger in the loading range than the non-loading range. Thus, the abnormal vibration can be sensed in the loading range of the bearing with good sensitivity.

In addition, the sensor unit 22 is fitted into the recess portion 225 formed in the housing 221. Therefore, since the sensor unit 22 is never affected by the fitting state of the sensor unit 22 and the surrounding environment (noise, moisture, wind pressure, etc.), the signal can be sensed at a high SN ratio (noise-to-signal ratio) with high precision. Here, the sensor unit 22 may be incorporated into the rotating body, the sliding member, or the like.

Also, it is preferable that the function or the process of waterproof, oil-resistant, dustproof, rust-preventive, moisture-proof, heat-resistant, and electromagnetic noise-resistant properties should be added or applied to the sensor unit 22 to lessen the influence of the noise. In addition, it is more preferable that an amplifier function should be built in the sensing/processing portions 20, 20 and thus there is no need to provide the special amplifier and the anxiety in regard to the entering of the noise from the intermediate cable, or the like can be removed, The calculating/processing portions 250, 250 execute the calculating/processing operations to decide the condition such as the defect, the abnormality, or the like of the machinery facility based on the electric signals output from the sensing/processing portions 20, 20. Such operations are executed by the microcomputer. The microcomputer consists of an IC chip on which CPU, MPU, DSP, etc. are mounted, a memory, and the like.

Figure 39:
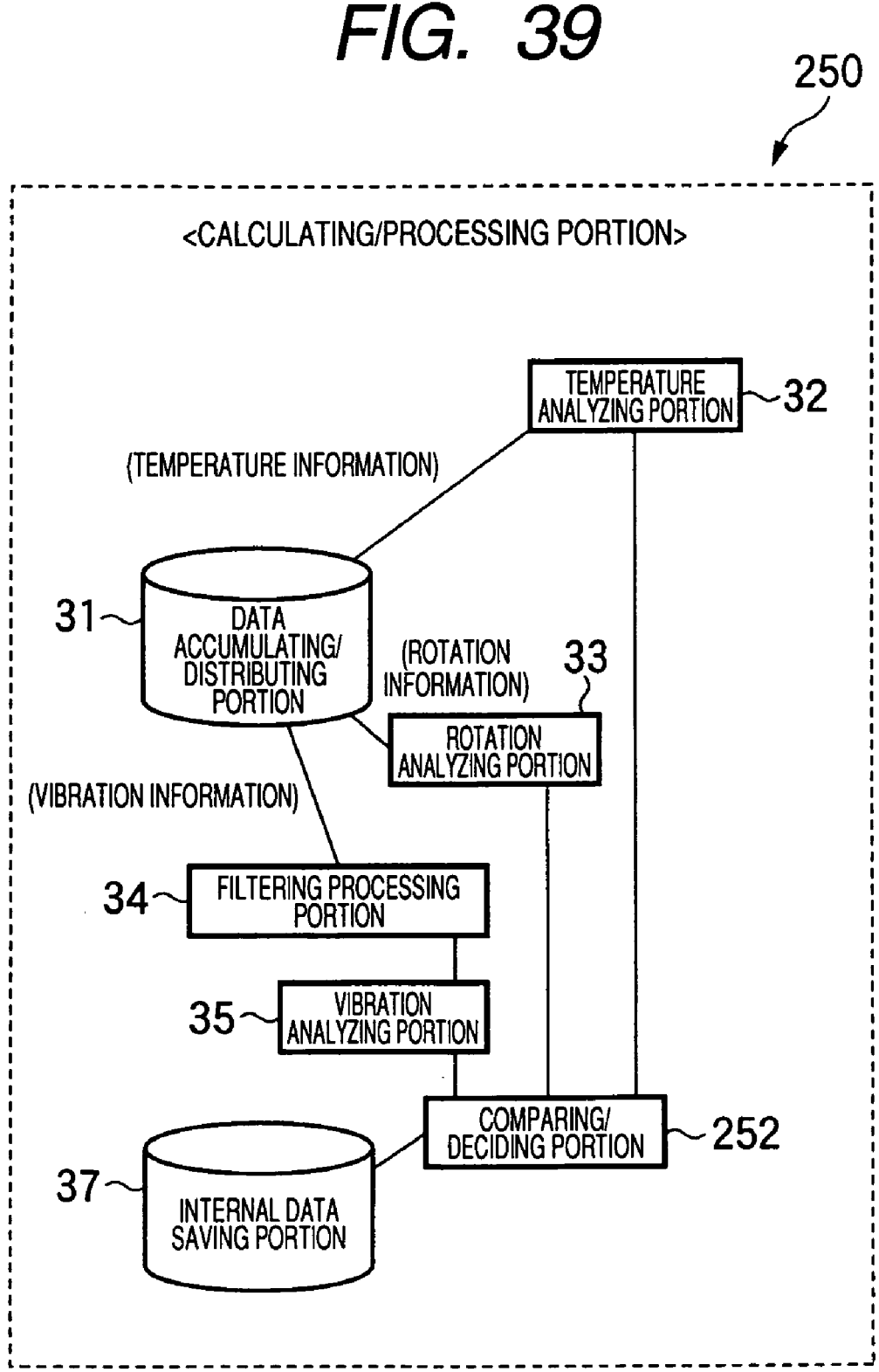
FIG. 39 is a block diagram of a calculating/processing portion in FIG. 38.

As shown in FIG. 39, each of the calculating/processing portions 250, 250 includes the data accumulating/distributing portion 31, the temperature analyzing portion 32, the rotation analyzing portion 33, the filtering processing portion 34, the vibration analyzing portion 35, the comparing/deciding portion 252, and the internal data saving portion 37. These portions except the comparing/deciding portion 252 have the equivalent functions to those in the first embodiment.

The data accumulating/distributing portion 31 receives the electric signals fed from respective sensing elements and accumulates them temporarily, and also has collecting and distributing functions of allocating the signal to any of the analyzing portions 32, 33, 35 in response to the type of the signal. Various signals are A/D-converted into the digital signal by an A/D converter (not shown) before they are fed to the data accumulating/distributing portion 31, then are amplified by an amplifier (not shown), and then are sent to the data accumulating/distributing portion 31. In this event, the A/D conversion and the amplification may be applied in reverse order.

The temperature analyzing portion 32 calculates the temperature of the bearing 211 based on the output signal from the sensing element that senses the temperature information 12, and then transmits the calculated temperature to the comparing/deciding portion 252. The analyzing portion 32 has a temperature conversion table that responds to characteristics of the sensing elements, and calculates the temperature data based on a level of the sensed signal.

The rotation analyzing portion 33 calculates the rotation speed of the inner ring 214, i.e., the axle 224, based on the output signal from the sensing element that senses the rotation speed information J4, and then transmits the calculated rotation speed to the comparing/deciding portion 252. In this case, when the sensing element is composed of an encoder fitted to the inner ring 214, a magnet fitted to the outer ring 216, and a magnetism sensing element, the signal output from the sensing element is given as a pulse signal that responds to a shape of the encoder and the rotation speed. The rotation analyzing portion 33 has a predetermined transformation function or transformation table in response to a shape of the encoder, and then calculates the rotation speed of the inner ring 214 and the axle 224 in compliance with the function or the table.

The vibration analyzing portion 35 executes the frequency analysis of the vibration generated in the bearing 211, based on the output signal from the sensing element that senses the vibration information J3. More particularly, the vibration analyzing portion 35 is an FFT calculating portion for calculating the frequency spectrum of the vibration signal, and calculates the frequency spectrum of the vibration based on the FFT algorithm. Then, the calculated frequency spectrum is transmitted to the comparing/deciding portion 252. Also, the vibration analyzing portion 35 may execute the absolute-value process and the envelope process as the preprocessing of FFT, and may convert the frequency spectrum into the frequency component necessary for the diagnosis only. The vibration analyzing portion 35 may also output the envelope data obtained after the envelope process to the comparing/deciding portion 252, as the case may be.

Normally, the abnormal frequency band of the vibration generated due to the rotation of the bearing are decided depending upon a size of the bearing, the number of the rolling elements, etc. The relationships between the defects of respective members of the bearing and the abnormal vibration frequencies generated in respective members are given as shown in FIG. 4. In the frequency analysis, the maximum frequency at which the Fourier transform can be applied (Nyquist frequency) is decided according to the sampling time. Thus, preferably the frequency that is in excess of the Nyquist frequency should not be contained in the vibration signal. Therefore, the present embodiment is constructed such that the filtering processing portion 34 is provided between the data accumulating/distributing portion 31 and the vibration analyzing portion 35, then a predetermined frequency band is cut out by the filtering processing portion 34, and then the vibration signal containing only the cut-out frequency band is transmitted to the vibration analyzing portion 35. When the axle is rotating at a low speed in the railway vehicle, only the frequency component of 1 kHz or less, for example, may be extracted.

In FIG. 39, the temperature analyzing portion 32, the rotation analyzing portion 33, and the vibration analyzing portion 35 are illustrated. The analyzing portions may be provided in answer to the information that are sensed by respective sensing elements in the sensor unit.

The comparing/deciding portion 252 compares/collates the results analyzed by the temperature analyzing portion 32, the rotation analyzing portion 33, and the vibration analyzing portion 35 with the information as the diagnosis reference, which is used to check the presence or absence of the abnormality of the bearing, every first time period ti to provisionally diagnose whether or not the abnormality is generated in the bearing. Also, the comparing/deciding portion 252 transmits the provisional diagnosis results, which have been compared/collated every first time period $t_1$, to the internal data saving portion 37 to save them.

In addition, when the comparing/deciding portion 252 has executed the comparison/decision predetermined number of times or a second time period $t_2$ that is longer than the first time period ti has elapsed, such comparing/deciding portion 252 makes the total evaluation, in which the bearing is considered as the abnormal state when the number of times the bearing is diagnosed provisionally as the abnormality exceeds a threshold value, based on the provisional diagnosis results saved in the internal data saving portion 37, and thus diagnoses the presence or absence of the abnormality in the bearing and its abnormal location. In this event, the total evaluation may be constructed to decide an extent of abnormality based on the number of times the bearing is diagnosed provisionally as the abnormal state and then diagnose the presence or absence of the abnormality and its abnormal location.

More specifically, the comparing/deciding portion 252 compares/collates the frequency spectrum of the vibration calculated by the vibration analyzing portion 35 with the reference values saved in the internal data saving portion 37 every first time period $t_1$ to provisionally diagnose whether or not the abnormal vibration is being generated. Where the reference values are data values of frequency components due to the wear and the damage of the particular location of the bearing calculated based on the rotation speed signal of the period signal as the operating signal of the machinery facility.

As the provisional diagnosis processing method executed by the comparing/deciding portion 252 based on the vibration information, any one of above methods (1) to (3) and (5) to (6) may be employed.

The comparing/deciding portion 252 executes the comparison/collation every first time period $t_1$ by using the above methods (1) to (3) and (5) to (6), and then transmits the provisional diagnosis result about the presence or absence of the abnormality to the internal data saving portion 37 to save the result therein. Also, when the comparing/deciding portion 252 has executed the comparison/decision predetermined number of times or a second time period $t_2$ that is longer than the first time period $t_1$ has elapsed, such comparing/deciding portion 252 makes the total evaluation, in which the bearing is considered as the abnormal state when the number of times the bearing is diagnosed provisionally as the abnormality exceeds a threshold value, based on the provisional diagnosis results saved in the internal data saving portion 37, and thus diagnoses the presence or absence of the abnormality in the bearing and its abnormal location.

In this case, the result of each sensed object in the comparing/deciding portion 252 may be saved in a storing medium such as memory, HDD, or the like, or the result may be transmitted to the controlling/processing portion 40.

The controlling/processing portion 40 has the result outputting portion 42 as a displaying means for displaying the analyzed result and the decision result of the calculating/processing portions 250, 250 in a predetermined display mode, and the controlling portion 41 for feeding back the control signal responding to the decision result of the comparing/deciding portion 252 to the control system that controls the operation of the driving mechanism of the vehicle into which the bearing 211 is fitted.

More particularly, the result outputting portion 42 informs of the analyzed result and the decision result of the calculating/processing portion 250 by the monitor, the image display, the printing output to the printer, and also informs of the abnormality by the alarm device such as the light, the buzzer, or the like when the decision result of the comparing/deciding portion 252 indicates that the abnormality exists.

For example, when the decision result of the comparing/deciding portion 252 indicates that the abnormality is present, the controlling portion 41 feeds the control signal indicating the travel stop of the vehicle, the reduction of speed, or the like to a travel controller of the vehicle in response to an extent of the abnormality. In the present embodiment, a plurality of sensor units 22 measures continuously the condition of the bearing of the bearing unit, and the calculating/processing portion 250 conducts sequentially the abnormality diagnosis based on the measured data. Therefore, the controlling/processing portion 40 informs of the abnormality immediately to execute the control of the vehicle when the abnormality occurs. In other words, a flow of sensing, analyzing, deciding, and result outputting are carried out in real time.

In this case, any means may be employed to transmit the signal between the sensing/processing portion 20, the calculating/processing portion 250, and the calculating/processing portion 250 if the signal can be transmitted/received precisely. The cable may be employed or the radio may be employed in light of the network.

Next, the diagnosis process in the condition monitoring method in the present embodiment will be explained with reference to FIG. 40 hereunder.

First, a counter in the microcomputer is initialized into n=0 (step S601), and the diagnosis is started. Then, the signal such as the sound, the vibration, or the like generated from the railway vehicle facility 210 and sensed by the sensor in the sensing/processing portion 20 is input into the microcomputer (step S602). Then, the signal generated from the railway vehicle facility 210 is converted into the digital signal by the A/D converter (step S603). Then, the digital signal is subjected to the amplifying process by the amplifier (step S604). After the amplifying process is executed, the counted value of the counter is set to n=n+1 (step S605). Then, the filtering process is applied to the amplified digital signal by the filtering processing portion 34 (step S606), and thus the noise component is removed or the particular frequency component is extracted.

Then, the digital signal, after the filtering processing, is sent to the vibration analyzing portion 35; and the analyzing process such as the enveloping process, the frequency analysis, etc. are executed there (steps S607, S608). Thus, the frequency components based on the actually measured data representing the signals sensed from the railway vehicle facility 210 are derived. Meanwhile, the rotation speed signal of the railway vehicle facility 210 is sensed by the sensor in the sensing/processing portion 20 (step S609). Then, a theoretical frequency component generated due to the damage of the railway vehicle facility 210 and serving as a reference value is calculated based on the rotation speed signal (step S610). Then, the frequency components based on the actually measured data are compared/collated with the theoretical frequency component calculated in step S610 by the comparing/deciding portion 252 every first time period $t_1$ according to any of the above approaches (1) to (3) and (5) to (6) (step S611), and the provisional diagnosis to check whether or not the abnormality is present in the particular location of the railway vehicle facility is executed. The result is saved together with the counter value n in the internal data saving portion 37 (step S612).

Then, the counter value n is compared with a predetermined number of times N (step S613). Then, if the counter value n is smaller than the predetermined number of times N, the process goes back to step S602 and then the processes in steps S602 to S612 are repeated. In contrast, if the counter value n is in excess of the predetermined number of times N, the evaluation in which the bearing is considered as the abnormal state when the number of times the bearing is diagnosed as the abnormal state in the provisional diagnosis exceeds the threshold value (referred to as the "total evaluation" hereinafter) is executed by using N saved results, and thus the presence or absence of the abnormality in the railway vehicle facility 210 and its location are diagnosed (step S614). Then, the diagnosis result is saved or is fed to the controlling/processing portion 40, and then the diagnosis result is displayed (step S615) or the feedback control is applied by the controlling portion 41. Thus, the diagnosis is ended.

As a consequence, in the condition monitoring method in the present embodiment, the total evaluation in which the presence or absence of the abnormality and its location are diagnosed by using plural compared/collated results is employed. Therefore, the influence of the impulsive noise, etc. upon the diagnosis can be lessened and thus the monitoring can be executed effectively with good precision.

In the present embodiment, since the frequency component is compared/collated every first time period $t_1$, the timing in the total evaluation may be evaluated by employing any second time period $t_2$ longer than the first time period $t_1$ instead of the predetermined number of times N.

Also, the amplifying process and the filtering process in the condition monitoring method in the present embodiment may be executed arbitrarily, and thus carried out as the case may be.

Figure 40:
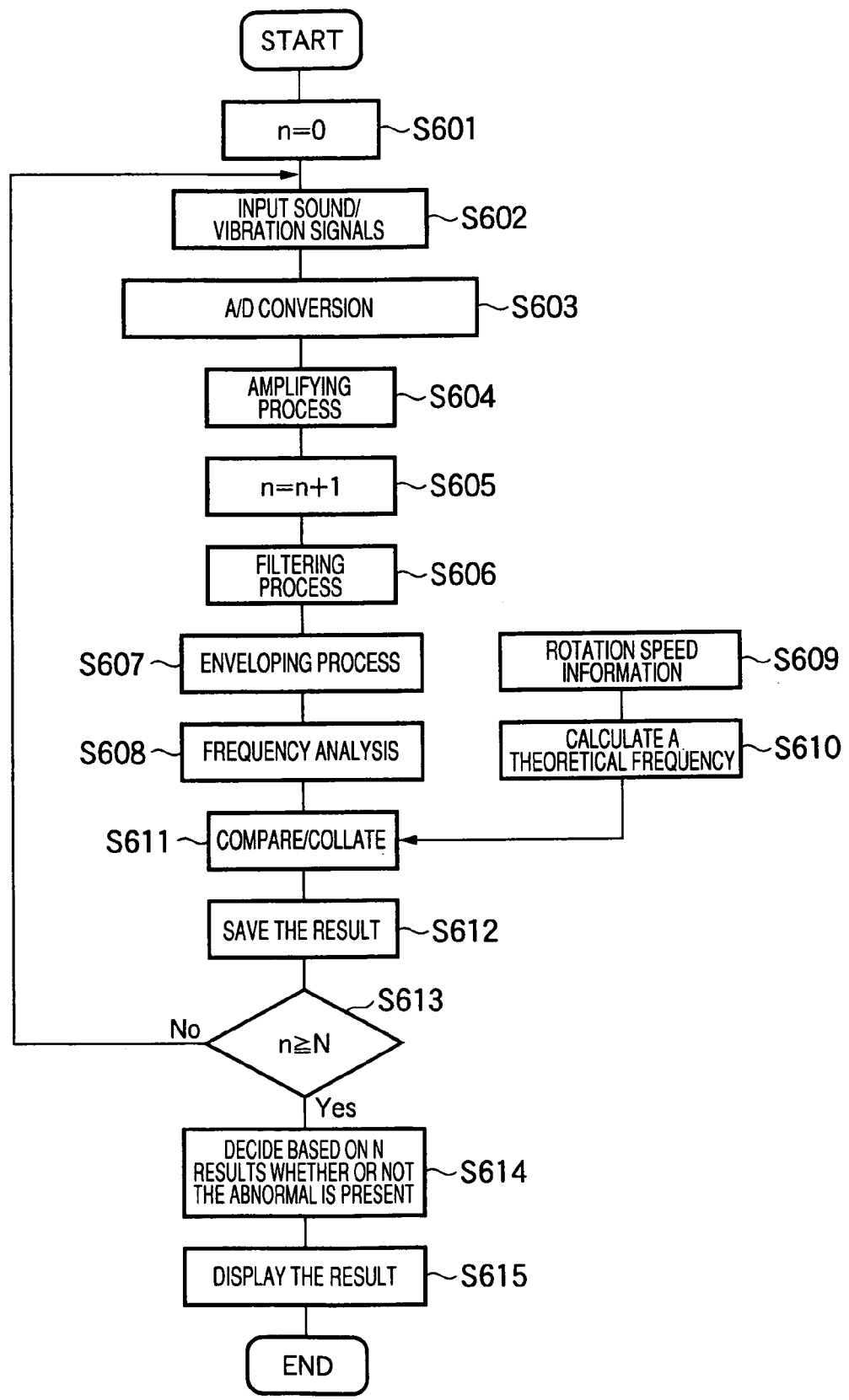
FIG. 40 is a flowchart showing procedures of a diagnosis process in a condition monitoring method.

In addition, in step S614 in FIG. 40, the total evaluation in which the presence or absence of the abnormality and its location are decided by comparing the number of times the bearing is provisionally diagnosed as the abnormal state with the threshold value is employed. Alternately, as a variation of the present embodiment, the condition monitoring can be executed by using the total evaluation in which an extent of the damage is decided based on the number of times the bearing is provisionally diagnosed as the abnormal state. As a result, the maintenance can be applied on schedule to the machinery facility an operation of which is not immediately stopped, or the like.

In the present embodiment, the condition monitoring is applied to the double row tapered roller bearing in the railway vehicle facility. But the condition monitoring may also be applied to other machinery facilities such as a machine tool, the windmill, and others.

Also, the double row tapered roller bearing as the rolling bearing is employed as the rotating body or the sliding member. But the condition monitoring method and system can also be applied to the ball screw, the linear guide, the linear ball bearing, or the like in addition to the rolling bearing. In this case, as the operation signal of the machinery facility used to calculate the reference value in the comparison/collation, the rotation speed signal is used in the case of the rolling bearing, the ball screw, or the like as the rotating body whereas the moving speed is used in the case of the linear guide, the linear ball bearing, or the like as the sliding member.

Further, if the sensor including at least one sensing element selected from at least sound, temperature, vibration, rotation speed, distortion, AE, and moving speed is provided, the presence or absence of the abnormality can be analyzed by the condition monitoring method and system. But it is preferable that the presence or absence of the abnormality should be analyzed by using at least one of the sensing elements of sound, vibration, and AE. Also, from an aspect of capable of utilizing the past abnormality database, it is desired to analyze the presence or absence of the abnormality by using the vibration information. However, in case the abnormality should be sensed in an initial stage of occurrence of the minute crack or in case the internal defect should be sensed, it is appropriate to employ the AE information in place of the vibration information. If the temperature information is employed in combination with the vibration information or the AE information, such information can have the larger effect than the case where such information is employed solely.

<Twelfth Embodiment>

Next, a machinery facility abnormality diagnosis system according to a twelfth embodiment of the present invention will be explained hereunder. In this event, the same reference symbols are affixed to the portions similar to those in the first embodiment, and thus their redundant explanations will be omitted or simplified hereunder.

Figure 41:
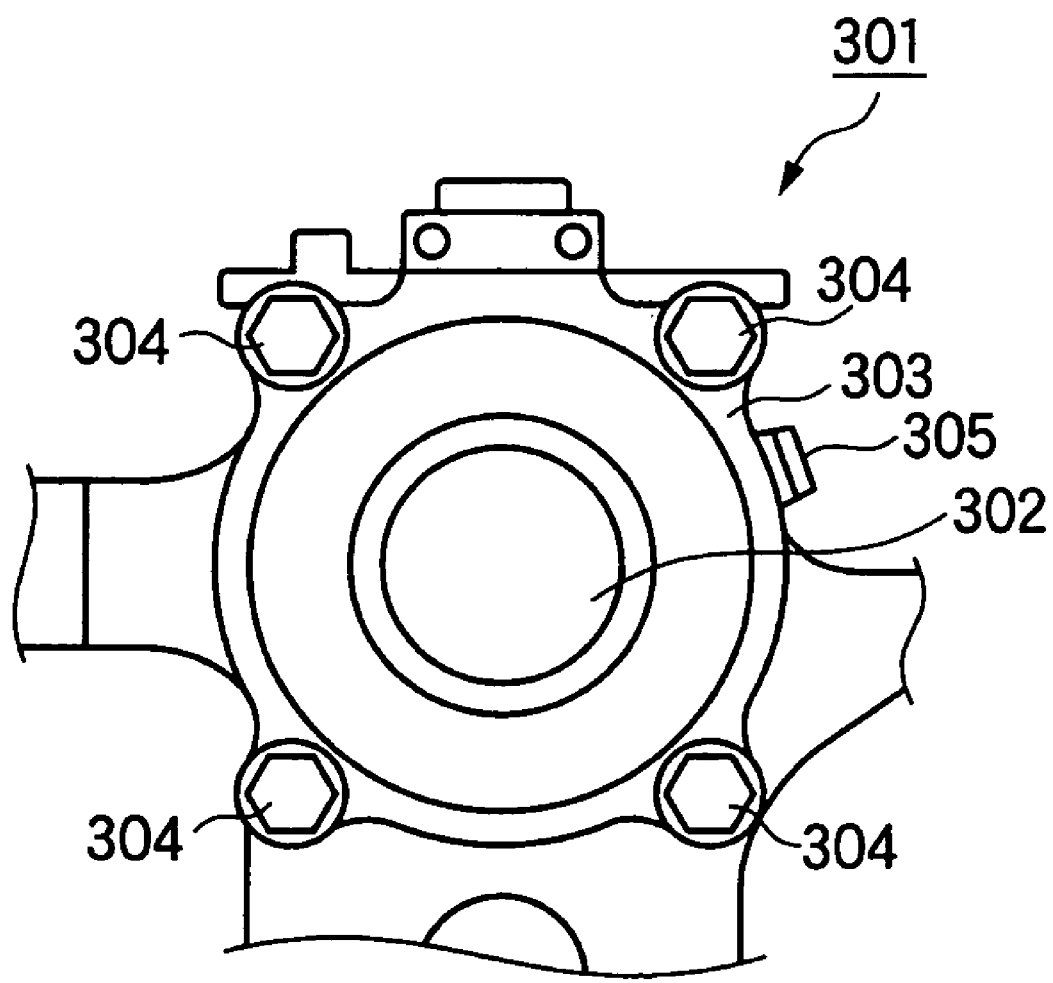
FIG. 41 is a view showing a bearing housing of a railway vehicle bearing unit serving as a machinery facility to which an abnormality diagnosis system according to a twelfth embodiment of the present invention is applied.

FIG. 41 is a view showing a bearing housing 301 of the railway vehicle bearing unit serving as the machinery facility to which an abnormality diagnosis system 310 according to the twelfth embodiment of the present invention is applied. The bearing housing 301 is fitted to cover an end portion of the axle of the railway vehicle, and holds rotatably the axle of the railway vehicle via a bearing (not shown in FIG. 41) incorporated into the inside. Also, a cover 302 for covering the end portion of the axle of the railway vehicle is fitted to a housing 303 in the bearing housing 301.

The bearing housing 301 is fixed by four bolts 304 provided to four corners via the housing 303. Also, a hole used to measure the temperature of the bearing is provided to a side surface of the housing 303 and is stopped with a bolt 305. In the present embodiment, the sensor unit 22 of the above sensing/processing portion 20 is fitted to an end surface of the bolt 304 or the bolt 305, and the signals generated from the bearing in the bearing housing are sensed by respective sensors in the sensor unit 22.

Figure 42:
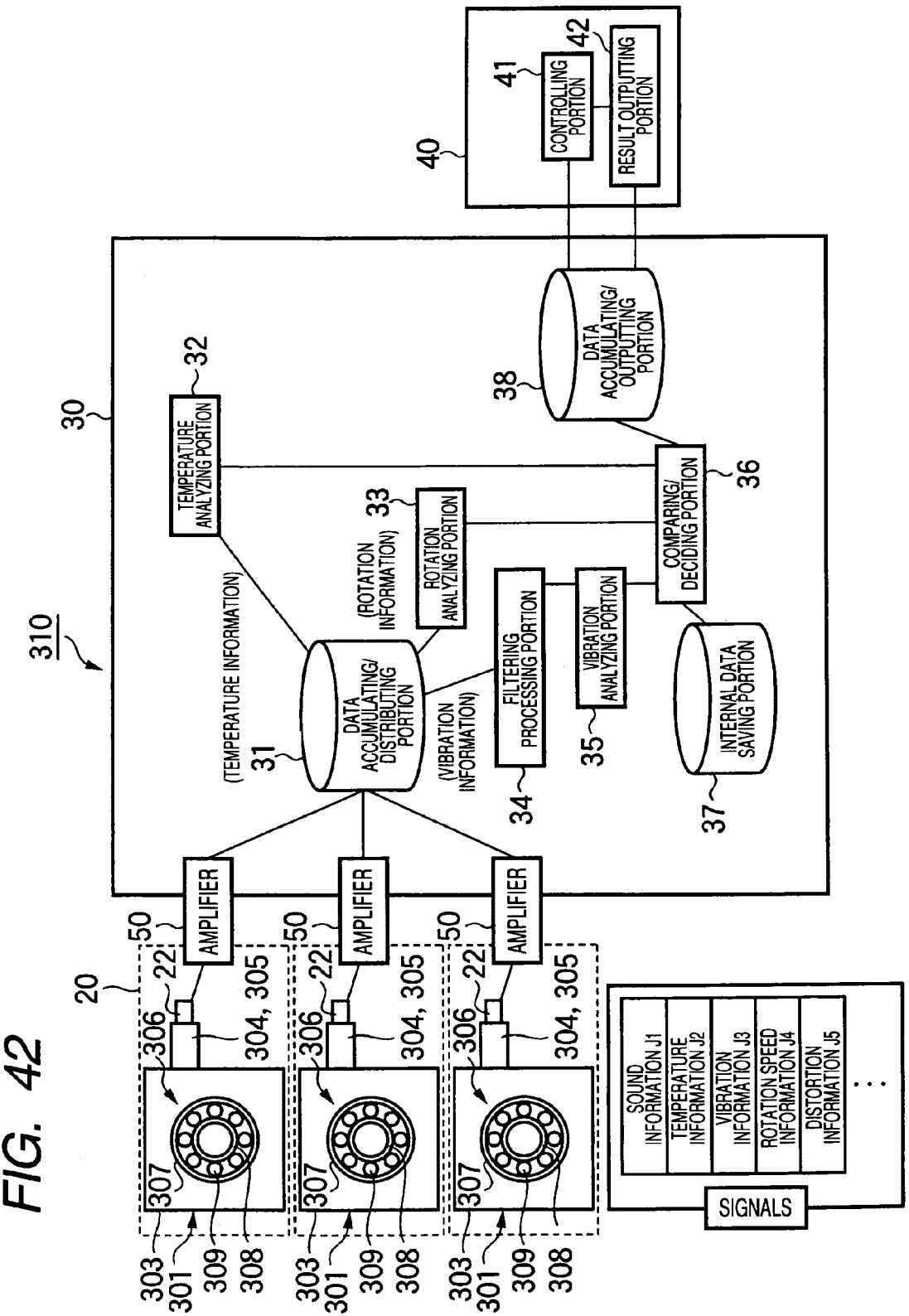
FIG. 42 is a view showing a railway vehicle abnormality diagnosis system in the twelfth embodiment.

FIG. 42 is a view showing an overall configuration of the abnormality diagnosis system 310 using the sensor unit 22 in the present embodiment. As shown in FIG. 42, a rolling bearing 306 is put into the bearing housing 301. The rolling bearing 306 is constructed by arranging rolling elements 309 made of a plurality of balls or rollers between an outer ring 307 fitted into the housing 303 and an inner ring 308 fitted onto the axle of the railway vehicle. Thus, the bearing housing 301 bears rotatably the axle of the railway vehicle via the rolling bearing 306.

As shown in FIG. 42, the sensor unit 22 is fitted to the end surface of the bolt 304 or 305 secured to the surface of the housing 303. The sensor unit 22 can be fitted to the end surface of the bolt 304 used to fix the bearing housing, but the sensor unit may be fitted to the end surface of the bolt 305 used to stop the temperature sensing hole, as described above. Normally this bolt 305 is given to every rolling bearing 306 fitted to the inside. For example, in the case of the double row bearing, the fitting location can be selected on the row located on the wheel side, the row located on the motor side, the middle location, or the like according to the purpose. But it is preferable that, for convenience of the fitting operation, the bolt 305 should be fitted to the wheel side and the sensor unit 22 should be provided to the end surface of the bolt 305. Also, the sensor unit 22 can be fitted to not the end surface of the bolt 305 but the side surface or the inside of the hole that is stopped with this bolt 305.

It is preferable that the sensor unit 22 and the bolts 304, 305 should be tightly fitted/fixed without unsteadiness, looseness, or the like. More particularly, in view of the running conditions, the fitting conditions, characteristics of the sensor, and so on, the suitable fitting approach can be selected appropriately among various approaches such as screwing, bonding, magnet, inserting, molding integrally with the bolt, etc.

Also, in case the fitting location of the sensor unit 22 is chosen in the noisy area, preferably the sensor unit 22 should be fitted to be isolated from the circumference. If the sensor can be isolated from the circumference, the noise can be reduced and also the SN ratio can be improved.

In addition, in order to execute the sensing at the high SN ratio, it is preferable that the sensor unit 22 should be fitted in the loading range of the rolling bearing 306, as indicated by A1 in FIG. 5, like the first embodiment. If the sensor unit 22 is fitted to the portion to which the load is applied (loading range), the signal can be sensed with good sensitivity and thus the higher-precision measurement can be done.

Also, in case the sensor is fitted inevitably in the non-loading range, e.g., when no space is found in the loading range to fit the sensor, when the high-tension cable that emits the noise is provided in the loading range, or the like, it is preferable that the sensing sensitivity of the signal can be enhanced by executing the filtering process.

Here, the sensor unit 22 has the similar structure/functions to those of the sensor unit used in the first embodiment. Also, the calculating/processing portion 30 and the controlling/processing portion 40 shown in FIG. 42 have the similar structure/functions to those of the sensor unit used in the first embodiment.

According to the abnormality diagnosis system 310 of the present embodiment, the sensing/processing portion 20 consisting of the sensor unit 22 that is fixed to the end surface of the bolt 304 or 305, which is screwed into the housing 303 of the bearing housing 301 that supports the rolling bearing 306 as the rotating body in the railway vehicle, and has the sensing element to output the signal generated from the rolling bearing 306 as the electric signal, the calculating/processing portion 30 for conducting the abnormality diagnosis of the bearing unit based on the output of the sensor unit 22, and the controlling/processing portion 40 for feeding back the control signal to the control system of the railway vehicle based on the decision result of the calculating/processing portion 30 are provided.

More specifically, like the first embodiment, the calculating/processing portion 30 includes the data accumulating/distributing portion 31 for accumulating the electric signal fed from the sensing/processing portion 20 and distributing the signal to the suitable distributing route according to the type of the signal, the analyzing portions 32, 33, 35 for calculating the predetermined physical quantity in regarding to the railway vehicle as the machinery facility based on the electric signal distributed from the data accumulating/distributing portion 31, the internal data saving portion 37 as the first data saving portion in which machine equipment data concerning to the machine equipment are saved, the comparing/deciding portion 36 for conducting the abnormality diagnosis of the machine equipment by comparing the physical quantity calculated by the analyzing portion with the machine equipment data saved in the internal data saving portion, and the data accumulating/outputting portion 38 as the second data saving portion for saving the analyzed result by the analyzing portion and the abnormality diagnosis result by the comparing/deciding portion.

According to the abnormality diagnosis system 310, since the physical information about the rolling bearing 306 are collected by using the sensor unit 22 and the abnormality of the rolling bearing 306 is diagnosed based on the physical information to execute the control, the defect of the rolling bearing 306 can be sensed without decomposition of the bearing housing 301. Therefore, the time and labor required for the decomposition and the assembling of the bearing housing 301 can be reduced and also the damage of the rolling bearing 306 and the bearing housing 301 attendant upon the assembling after the decomposition can be prevented. Also, in the present embodiment, since the diagnosis is made by the abnormality diagnosis system 310 based on the predetermined references, it is possible to find the defect that the visual inspection may overlook.

Also, according to the present embodiment, since the sensor unit 22 is fixed onto the bolt 304 or 305, there is no need to provide particularly the flat surface, onto which the sensor unit 22 is fitted, on the bearing housing 301. Therefore, the sensor unit 22 can be fitted without reform of the bearing housing 301. As a result, the abnormality diagnosis can be conducted by installing the sensor unit 22 of the abnormality diagnosis system 310 into the bearing housing 301 without extra time/labor and cost.

In the present embodiment, explanation is made of the rolling bearing in the bearing housing of the railway vehicle as an example, but the present invention is not limited to this. The present invention can also be applied to other rotating parts (gear, wheel itself) of the railway vehicle, the windmill, the reduction gear, the electric motor, the ball screw, the linear guide, and others.

Also, the calculating/processing portion 30 may have the functions of the calculating/processing portion achieved by the microcomputer 250 in the eleventh embodiment.

Figure 43:
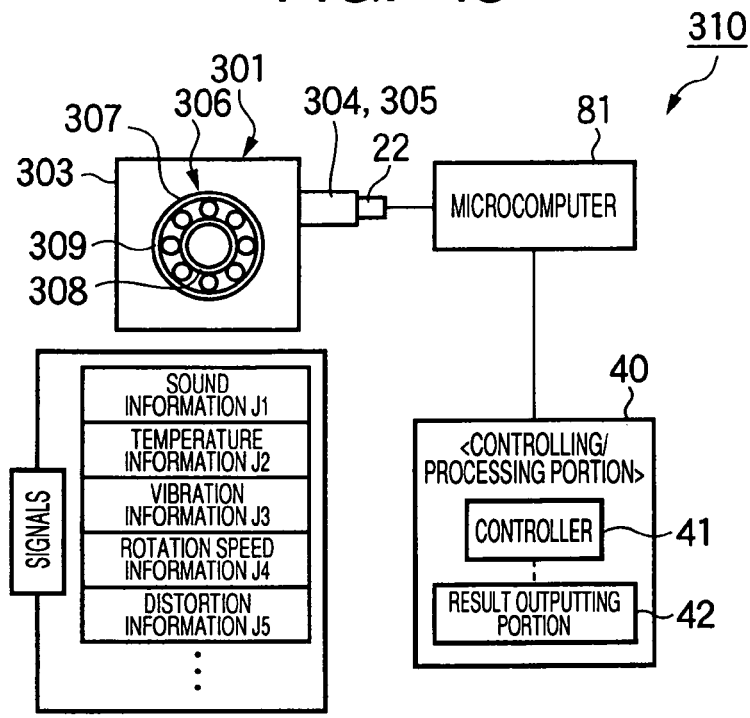
FIG. 43 is a view showing a variation of the abnormality diagnosis system according to the twelfth embodiment of the present invention.

Also, as shown in FIG. 43, the calculating/processing portion 30 of the abnormality diagnosis system 310 in the present embodiment may be constructed by the one-chip or one-board microcomputer 81 shown in the fifth to tenth embodiments, or may be constructed by the IC chip. In addition, the controlling/processing portion 40 may also be constructed by the one-chip or one-board microcomputer or the IC chip. Also the microcomputer in which the calculating/processing portion 30 and the controlling/processing portion 40 are integrally provided may be loaded on the machine equipment such as the vehicle, or the like.

Figure 44:
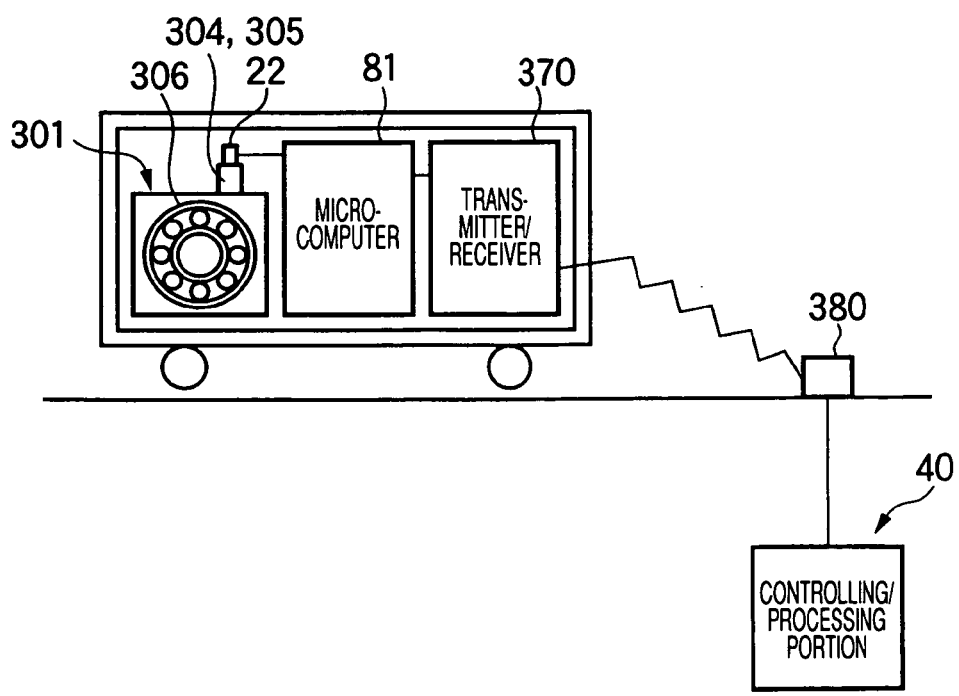
FIG. 44 is a view showing another variation of the abnormality diagnosis system according to the twelfth embodiment of the present invention.

Also, as shown in FIG. 44, the controlling/processing portion 40 may be removed from the vehicle and installed on the ground, and then the radio communication may be established between a transmitter/receiver 370 provided on the vehicle and a transmitter/receiver 380 provided adjacent to the railway. In this case, the functions corresponding to the controlling/processing portion 40 can be provided to the information processing center provided on the ground, for example. This information center may be constructed to receive the information from the microcomputers 81 provided to a plurality of vehicles respectively and to collectively control a plurality of vehicles intensively, for example. In this case, the ID number, or the like may be added to the data sent out from the vehicles respectively to identify the information of respective vehicles. Similarly the sensor unit 22 and the microcomputer 81 may be connected via radio communication.

As a result, the signal transmission between the sensing/processing portion 20 and the calculating/processing portion 30 or the calculating/processing portion 30 and the controlling/processing portion 40 can be made without a wire connection.

<Thirteenth Embodiment>

Figure 45:
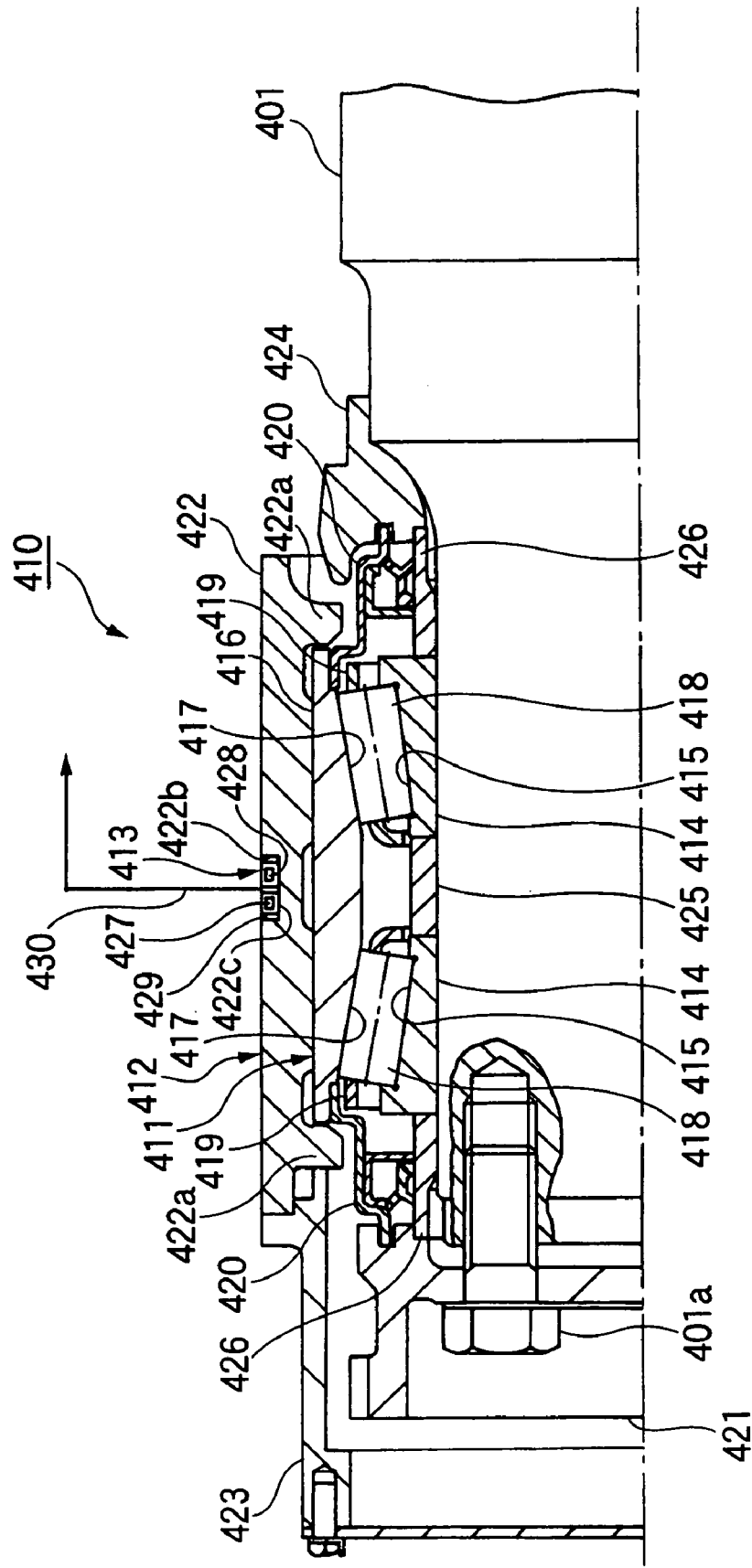
FIG. 45 is a schematic view showing a bearing unit according to a thirteenth embodiment of the present invention.

Next, a bearing unit according to a thirteenth embodiment of the present invention will be explained hereunder. As shown in FIG. 45, a bearing unit 410 according to a thirteenth embodiment of the present invention is constructed by a double row tapered roller bearing 411, a bearing housing 412 constituting a part of the carriage for the railway vehicle, and an abnormality sensing means 413.

The double row tapered roller bearing 411 has a pair of inner rings 414, 414 having inner ring raceway surfaces 415, 415 inclined like a tapered outer surface on their outer peripheral surfaces, a single outer ring 416 having a pair of outer ring raceway surfaces 417, 417 inclined like a tapered outer surface on their inner peripheral surfaces, tapered rollers 418 as the rolling elements that are arranged in plural between the inner ring raceway surfaces 415, 415 of the inner rings 414, 414 and the outer ring raceway surfaces 417, 417 of the outer ring 416 in double row, annular pressed retainers 419, 419 for holding rollably the tapered rollers 418, and a pair of sealing members 420, 420.

A radial load applied by weights of various members, etc. and any axial load arc imposed onto the double row tapered roller bearing 411. An upper portion of the outer ring 416 is the loading range of the bearing.

The bearing housing 412 consists of an axle end member 421, a housing 422, a cover 423, and a shroud 424.

An inner ring spacer 425 is arranged between the inner rings 414, 414. Also, inner ring spacers 426, 426 are arranged on both outer sides of the inner rings 414, 414 in the axial direction. An axle 401 is fitted into the inner rings 414, 414 and the inner ring spacers 425, 426, 426. The inner ring raceway surfaces 415, 415 of the inner rings 414, 414 restrict the movement of the tapered rollers 418 in the axial direction.

The outer ring raceway surfaces 417, 417 of the outer ring 416, the inner ring raceway surfaces 415, 415 of the inner rings 414, 414, and the tapered rollers 418 are positioned such that vertexes located on prolonged lines of respective tapered surfaces are converged on one point on the axis line.

Out of the sealing members 420, 420, one sealing member 420 arranged on the top end portion side of the axle 401 is fitted between the outer end portion of the outer ring 416 and the axle end member 421.

The other sealing member 420 arranged on the counter top end portion side of the axle 401 is fitted between the outer end portion of the outer ring 416 and the shroud 424.

The axle end member 421 is fixed by screwing bolts 401*a* into the top end portion of the axle 401 to cover the inner ring spacer 426 arranged at the top end portion of the axle 401.

The housing 422 constitutes a side frame of the railway vehicle carriage, and is formed like the annular ring to cover the outer peripheral surface of the outer ring 416. A pair of projected walls 422*a*, 422*a* being projected into the inner peripheral surface are mounted on both side end portions of the outer ring 416. Then, a recess portion 422*b* in which the abnormality sensing means are housed is formed on the outer peripheral surface of the housing 422 corresponding to the center portion of the double row tapered roller bearing 411 in the axial direction. A flat surface 422c is formed on a bottom portion of the recess portion 422b.

The cover 423 is put on the top end portion of the housing 422. The shroud 424 is positioned between the end portion of the housing 422 and the axle 401 to cover the other sealing member 420 on the counter top end portion side of the axle 401.

The abnormality sensing means 413 is a composite sensor in which a temperature sensor 427 and a vibration sensor 428 are integrally provided. The temperature sensor 427 is a non- contact type temperature measuring element such as a thermistor temperature measuring element, a platinum resistance temperature sensor, a thermocouple, or the like. The vibration sensor 428 is a vibration measuring element such as a piezoelectric element, or the like.

Also, since the temperature sensor 427 and the vibration sensor 428 are aligned in the axial direction of the bearing and resin-molded in the recess portion 422b of the housing 422, such temperature sensor 427 and such vibration sensor 428 are integrally molded in a case 429. Thus, the abnormality sensing means 413 is fitted in the loading range of the housing 422 and the double row tapered roller bearing 411 in the center portion in a bearing width. The molding material used in the resin molding is the material that is rich in the waterproof property, the heat resisting property, and the insulating property.

The temperature sensor 427 senses the temperature of the double row tapered roller bearing 411 via the housing 422 to generate the temperature data signal (voltage signal). The temperature data signal generated by the temperature sensor 427 is transferred to the external controlling portion via a signal carrying means 430 provided in the case 429, and is used to sense the seizure abnormality of the double row tapered roller bearing 411. Here, as the temperature sensor 427, a temperature fuse that does not conduct by causing either a contact of a bimetal to disconnect or a contact to fuse when the atmospheric temperature exceeds a specified value may be employed. In such case, when the temperature of the device exceeds a specified value, conduction of the temperature fuse is cut off and thus the temperature abnormality is sensed.

The vibration sensor 428 senses the vibration of the double row tapered roller bearing 411 via the housing 422 to generate the vibration data signal (voltage signal). The vibration data signal generated by the vibration sensor 428 is transferred to the external controlling portion via the signal carrying means 430 provided in the case 429, and is used to sense the flaking of the inner ring raceway surfaces 415, 415 and the outer ring raceway surfaces 417, 417 of the double row tapered roller bearing 411, the fracture of the gear, and the flat wear of the wheel. Here, as the vibration sensor 428, any sensor capable of transforming the vibration such as acceleration, speed, displacement, or the like into the electric signal may be employed. When the vibration sensor is fitted to the device that is often exposed to the disturbance such as the noise, and the like, it is desired that the sensor does not suffer the noise by using the insulation type.

Since the temperature sensor 427 and the vibration sensor 428 are arranged in the case 429 formed by the molding, the entering of the rainwater can be prevented-without fail. Also, since the temperature and the vibration can be sensed during the rotation, the defect of a plurality of parts can be inspected concurrently without overhaul of the system into which the rotating parts are incorporated. Since the vibration-proof property against the vibration applied from the outside can be improved rather than the case where the sensor is fixed to the outside of the housing 422, the reliability of the sensing performance can be improved tremendously. Also, since the sensor is never subjected to the surrounding circumstances such as fitting condition, rainwater, wind pressure, and the like in contrast to the case where respective sensors are fixed with the screws separately, the high-precision signal can be generated at the high SN ratio (signal-to-noise ratio).

Figure 46:
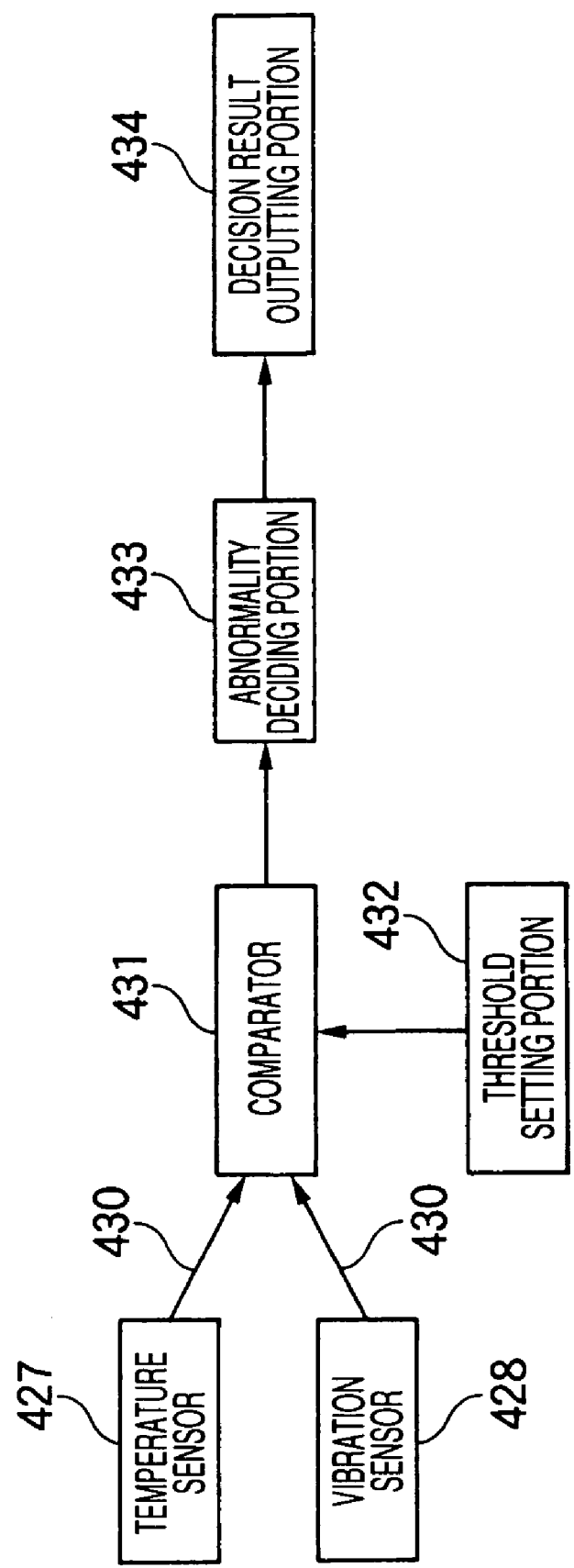
FIG. 46 is a signal processing system diagram in an abnormality sensing means in the bearing unit shown in FIG. 45.

As shown in FIG. 46, in the first signal processing method in the abnormality sensing means 413, the temperature data signal generated by the temperature sensor 427 and the vibration data signal generated by the vibration sensor 428 are input into a comparator 431 via the signal carrying means 430. Then, the temperature data signal value given from the temperature sensor 427 is compared with a predetermined temperature threshold value saved in a threshold setting portion 432 in the comparator 431. Similarly, the vibration data signal value given from the vibration sensor 428 is compared with a predetermined vibration threshold value saved in the threshold setting portion 432. That is, at least one abnormality selected from the temperature sensor 427 and the vibration sensor 428 is sensed by the abnormality sensing means 413. At this time, when the temperature data signal value exceeds the temperature threshold value, a temperature abnormality decision signal is output from an abnormality deciding portion 433 and also a temperature abnormality alarm is output from a decision result outputting portion 434.

Also, when the vibration data signal value exceeds the vibration threshold value, a vibration abnormality decision signal is output from the abnormality deciding portion 433 and also a vibration abnormality alarm is output from the decision result outputting portion 434. The alarm is transferred via cable or radio and then operated. At this time, as the temperature threshold value and the vibration threshold value saved in the threshold setting portion 432 and the temperature/vibration abnormality decision signals output from the abnormality deciding portion 433, the root-mean-square value and the peak value in any time period may be employed.

Figure 47:
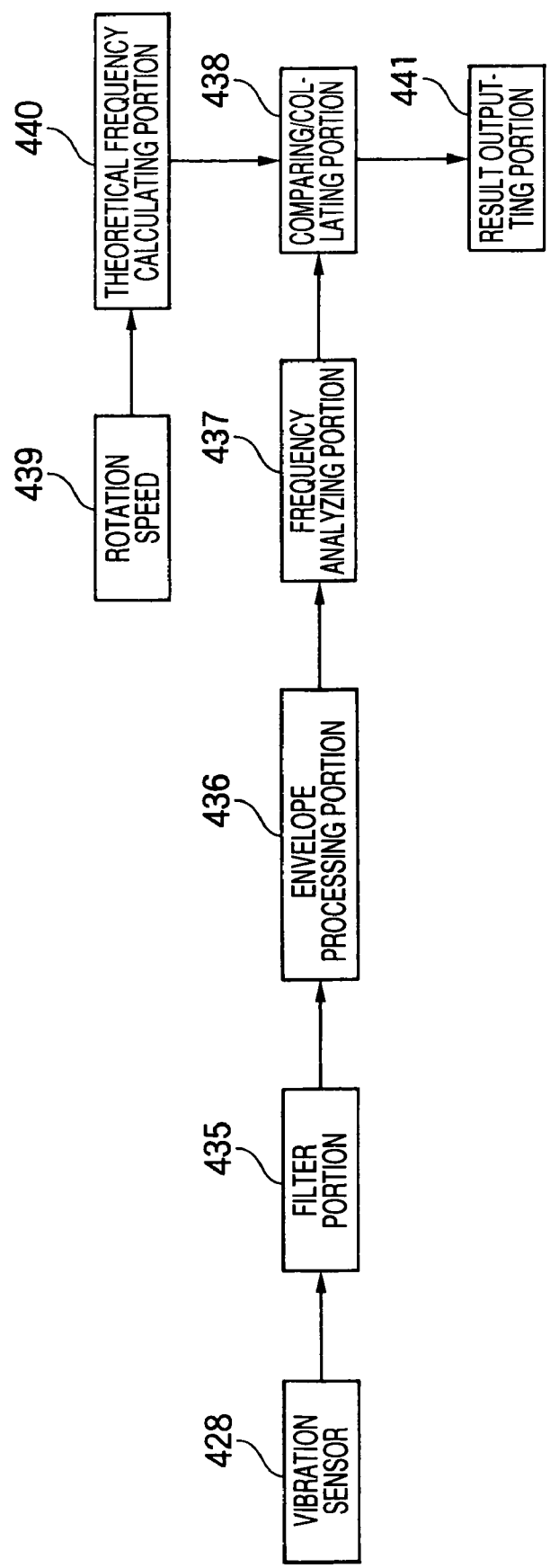
FIG. 47 is a signal processing system diagram using a method different from FIG. 46.

As shown in FIG. 47, in the second signal processing method in the abnormality sensing means 413, the vibration data signal generated by the vibration sensor 428 is amplified, then only a predetermined frequency band is extracted from the vibration data signal by a filtering portion 435 to remove the unnecessary frequency band, and then the resultant signal is input into an envelope processing portion 436. The absolute-value detecting process of detecting the absolute value of the waveform is executed in the envelope processing portion 436, then the frequency analyzing process is executed in a frequency analyzing portion 437, and then the actually measured data are transferred to a comparing/collating portion 438.

Meanwhile, the calculated value data of the frequency components, which are set as those generated due to the abnormality such as one-sided wear, or the like of the bearing, the gear, and the wheel in a theoretical frequency calculating portion 440 based on rotation speed information 439, are transferred to the comparing/collating portion 438. Then, the actually measured data are compared/collated with the calculated value data in the comparing/collating portion 438 to specify the presence or absence of the vibration abnormality and the abnormal location. Then, the presence or absence of the vibration abnormality and the identified location are output from a result outputting portion 441. The information are transferred to the result outputting portion 441 via cable or radio.

In the second signal processing method, for example, the calculation of the frequency components and the comparison/collation can be easily made based on the rotation speed information sensed from the electric motor, or the like and design specifications of the rotating elements parts. Also, various data processes and calculation are applied as the processing of the vibration data signal after the amplification. For example, such processing may be executed by the computer, the dedicated microchip, or the like. In addition, the calculation process may be applied to the sensed data signal after such signal is stored in the saving means such as the memory, or the like.

Also, because it takes much time and labor to exchange the bearing in some machine, such machine cannot be immediately stopped. In this case, in some cases the exchange of the bearing is applied according to a degree of the damage. As the criterion in such case, the root-mean-square value, the maximum value, and the peak factor of the vibration, for example, may be employed with respect to the previously decided reference values.

Also, as the abnormality diagnosis processing method on the basis of the vibration information in the comparing/collating portion 438 shown in FIG. 46, the above approaches (1) to (6) may be employed.

According to the bearing unit 410 in the thirteenth embodiment, since the sensors are molded with the resin in the loading range of the bearing housing 412, particularly in the recess portion 422b formed on the housing 422 of the bearing housing 412 that covers the outer peripheral surface of the outer ring 416, the temperature sensor 427 and the vibration sensor 428 can be integrally formed in a single case 429. Thus, the vibration or temperature information accompanying the rotating condition of the rotating parts can be sensed at the same time by sensing at least one abnormality selected from the temperature sensor 427 and the vibration sensor 428 by means of the abnormality sensing means 413. As a result, the defect of a plurality of parts can be inspected simultaneously still in the actual operating state without overhaul of the system into which the rotating parts are incorporated.

In other words, the abnormality sensing means may be provided in the loading range of the bearing housing. Also, it is preferable that the abnormality sensing means should be secured onto the flat portion provided to a part of the outer peripheral surface of the bearing housing on the loading range side. Like the present embodiment, when the abnormality sensing means is embedded/fixed in the recess portion formed on the bearing housing, preferably such means should be fitted to mold a clearance between the abnormality sensing means and the recess portion. Also, the abnormality sensing means may be arranged on the outer diameter portion of the bearing housing in the loading range and in the center portion of the bearing width.

In addition, in the present embodiment, the case of the abnormality sensing means has a signal carrying means for sending out the sensed signal, and a decision result outputting portion for deciding/outputting the presence or absence of the abnormality based on the signal sent out via the signal carrying means.

Further, the inspection executed based on the vibration information is attained by providing the filtering processing portion for removing the unnecessary frequency band from the vibration waveform from the vibration sensor, the envelope processing portion for detecting the absolute value of the filtered waveform transferred from the filtering processing portion, the frequency analyzing portion for analyzing the frequency of the waveform transferred from the envelope processing portion, the comparing/collating portion for comparing the frequency generated due to the damage calculated based on the rotation speed with the frequency derived based on the actually measured data, and the result outputting portion for identifying the presence or absence of the abnormality and the abnormal location based on the compared result in the comparing/collating portion.

Therefore, the abnormal decision can be made still in the normal state of use without overhaul of the bearing unit 410. As a result, a frequency of the overhauling/assembling operations that require a lot of time and labor can be reduced and thus the maintenance/administrative costs can be reduced largely. Also, the variation of the decision due to a degree of expertise or the individual differences of the person in charge of inspection is in no way generated rather than the visual inspection in the prior art, and thus the reliability of the abnormality diagnosis can be improved dramatically.

<Fourteenth Embodiment>

Next, a bearing unit according to a fourteenth embodiment of the present invention will be explained with reference to FIG. 48 hereunder. In this event, the same reference symbols are affixed to the portions similar to those in the thirteenth embodiment, and thus their redundant explanations will be omitted or simplified hereunder.

Figure 48:
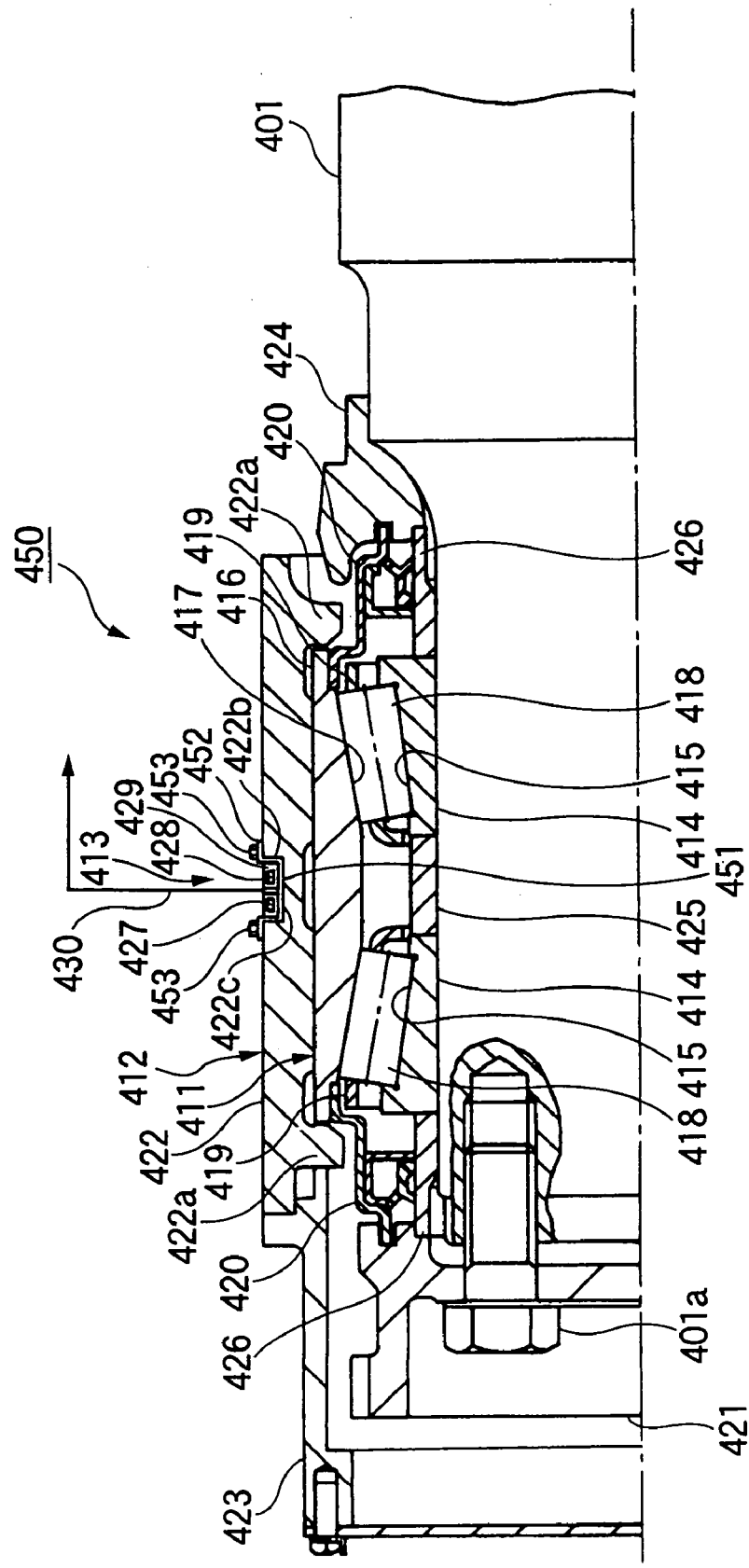
FIG. 48 is a sectional view showing a bearing unit according to a fourteenth embodiment of the present invention.

As shown in FIG. 48, in a bearing unit 450 in the present embodiment, the abnormality sensing means 413 constructed by molding integrally the temperature sensor 427 and the vibration sensor 428 in the case 429 is fixed to the recess portion 422b formed on the outer peripheral surface of the housing 422 via a spacer 451.

The spacer 451 is made of a metal that has the temperature characteristic and the natural vibration characteristic equivalent to the housing 422. The spacer 451 is fixed by tightening screws 453, 453, which are inserted into a flange 452 arranged on the outer peripheral portion of the housing 422, into the housing 422.

In this case, the abnormality sensing means 413 as well as the spacer 451 can be detachably attached to the housing 422. Therefore, when the temperature sensor 427 and the vibration sensor 428 are to be exchanged, the exchanging operation can be executed only by taking out the screws 453, 453 not to consume much time. In the bearing unit 450 in the fourteenth embodiment, the same signal processing as that in the first embodiment is applied.

<Fifteenth Embodiment>

Next, a bearing unit according to a fifteenth embodiment of the present invention will be explained with reference to FIG. 49 hereunder. In this case, the same reference symbols are affixed to the portions similar to those in the thirteenth embodiment, and thus their redundant explanations will be omitted or simplified hereunder.

Figure 49:
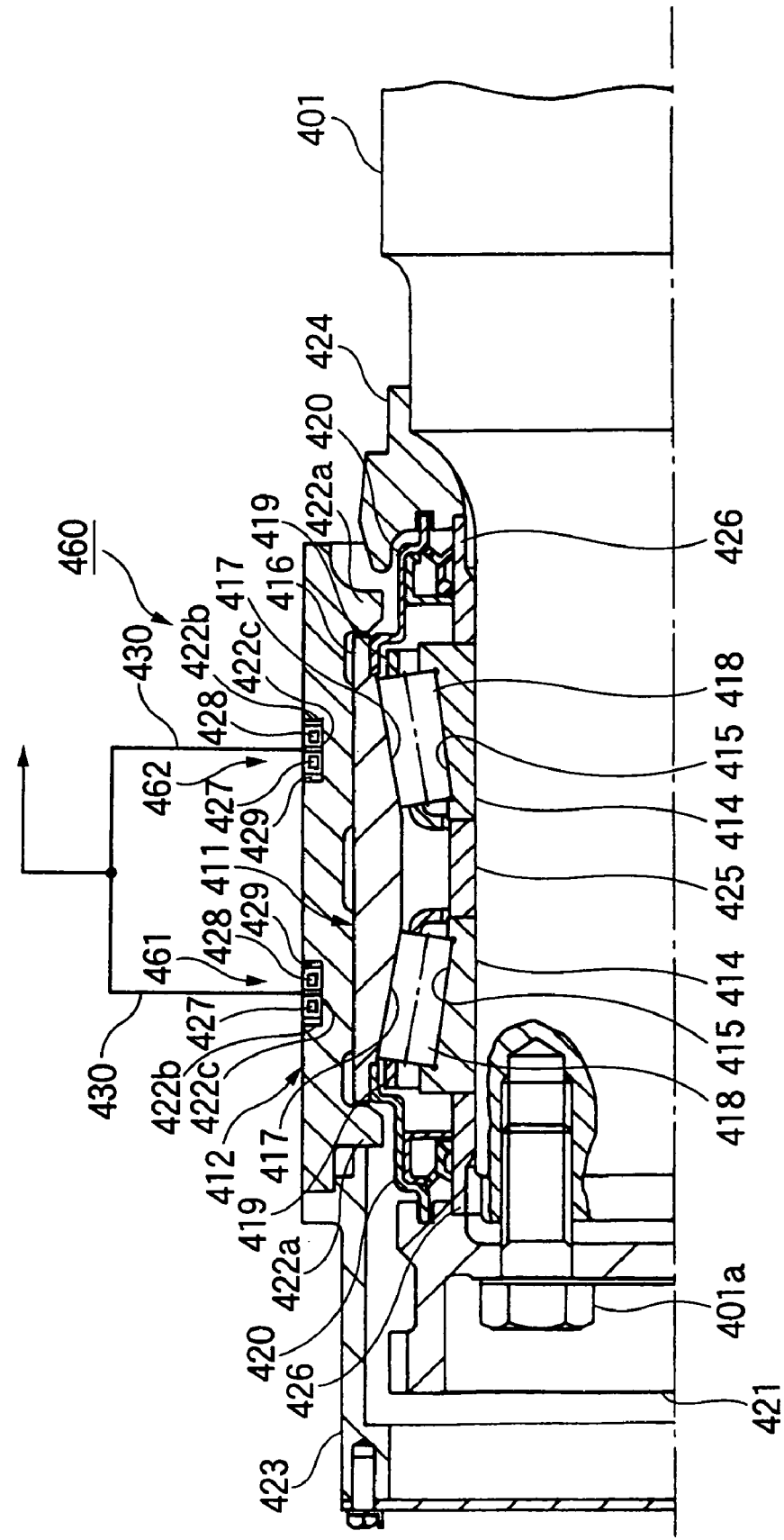
FIG. 49 is a sectional view showing a bearing unit according to a fifteenth embodiment of the present invention.
Figure 50:
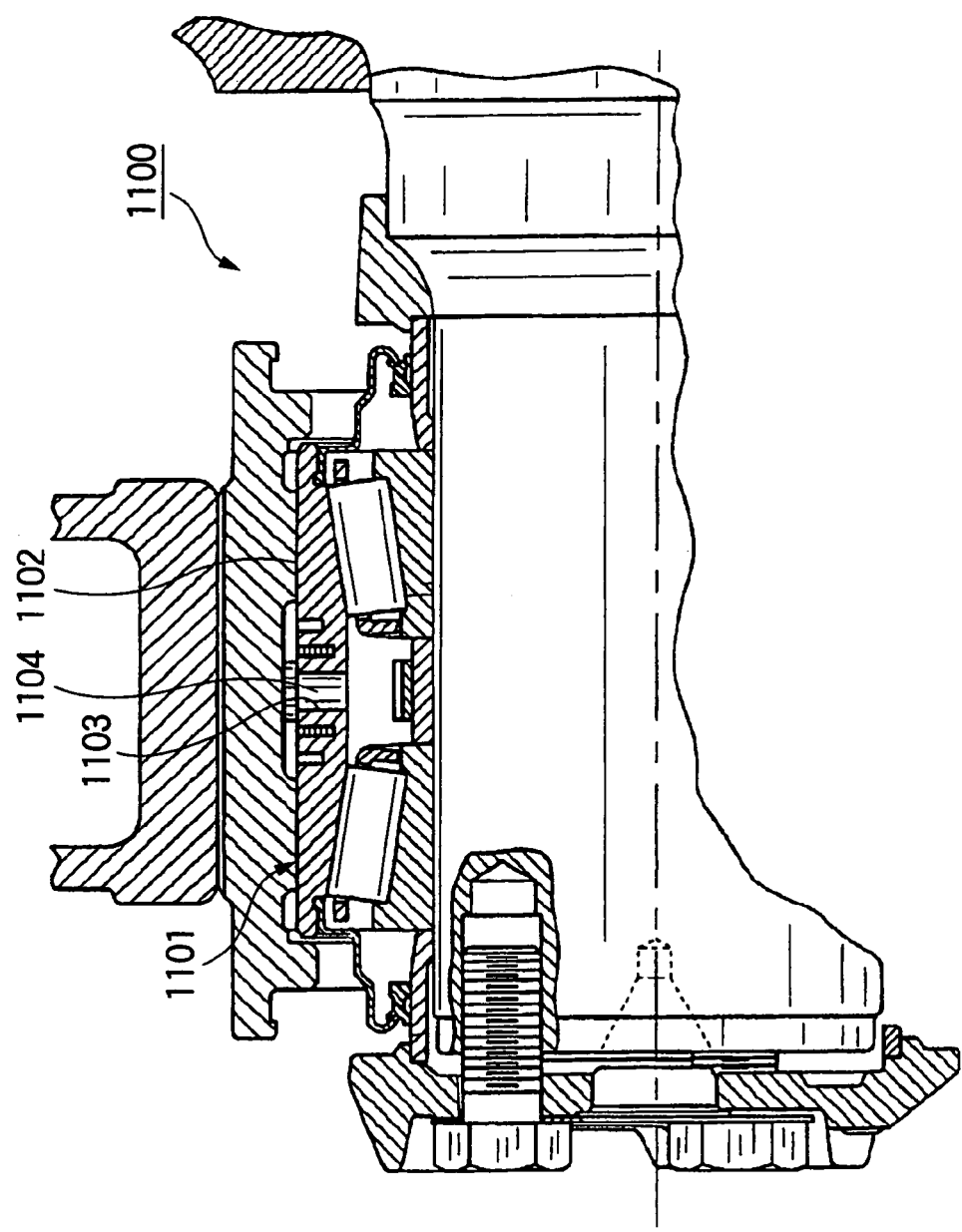
FIG. 50 is a sectional view showing a bearing unit in the prior art.
Figure 51:
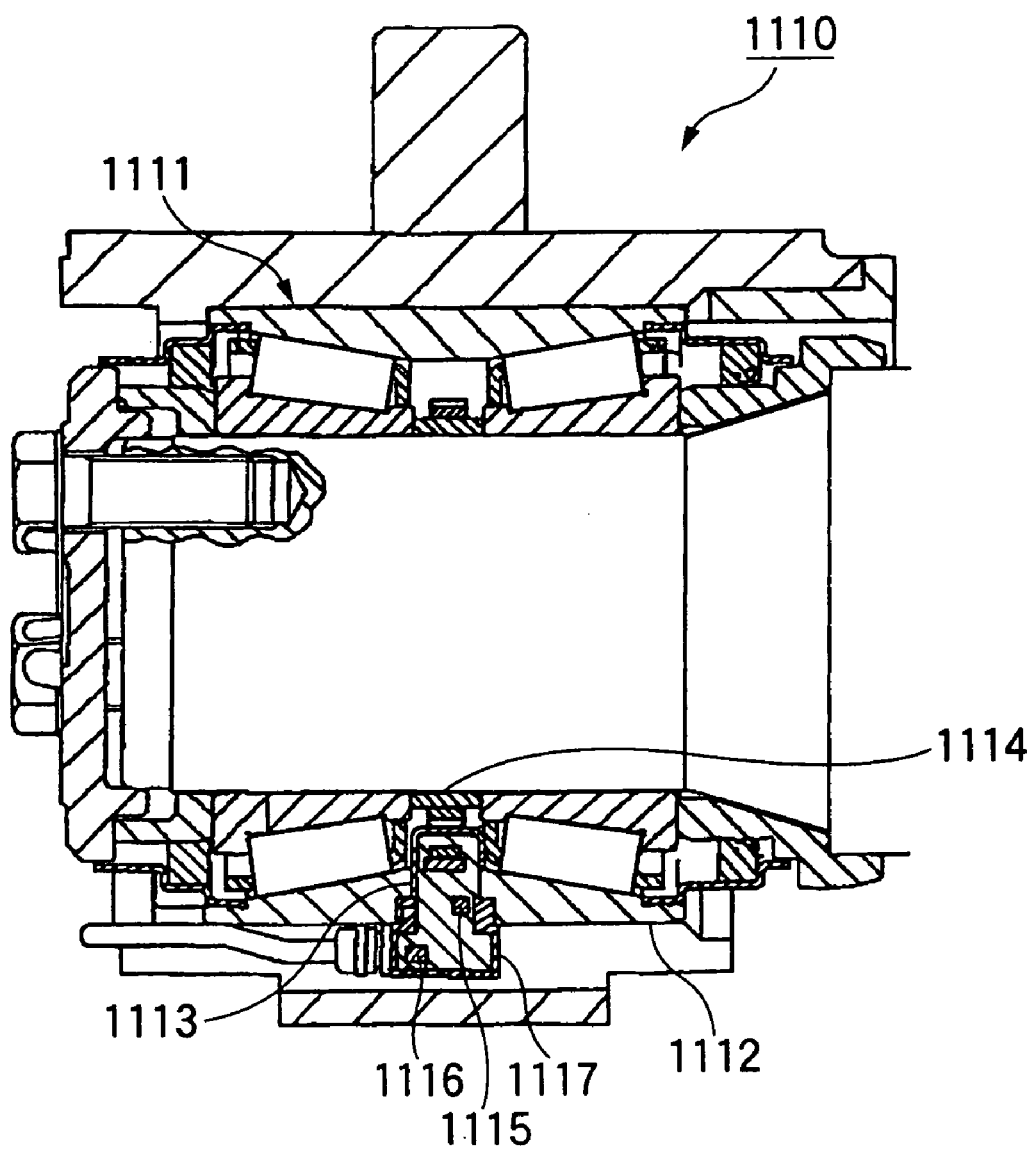
FIG. 51 is a sectional view showing another bearing unit in the prior art.
Figure 52:
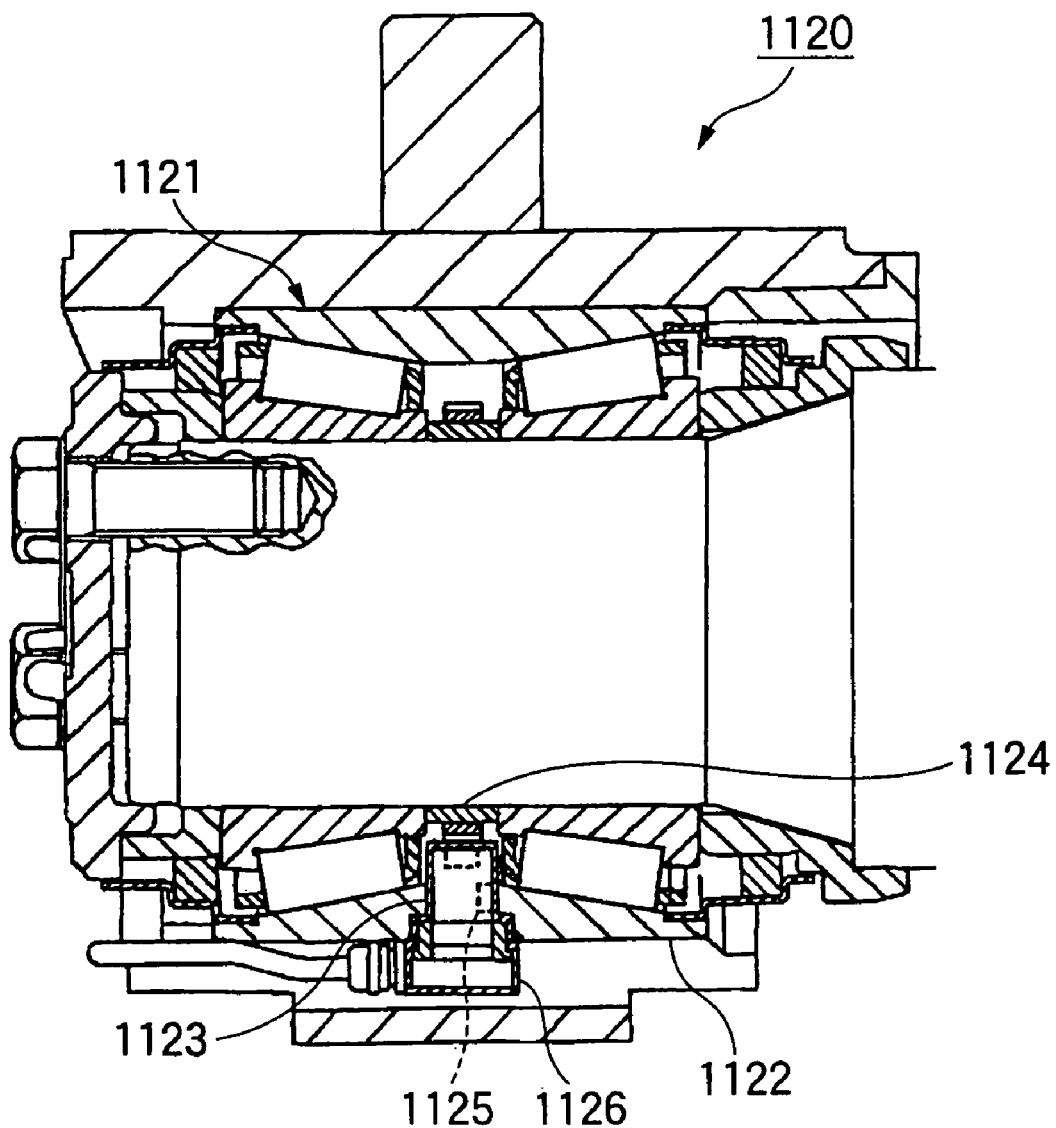
FIG. 52 is a sectional view showing still another bearing unit in the prior art.
Figure 53:
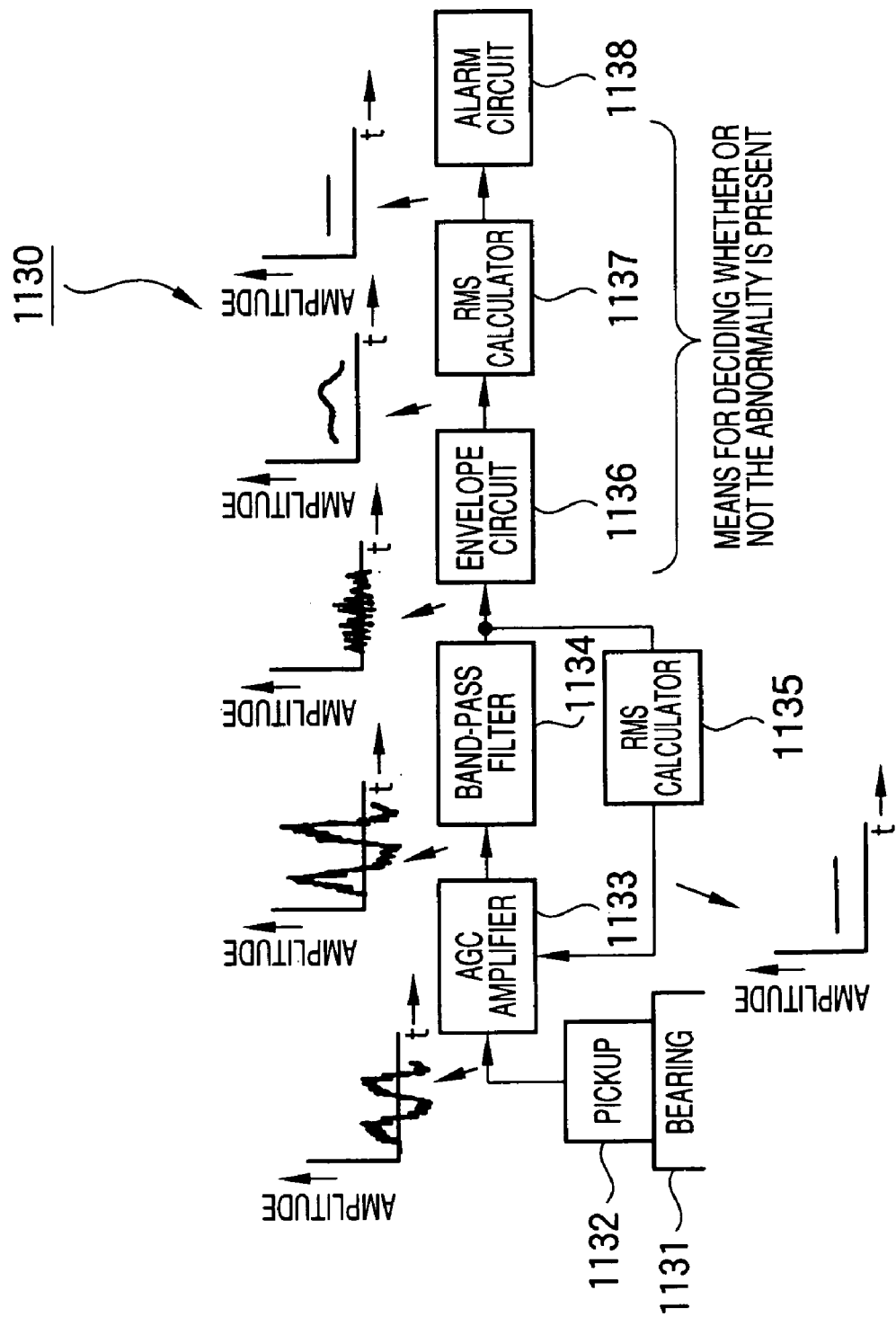
FIG. 53 is a block diagram showing another configurative example in the prior art.
Figure 54:
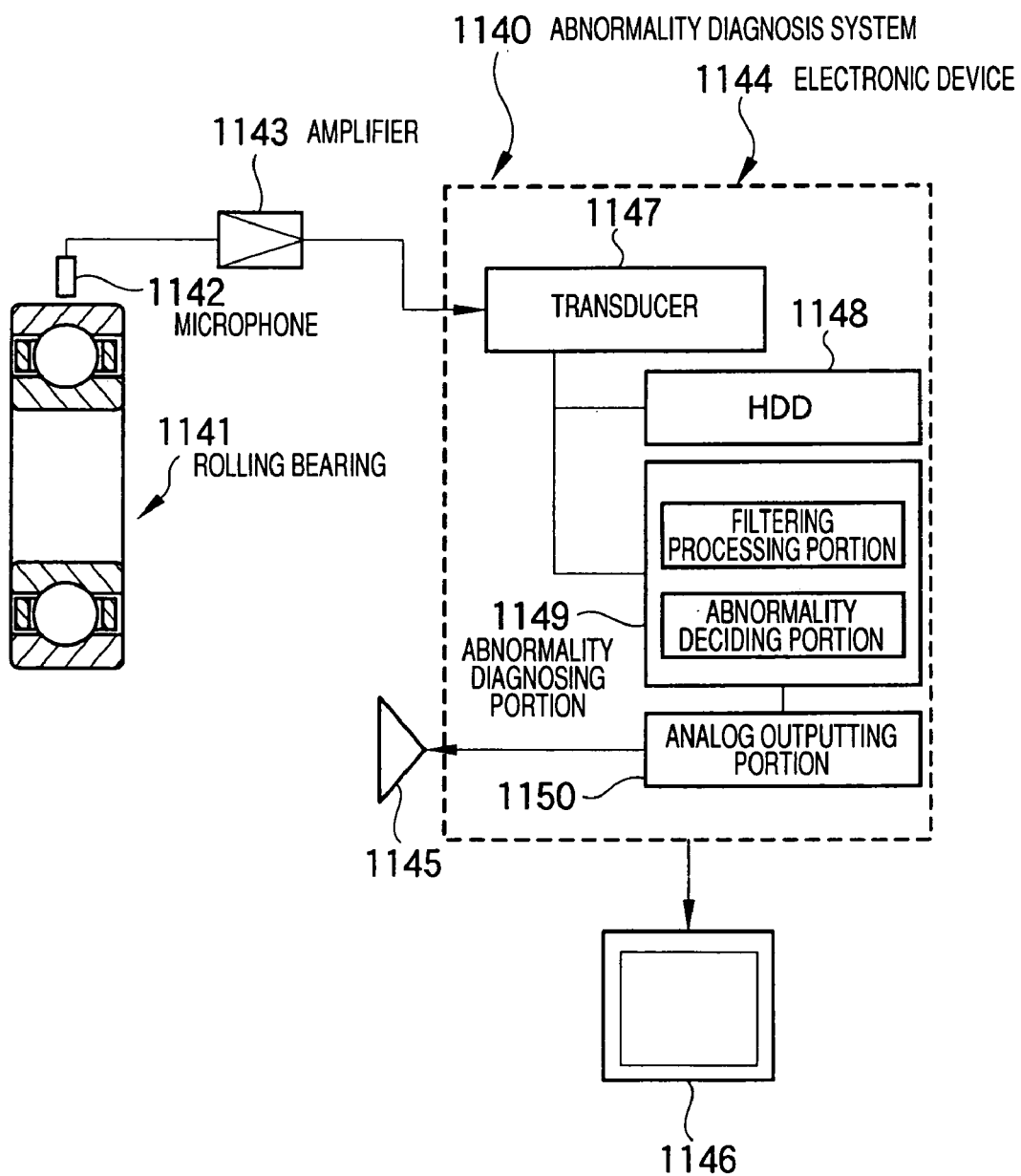
FIG. 54 is a block diagram showing still another configurative example in the prior art.
Figure 55:
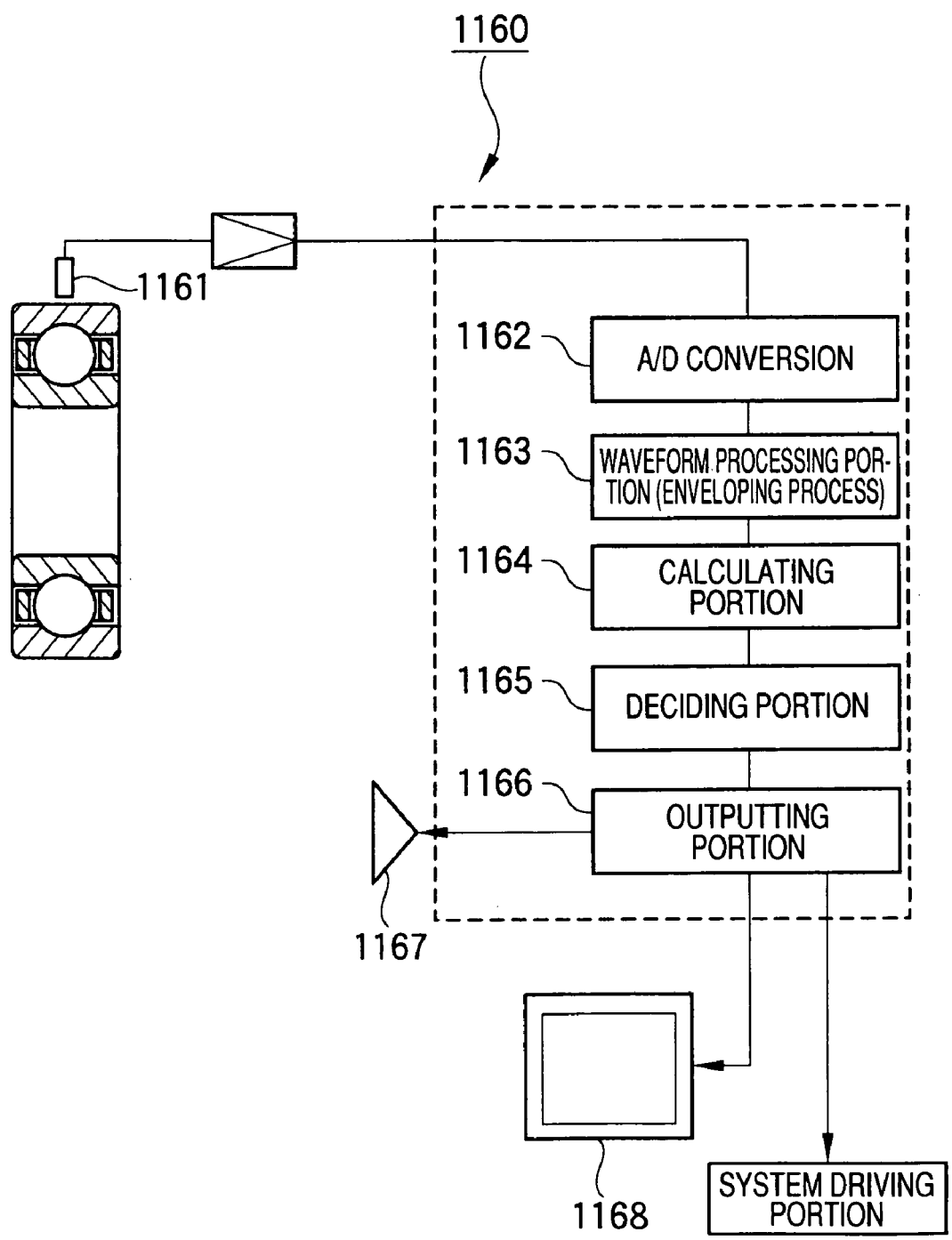
FIG. 55 is a block diagram showing yet still another configurative example in the prior art.

As shown in FIG. 49, in a bearing unit 460 of the present embodiment, a pair of recess portions 422d, 422d into which the abnormality sensing means is installed are formed on the outer peripheral surface of the housing 422 in the position that corresponds to the center portion in the width area of the inner ring raceway surfaces 415, 415 of the double row tapered roller bearing 411. First and second abnormality sensing means 461, 462 in which the temperature sensor 427 and the vibration sensor 428 are molded integrally in the case 429 are molded in the recess portions 422d, 422d with the resin.

The recess portions 422d, 422d are also arranged corresponding to the center portion in the width area of the outer ring raceway surfaces 417, 417.

In this case, the first and second abnormality sensing means 461, 462 are arranged in close vicinity to the position in which the tapered rollers 418 come into contact with the inner and outer ring raceway surfaces 415, 415, 417, 417 while rolling down. Therefore, the sensing sensitivity can be improved further, and a time required until the abnormal signal is generated when the abnormality occurs can be shortened. In the bearing unit 460 of the fifteenth embodiment, the same signal processing as that in the first embodiment is applied.

Also, the abnormality sensing means in which the temperature sensor and the vibration sensor are molded integrally may be fitted directly to the outer peripheral surface of the housing in the loading range. In such case, the abnormality sensing means should be fitted to the flat portion that is formed on a part of the outer peripheral surface of the housing. Then, the signal processing should be applied in the similar manner to respective embodiments. Also, like the present embodiment, the abnormality sensing means may be arranged on the outer diameter portion of the bearing housing in the loading range and in the width area of the inner ring raceway surfaces or the outer ring raceway surfaces.

Also, as the bearing used in the bearing unit, a combination of the cylindrical roller bearing and the single row radial ball bearing, or the cylindrical roller bearing or the tapered roller bearing or the self-aligning roller bearing may be applied.

Here, the machinery facility condition monitoring method and system and the abnormality diagnosis system according to the present invention are not limited to the foregoing embodiments, and appropriate variations, improvements, etc. can be applied. Also, in the present invention, respective embodiments can be employed in combination in the practicable range. Also, the machinery facility of the present invention includes the railway vehicle, the machine tool, the windmill, the reduction gear, the electric motor, and others, and any facility may be employed if the machinery facility includes at least one of the rotating body and the sliding member. Also, the rotating body or the sliding member of the present invention includes the rolling bearing, the sliding bearing, the ball screw, the linear guide, the linear ball bearing, other rotating parts (gear, wheel itself), and others.

The present invention is explained in detail with reference to particular embodiments, but it is apparent for the person skilled in the art that various variations and modifications can be applied without departing from a spirit and a scope of the present invention.

This application is filed based on
Japanese Patent Application (Patent Application No. 2002-252877) filed on Aug. 30, 2002,
Japanese Patent Application (Patent Application No. 2002-338423) filed on Nov. 21, 2002,
Japanese Patent Application (Patent Application No. 2002-370800) filed on Dec. 20, 2002,
Japanese Patent Application (Patent Application No. 2003-010131) filed on Jan. 17, 2003,
Japanese Patent Application (Patent Application No. 2003-048309) filed on Feb. 25, 2003,
Japanese Patent Application (Patent Application No. 2003-182996) filed on Jul. 26, 2003,
Japanese Patent Application (Patent Application No. 2003-304700) filed on Aug. 28, 2003,
and the contents thereof are incorporated by the reference hereinto.

INDUSTRIAL APPLICABILITY

There is provided the high-precision machinery facility abnormality diagnosis system that is capable of deciding the presence or absence of the abnormality in the state of normal use without decomposition of the facility like the machinery facility such as a railway vehicle facility, a machine tool, a windmill, or the like, which requires much time and labor to decompose, and thus capable of reducing the maintenance/administrative costs and being hardly affected by the noise, and the like.

The invention claimed is:

1. An abnormality diagnosis system for diagnosing a presence or absence of an abnormality of a bearing unit for a railway vehicle axle, comprising:
   a sensing/processing portion for outputting a signal generated from the bearing unit as an electric signal;
   a calculating/processing portion for making an abnormality diagnosis of the bearing unit based on an output of the sensing/processing portion;
   a result outputting portion for outputting a decision result of the calculating/processing portion; and
   a controlling/processing portion for feeding back a control signal to a control system of the railway vehicle based on the decision result.

2. An abnormality diagnosis system according to claim 1, wherein the calculating/processing portion includes
   a data accumulating/distributing portion for accumulating the electric signal fed from the sensing/processing portion and distributing the signal to an appropriate distributing route according to a type of the electric signal,
   an analyzing portion for calculating a predetermined physical quantity in regarding to the bearing unit based on the electric signal distributed from the data accumulating/distributing portion,
   a first data saving portion for saving bearing unit data in regarding to the bearing unit,
   a comparing/deciding portion for making the abnormality diagnosis of the bearing unit by comparing/referring an analyzed result of the analyzing portion with the bearing unit data saved in the first data saving portion, and
   a second data saving portion for saving the analyzed result of the analyzing portion and a decision result of the comparing/deciding portion.

3. An abnormality diagnosis system according to claim 2, wherein the analyzing portion includes
   a filtering processing portion for removing a noise component of the electric signal fed from the calculating/processing portion or extracting a particular frequency component to output, and
   a frequency analyzing portion for executing a frequency analysis of a signal output from the filtering processing portion, and
   the comparing/deciding portion makes the abnormality diagnosis of the bearing unit based on a result of the frequency analysis of the frequency analyzing portion.

4. An abnormality diagnosis system according to claim 2, wherein the analyzing portion has a temperature analyzing portion that calculates a temperature of the bearing unit based on the signal output from the data accumulating/distributing portion, and
   the comparing/deciding portion makes the abnormality diagnosis of the bearing unit based on the temperature calculated by the temperature analyzing portion.

5. An abnormality diagnosis system according to claim 2, wherein the analyzing portion has a rotation analyzing portion that calculates a rotation speed of the bearing unit based on the signal output from the data accumulating/distributing portion, and the comparing/deciding portion makes the abnormality diagnosis of the bearing unit based on the rotation speed calculated by the rotation analyzing portion.

6. An abnormality diagnosis system according to claim 1, wherein the calculating/processing portion outputs data saved in the second data saving portion to the controlling/processing portion in response to the abnormality diagnosis result.

7. An abnormality diagnosis system according to claim 1, wherein the filtering processing portion extracts only a frequency component of 1 kHz or less.

8. An abnormality diagnosis system according to claim 1, wherein a sensing element of the sensing/processing portion is arranged on a stationary portion of the bearing unit in a loading range.

9. An abnormality diagnosis system according to claim 1, wherein the data accumulating/distributing portion does not output the electric signal containing a noise component, which exceeds a predetermined level, to the analyzing portion.

10. An abnormality diagnosis system according to claim 1, wherein the comparing/deciding portion makes the abnormality diagnosis of the bearing unit by comparing levels of a frequency due to the abnormality and its higher harmonics with a reference value.

11. An abnormality diagnosis system according to claim 1, wherein the comparing/deciding portion decides that the abnormality is generated when at least one of peak values of the frequency due to the abnormal and its higher harmonics is larger than a predetermined reference value.

12. An abnormality diagnosis system according to claim 1, wherein the comparing/deciding portion estimates a degree of damage of the bearing unit based on the peak values of the frequency due to the abnormal and its higher harmonics.

13. An abnormality diagnosis system according to claim 1, wherein the comparing/deciding portion makes the abnormality diagnosis by comparing the levels of the frequency due to the abnormal and its higher harmonics.

14. An abnormality diagnosis system according to claim 1, wherein the comparing/deciding portion makes the abnormality diagnosis based on a square mean or a partial overall of a frequency band containing the frequency due to the abnormal.

15. An abnormality diagnosis system according to claim 1, wherein the comparing/deciding portion makes the abnormality diagnosis by applying a cepstrum analysis to a frequency spectrum.

16. An abnormality diagnosis system according to claim 1, wherein the signal is transmitted between the sensing/processing portion and the calculating/processing portion and the calculating/processing portion and the controlling/processing portion via a cable that has waterproof, oil-resistant, dustproof, rust-preventive, and moisture-proof functions, and heat-resistant, voltage-proof, and electromagnetic noise-resistant properties respectively.

17. An abnormality diagnosis system according to claim 1, wherein a radio communicating device is provided to the sensing/processing portion and the calculating!processing portion and the calculating/processing portion and the controlling/processing portion respectively, and the signal is transmitted therebetween by using the radio communicating device via radio.

18. An abnormality diagnosis system according to claim 1, wherein the signal is transmitted between the sensing/processing portion and the calculating/processing portion and the calculating/processing portion and the controlling/processing portion via the cable that has waterproof, oil-resistant, dustproof, rust-preventive, and moisture-proof functions, and heat-resistant, and electromagnetic noise-resistant properties respectively, or the signal is transmitted therebetween by using the radio communicating device.

19. An abnormality diagnosis system according to claim 1, wherein the abnormality diagnosis is made in real time.

20. An abnormality diagnosis system according to claim 1, wherein the abnormality diagnosis is made at a time different from a vehicle traveling time, based on data accumulated in the data accumulating/distributing portion.

21. An abnormality diagnosis system according to claim 1, wherein the presence or absence of the abnormality of a bearing in the bearing unit and an abnormality occurring location are diagnosed.

22. An abnormality diagnosis system according to claim 1, wherein a flat portion of a wheel is diagnosed.

23. An abnormality diagnosis system according to claim 1, wherein the presence or absence of the abnormality of a gear in the bearing unit and an abnormality occurring location are diagnosed.

24. An abnormality diagnosis system for a machinery facility having a rotating body, comprising:

a sensor unit having a sensor fitted to a constituent parts of the rotating body to sense a physical quantity of the rotating body in a rotating operation;

a calculating/processing portion for deciding a presence or absence of an abnormality of the rotating body by analyzing an output signal of the sensor unit and then comparing an analyzed result with predetermined reference data; and a controlling/processing portion for displaying the analyzed result of the calculating/processing portion and a decision result of the calculating/processing portion, and controlling an operation of the machinery facility in response to the decision result.

25. An abnormality diagnosis system according to claim 24, wherein the sensor unit has an output amplifying means for amplifying the output signal of the sensor.

26. An abnormality diagnosis system according to claim 24, wherein the sensor unit has a radio communicating means for transmitting the output signal to the calculating/processing portion via radio.

27. An abnormality diagnosis system according to claim 26, wherein the calculating/processing portion and the controlling/processing portion are provided to a monitoring base station that is remote from the rotating body.

28. An abnormality diagnosis system according to claim 27, wherein the sensor unit is fined to a bearing of a railway vehicle, and the sensor unit diagnoses the abnormality of the bearing.

29. A condition monitoring method for a machinery facility having at least one of a rotating body and a sliding member, comprising the steps of:

analyzing a predetermined physical quantity of the machinery facility based on a signal generated from the machinery facility;

provisionally diagnosing a presence or absence of an abnormality of the machinery facility by comparing/allocating an analyzed result with information serving as references to decide whether or not the abnormality is present in the machinery facility, upon elapse of a first time period; and diagnosing the presence or absence of the abnormality of the machinery facility and an abnormal location, by executing a total evaluation, which decides the abnormality when a number of times the abnormality is provisionally diagnosed exceeds a threshold value, after a comparison/allocation is executed a predetermined number of times or based on a compared/allocated result obtained upon elapse of a second time period.

30. A condition monitoring method for a machinery facility having at least one of a rotating body and a sliding member, comprising the steps of:

analyzing a predetermined physical quantity of the machinery facility based on a signal generated from the machinery facility;

provisionally diagnosing a presence or absence of an abnormality of the machinery facility by comparing/allocating an analyzed result with information serving as references to decide whether or not the abnormality is present in the machinery facility, upon elapse of a first time period; and diagnosing the presence or absence of the abnormality of the machinery facility and an abnormal location, by executing a total evaluation, which decides a degree of the abnormality according to a number of times the abnormality is provisionally diagnosed, after a comparison/allocation is executed predetermined number of times or based on a compared/allocated result obtained upon elapse of a second time period.

31. A machinery facility condition monitoring method according to claim 29, wherein the signal is A/D-converted into a digital signal, then a process of analyzing a frequency of the digital signal is executed, and then a frequency component generated due to a damage of the machinery facility and calculated based on an operating signal of the machinery facility is compared/allocated with a frequency component derived based on actually measured data during the first time period.

32. A machinery facility condition monitoring method according to claim 31, wherein the signal is subjected to an amplifying process and a filtering process.

33. A machinery facility condition monitoring method according to claim 31, wherein at least one of the rotating body and the sliding member of the machinery facility is any one of rolling bearing, ball screw, linear guide, and linear ball bearing, and the operating signal of the machinery facility is either a rotation speed signal in the rolling bearing and the ball screw or a moving speed signal in the linear guide and linear ball bearing.

34. A machinery facility condition monitoring system for a machinery facility having at least one of a rotating body and a sliding member and using the condition monitoring method set forth in claim 29, comprising:

at least one sensing/processing portion for sensing a signal generated from the machinery facility;

a calculating/processing portion having a microcomputer tat executes a calculating process to decide a condition of the machinery facility based on the signal output from the sensing/processing portion; and a controlling/processing portion having at least one of a result outputting portion that outputs a decision result of the calculating/processing portion and a controller that feeds back a control signal to a control system of the machinery facility based on the decision result.

35. A machinery facility condition monitoring system according to claim 34, wherein at least one of the sensing processing portion and the microcomputer is installed into the rotating body and the sliding member.

36. A machinery facility condition monitoring system according to claim 34, wherein at least one of the rotating body and the sliding member is a bearing to which a radial load is applied, and the sensing/processing portion is fixed in a radial load loading range of a bearing housing that is fitted onto a raceway ring of the bearing.

37. An abnormality diagnosis system for a railway vehicle bearing unit using the machinery facility condition monitoring system set forth in claim 34.

38. An abnormality diagnosis system for a windmill bearing unit using the machinery facility condition monitoring system set forth in claim 34.

39. An abnormality diagnosis system for a machine tool spindle bearing unit using the machinery facility condition monitoring system set forth in claim 34.

40. A machine equipment abnormality diagnosis system comprising:

a sensing/processing portion having a sensor unit that is fixed to a bolt screwed into a housing of the machine equipment and outputs a signal generated from the machine equipment as an electric signal;

a calculating/processing portion for making an abnormality diagnosis of the machine equipment based on an output of the sensing/processing portion; and a controlling/processing portion for feeding back a control signal to a control system of the machine equipment based on a result of the abnormality diagnosis.

41. A machine equipment abnormality diagnosis system according to claim 40, wherein the calculating/processing portion includes the calculating/processing portion includes a data accumulating/distributing portion for accumulating the electric signal fed from the sensing/processing portion and distributing the signal to an appropriate distributing route according to a type of the electric signal, an analyzing portion for calculating a predetermined physical quantity in regarding to the machine equipment based on the electric signal distributed from the data accumulating/distributing portion, a first data saving portion for saving machine equipment data in regarding to the machine equipment, a comparing/deciding portion for making the abnormality diagnosis of the machine equipment by comparing the physical quantity calculated by the analyzing portion with the machine equipment data saved in the first data saving portion, a second data saving portion for saving the analyzed result of the analyzing portion and a result of the abnormality diagnosis of the comparing/deciding portion.

42. A machine equipment abnormality diagnosis system according to claim 40, wherein the calculating/processing portion and the controlling/processing portion are composed of a microcomputer or an IC chip.

43. A machine equipment abnormality diagnosis system according to claim 40, wherein the signal is transmitted between the sensing/processing portion and the calculating/processing portion or the calculating/processing portion and the controlling/processing portion without a wire connection.

44. A bearing unit including an inner ring having an inner ring raceway surface, an outer ring having an outer ring raceway surface, a plurality of rolling elements arranged relatively rotatably between the inner ring raceway surface and the outer ring raceway surface, and a retainer for holding rollably the rolling elements, whereby a bearing to which a radial load is applied is arranged in a bearing housing, the bearing unit comprising:

an abnormality sensing means provided in a loading range of the bearing housing, for sensing an abnormality from at least one selected from a vibration sensor and a temperature sensor installed/fixed in a single case, wherein a filtering processing portion for removing an unnecessary frequency band from a vibration waveform from the vibration sensor, an envelope processing portion for detecting an absolute value of a filtered waveform transferred from the filtering processing portion, a frequency analyzing portion for analyzing a frequency of a waveform transferred from the envelope processing portion, a comparing/collating portion for comparing a frequency generated due to a damage calculated based on a rotation speed with a frequency derived based on actually measured data, and a result outputting portion for identifying a presence or absence of the abnormality and an abnormal location based on a compared result in the comparing/collating portion are provided.

45. A machinery facility condition monitoring method according to claim 30, wherein the signal is A/D-converted into a digital signal, then a process of analyzing a frequency of the digital signal is executed, and then a frequency component generated due to a damage of the machinery facility and calculated based on an operating signal of the machinery facility is compared/allocated with a frequency component derived based on actually measured data measured during the first time period.

* * * * *